(12) United States Patent
Tsuchida et al.

(10) Patent No.: US 7,867,973 B2
(45) Date of Patent: Jan. 11, 2011

(54) FOLLISTATIN VARIANT POLYPEPTIDE

(75) Inventors: Kunihiro Tsuchida, Aichi (JP); Tatsuya Murakami, Tokyo (JP)

(73) Assignee: Techno Networks Shikoku Co., Ltd., Kagawa (JP)

( * ) Notice: Subject to any disclaimer, the term of this patent is extended or adjusted under 35 U.S.C. 154(b) by 0 days.

(21) Appl. No.: 11/578,408

(22) PCT Filed: Apr. 15, 2005

(86) PCT No.: PCT/JP2005/007662

§ 371 (c)(1),
(2), (4) Date: Oct. 13, 2006

(87) PCT Pub. No.: WO2005/100563

PCT Pub. Date: Oct. 27, 2005

(65) Prior Publication Data

US 2008/0090755 A1    Apr. 17, 2008

(30) Foreign Application Priority Data

Apr. 15, 2004  (JP)  ............... 2004-120023
Dec. 8, 2004   (JP)  ............... 2004-355293

(51) Int. Cl.
  C12P 21/04  (2006.01)
  A61K 38/18  (2006.01)
  C07K 14/475 (2006.01)
(52) U.S. Cl. .............. 514/12; 435/69.7; 530/350
(58) Field of Classification Search .............. None
  See application file for complete search history.

(56) References Cited

U.S. PATENT DOCUMENTS

| 5,182,375 | A * | 1/1993 | Ling et al. .............. 536/23.5 |
| 5,545,616 | A | 8/1996 | Woodruff |
| 6,004,937 | A | 12/1999 | Wood et al. |
| 6,096,506 | A | 8/2000 | Lee et al. |
| 2002/0157126 | A1 | 10/2002 | Lee et al. |
| 2003/0162714 | A1 | 8/2003 | Hill et al. |
| 2003/0162717 | A1 | 8/2003 | Schacter et al. |

FOREIGN PATENT DOCUMENTS

| CN | 1355881 | 6/2002 |
| WO | 99/42573 | 8/1999 |
| WO | 99/45949 | 9/1999 |
| WO | 00/43781 | 7/2000 |
| WO | 01/05820 | 1/2001 |
| WO | 2001/0032871 | 5/2001 |
| WO | 01/53350 | 7/2001 |
| WO | 02/10214 | 2/2002 |
| WO | 02/055077 | 7/2002 |
| WO | 03/072715 | 9/2003 |

OTHER PUBLICATIONS

McPherron et al., "Regulation of skeletal muscle mass in mice by a new TGF-β superfamily member," Nature, 387(6628):83-90 (1997).
Nakamura et al., "Activin-Binding Protein from Rat Ovary Is Follistatin," Science, 247(4944):836-838 (1990).
Lee et al., "Regulation of myostatin activity and muscle growth," Proc. Natl. Acad. Sci. USA, 98(16):9306-9311 (2001).
Shiozaki et al., "Evidence for the participation of endogenous activin A/erythroid differentiation factor in the regulation of erythropoisis," Proc. Natl. Acad. Sci. USA, 89(5):1553-1556 (1992).
Zimmers et al., "Induction of Cachexia in Mice by Systemically Administered Myostatin," Science, 296(5572):1486-1488 (2002).
Gonzalez-Cadavid et al., "Organization of the human myostatin gene and expression in healthy men and HIV-infected men with muscle wasting," Proc. Natl. Acad. Sci. USA, 95(25):14938-14943 (1998).
Wagner et al., "Loss of Myostatin Attenuates Severity of Muscular Dystrophy in mdx Mice," Ann. Neurol., 52(6):832-836 (2002).

(Continued)

*Primary Examiner*—Marianne P Allen
(74) *Attorney, Agent, or Firm*—Greenblum & Bernstein P.L.C.

(57) ABSTRACT

The object of the present invention is to provide a follistatin variant capable of specifically inhibiting GDF-8 activity without inhibiting activin activity. The present invention provides a follistatin variant polypeptide, which (a) comprises follistatin domain I; (b) does not comprise an amino acid sequence that is represented by formula (I): Cys-$(X^1)_a$-Cys-$(X^2)_b$-Cys-$(X^3)_c$-Cys-$(X^4)_d$-Cys-$(X^5)_e$-Cys-$(X^6)_f$-Cys-$(X^7)_g$-Cys-$(X^8)_h$-Cys-$(X^9)_i$-Cys (SEQ ID NO: 30) wherein $X^1$, $X^2$, $X^3$, $X^4$, $X^5$, $X^6$, $X^7$, $X^8$, and $X^9$ each independently represents the same or a different naturally occurring amino acid residue other than cysteine, "a" represents an integer between 2 and 6, "b" represents an integer between 3 and 7, "c" represents an integer between 7 and 11, "d" represents an integer between 0 and 4, "e" represents an integer between 1 and 6, "f" and "g" represent integers between 8 and 12, "h" represents an integer between 4 and 8, and "i" represents an integer between 11 and 15) and has 50% or more homology with the amino acid sequence of SEQ ID NO: 2 or SEQ ID NO: 29; and (c) selectively inhibits GDF-8 activity as compared with its inhibition of activin activity.

8 Claims, 19 Drawing Sheets

OTHER PUBLICATIONS

McPherron et al., "Suppression of body fat accumulation in myostatin-deficient mice," *The Journal of Clinical Investigation*, 109(5):595-601 (2002).

Uchida Tohru et al., "A Novel Epidermal Growth Factor-like Molecule Containing Two Follistatin Modules Stimulates Tyrosine Phophorylation of erbB-4 in MKN28 Gastric Cancer Cells", Biochemical Biophysical Research Communications, vol. 266, pp. 593-602 (1999).

Liang Gangning et al., "The Gene for a Novel Transmembrane Protein Containing Epidermal Growth Factor and Follistatin Domain is Frequently Hypermethylated in Human Tumor Cells", Cancer Research, vol. 60, pp. 4907-4912 (2000).

Shimasaki Shun'ichi et al., "Primary Structure of the Human Follistatin Precursor and its Genomic Organization", Proc. Natl. Acad. Sci. USA, vol. 85, pp. 4218-4222 (1988).

Robertson D.M. et al., "The Isolation of Polypeptides with FSH Suppressing Activity from Bovine Follicular Fluid which are Structurally Different to Inhibin", Biochemical and Biophysical Research Communications, vol. 149, No. 2, pp. 744-749 (1987).

Ueno Naoto et al., "Isolation and Partial Characterization of Follistatin: A Single-Chain Mr35, 000 Monomeric Protein that Inhibits the Release of Follicle-Stimulating Hormone", Proc. Natl. Acad. Sci. USA, vol. 84, pp. 8282-8286 (1987).

Inouye et al. Biochemical and Biophysical Research Communications, vol. 179, No. 1, pp. 352-358, 1991.

Sidis et al. The Journal of Biological Chemistry, vol. 276, No. 21, pp. 17718-17726, 2001.

Tsuchida et al., J. Biol. Chem. (2000), vol. 275, No. 52, pp. 40788-40796.

Sidis et al., Endrocrinology, (2002), vol. 143, pp. 1613-1624.

Office Action in counterpart Japanese application No. 2004-355294, dated Oct. 19, 2010.

English Translation of Office Action in counterpart Japanese application No. 2004-355294, dated Oct. 19, 2010.

\* cited by examiner

Fig.1

```
                                    FSN
human   : GNCWLRQAKNGRCQVLYKTELSKEECCSTGRLSTSWTEEDVNDNTLFKWMIFNGGAPNCIPCKET
mouse   : GNCWLRQAKNGRCQVLYKTELSKEECCSTGRLSTSWTEEDVNDNTLFKWMIFNGGAPNCIPCKET
rat     : GNCWLRQAKNGRCQVLYKTELSKEECCSTGRLSTSWTEEDVNDNTLFKWMIFNGGAPNCIPCKET
cattle  : GNCWLRQAKNGRCQVLYKTELSKEECCSTGRLSTSWTEEDVNDNTLFKWMIFNGGAPNCIPCKET
pig     : GNCWLRQAKNGRCQVLYKTELSKEECCSTGRLSTSWTEEDVNDNTLFKWMIFNGGAPNCIPCKET
sheep   : GNCWLRQAKNGRCQVLYKTELSKEECCSTGRLSTSWTEEDVNDNTLFKWMIFNGGAPNCIPCKET
horse   : GNCWLRQAKNGRCQVLYKTELSKEECCSTGRLSTSWTEEDVNDNTLFKWMIFNGGAPNCIPCKET
chicken : GNCWLRQARNGRCQVLYKTDLSKEECCKSGRLTTSWTEEDVNDNTLFKWMIFNGGAPNCIPCKET FSI
human    : CENVDCGPGKKCRMNKKNKPRCVCAPDCSNITWKGPVCGLDGKTYRNECALLKARCKEQPELEVQYQGRC KKT
mouse    : CENVDCGPGKKCRMNKKNKPRCVCAPDCSNITWKGPVCGLDGKTYRNECALLKARCKEQPELEVQYQGKC KKT
rat      : CENVDCGPGKKCRMNKKNKPRCVCAPDCSNITWKGPVCGLDGKTYRNECALLKARCKEQPELEVQYQGKC KKT
cattle   : CENVDCGPGKKCRMNKKNKPRCVCAPDCSNITWKGPVCGLDGKTYRNECALLKARCKEQPELEVQYQGKC KKT
pig      : CENVDCGPGKKCRMNKKNKPRCVCAPDCSNITWKGPVCGLDGKTYRNECALLKARCKEQPELEVQYQGKC KKT
sheep    : CENVDCGPGKKCRMNKKNKPRCVCAPDCSNITWKGPVCGLDGKTYRNECALLKARCKEQPELEVQYQGKC KKT
horse    : CDNVDCGPGKKCRMNKKNKPRCVCAPDCSNITWKGPVCGLDGKTYRNECALLKARCKEQPELEVQYQGKC KKT
chicken  : CENVDCGPGKKCKMNKKNKPRCVCAPDCSNITWKGPVCGLDGKTYRNECALLKARCKEQPELEVQYQGKC KKT
consensus: CENVDCGPGKKCRMNKKNKPRCVCAPDCSNITWKGPVCGLDGKTYRNECALLKARCKEQPELEVQYQGKC
           D           K                                                   R FSII
human    : CRDVFCPGSSTCVVDQTNNAYCVTCNRICPEPASSEQYLCGNDGVTYSSACHLRKATCLLGRSIGLAYEGKC IKAKS
mouse    : CRDVFCPGSSTCVVDQTNNAYCVTCNRICPEPSSSEQYLCGNDGVTYSSACHLRKATCLLGRSIGLAYEGKC IT-KS
rat      : CRDVFCPGSSTCVVDQTNNAYCVTCNRICPEPSSSEQSLCGNDGVTYSSACHLRKATCLLGRSIGLAYEGKC IKAKS
cattle   : CRDVFCPGSSTCVVDQTNNAYCVTCNRICPEPTSSEQYLCGNDGVTYPSACHLRKATCLLGRSIGLAYEGKC IKAKS
pig      : CRDVFCPGSSTCVVDQTNNAYCVTCNRICPEPTSSEQYLCGNDGVTYSSACHLRKATCLLGRSIGLAYEGKC IKAKS
sheep    : CRDVFCPGSSTCVVDQTNNAYCVTCNRICPEPTSSEQYLCGNDGVTYPSACHLRKATCLLGRSIGLAYEGKC IKAKS
horse    : CRDVNCPGSSTCVVDQTNNAYCVTCNRICPEPTSSEQYLCGNDGVTYSSACHLRKATCLLGRSIGLAYEGKC IKAKS
chicken  : CRDVLCPGSSTCVVDQTNNAYCVTCNRICPEPTSPEQYLCGNDGITYASACHLRKATCLLGRSIGLAYEGKC IKAKS
consensus: CRDVXCPGSSTCVVDQTNNAYCVTCNRICPEPXSXEQXLCGNDGXTYXSACHLRKATCLLGRSIGLAYEGKC FSIII
human   : CEDIQCTGGKKCLWDFKVGRGRCSLCDELCPDSKSDEPVCASDNATYASECAMKEAACSSGVLLEVKHSGSC
mouse   : CEDIQCGGGKKCLWDSKVGRGRCSLCDELCPDSKSDEPVCASDNATYASECAMKEAACSSGVLLEVKHSGSC
rat     : CEDIQCGGGKKCLWDFKVGRGRCSLCDELCPDSKSDEPVCASDNATYASECAMKEAACSSGVLLEVKHSGSC
cattle  : CDDIQCTGGKKCLWDFKVGRGRCSLCGELCPESKSEEPVCASDNATYASECAMKEAACSSGVLLEVKHSGSC
pig     : CEDIQCTGGKKCLWDFKVGRGRCSLCDELCPESKSEEPVCASDNATYASECAMKEAACSSGVLLEVKHSGSC
sheep   : CEDIQCTGGKKCLWDFKVGRGRCSLCGELCPESKSEEPVCASDNATYASECAMKEAACSSGVLLEVKHSGSC
horse   : CEDIQCTGGKKCLWDFKVGRGRCSLCDELCPDSKSEEPVCASDNATYASECAMKEAACSSGVLLEVKHSGSC
chicken : CEDIQCSAGKKCLWDFKVGRGRCALCDELCPESKSDEAVCASDNTTYPSECAMKEAACSMGVLLEVKHSGSC human   : NSISEDTEEEEEDEDQDYSFPISSILEW
mouse   : NSISEETEEEEEEEDQDYSFPISSILEW
rat     : NSISEETEEEEEEEDQDYSFPISSTLEW
cattle  : NSISEDTEDEEEDEDQDYSFPISSILEW
pig     : NSISEDTEEEEEDEDQDYSFPISSILEW
sheep   : NSISEDTEDEEEDEDQDYSFPISSILEW
horse   : NSISEDTEEEEEDEDQDYSFPISSILEW
chicken : NSINEDPEEEEEDEDQDYSFPISSILEW
```

Fig.14

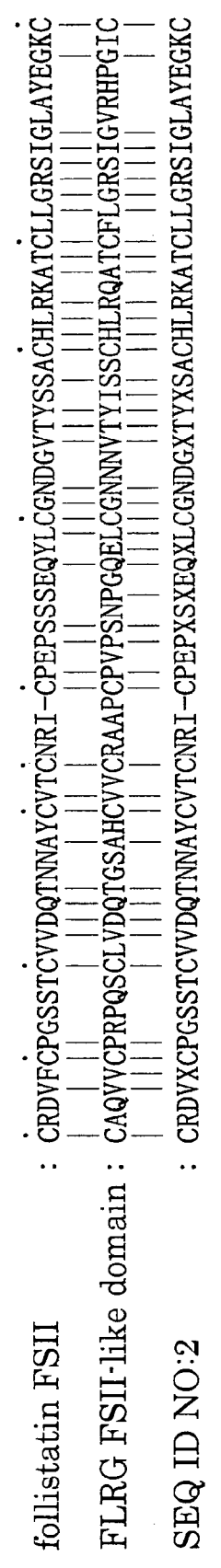

| | | |
|---|---|---|
| follistatin FSII | : | CRDVFCPGSSTCVVDQTNNAYCVTCNRI-CPEPSSSEQYLCGNDGVTYSSACHLRKATCLLGRSIGLAYEGKC |
| FLRG FSII-like domain | : | CAQVVCPRPQSCLVDQTGSAHCVVCRAAPCPVPSNPGQELCGNNNVTYISSCHLRQATCFLGRSIGVRHPGIC |
| SEQ ID NO:2 | : | CRDVXCPGSSTCVVDQTNNAYCVTCNRI-CPEPXSXEQXLCGNDGXTYXSACHLRKATCLLGRSIGLAYEGKC |

FOLLISTATIN VARIANT POLYPEPTIDE

TECHNICAL FIELD

The present invention relates to a follistatin variant polypeptide that selectively inhibits the activity of growth/differentiation factor-8 (GDF-8) as compared with its inhibition of activin activity.

BACKGROUND ART

Activin belongs to the transforming growth factor-β (TGF-β) superfamily and is a multifunctional growth-differentiation factor for differentiation induction of erythroblastic cells, secretion of follicle stimulating hormone (FSH) from the hypophysis, and promotion of luteinization caused by FSH, action to maintain the survival of nerve cells, and action to promote insulin production, for example.

Growth/differentiation factor-8 (GDF-8) has been discovered as a member of the TGF-β superfamily belonging to the activin subfamily and being specifically expressed during development and in the skeletal muscles of an adult (Nature, England, 1997, Vol. 387, No. 6628, pp. 83-90). GDF-8 is also referred to as myostatin and has a function to negatively control the muscle volume. In the case of a GDF-8-deficient mouse, the muscle volume increases to 2 to 3 times greater than that of a wild-type mouse (Nature, England, 1997, Vol. 387, No. 6628, pp. 83-90).

Follistatin binds strongly to activin (Science, U.S.A., 1990, Vol. 247, No. 4944, pp. 836-838) and to GDF-8 (Proceedings of the National Academy of Sciences of the United States of America, U.S.A., 2001, Vol. 98, No. 16, pp. 9306-9311) (dissociation constant to activin: $K_d$=540-680 pmol/L), and neutralize their activities. Furthermore, data has been accumulated that suggests direct and indirect in vivo involvement of follistatin in control of various physiological activities of activin and GDF-8. When follistatin is continuously administered to a mouse via an osmotic mini pump, the number of erythroblastic progenitor cells in the bone marrow or the spleen is significantly decreased (Proceedings of the National Academy of Sciences of the United States of America, U.S.A., 1992, Vol. 89, No. 5, pp. 1553-1556), and the skeletal muscle mass is significantly increased in the case of a transgenic mouse which expresses follistatin under control of a skeletal-muscle-specific promoter (Proceedings of the National Academy of Sciences of the United States of America, U.S.A., 2001, Vol. 98, No. 16, pp. 9306-9311).

Analysis of the amino acid sequence of follistatin has revealed that follistatin comprises 4 domains (from the N-terminal side): the N-terminal domain, follistatin domain I, follistatin domain II, and follistatin domain III (Proceedings of the National Academy of Sciences of the United States of America, U.S.A., 1988, Vol. 85, No. 12, pp. 4218-4222). The follistatin domains are thought to be involved in binding to activin or other growth factors.

In recent years, there have been reports suggesting that GDF-8 is involved in various diseases. Zimmers et al. have demonstrated that transplantation of cells stably expressing GDF-8 into the femoral region of a nude mouse results in induction of cachexic symptoms including decreased skeletal muscle and fat (Science, U.S.A., 2002, Vol. 296, No. 5572, pp. 1486-1488). An increased amount of anti-GDF-8-antibody-positive protein in the muscle of an HIV patient with body weight loss has also been reported (Proceedings of the National Academy of Sciences of the United States of America, U.S.A., 1998, Vol. 95, No. 25, pp. 14938-14943). It has also been reported that in the case of mice obtained through mating mdx mice, the model mice of Duchenne muscular dystrophy, with GDF-8-deficient mice, both muscle mass and muscle functions are improved as compared with those of mdx mice (Annals of Neurology, U.S.A., 2002, Vol. 52, No. 6, pp. 832-836). Moreover, since decreases in fat levels as well as increases in skeletal muscle are observed in the case of GDF-8-deficient mice and GDF-8 gene deficiency caused in diabetes model mice results in suppression of fat accumulation and abnormal glucose metabolism, involvement of GDF-8 in the onset of or progression of pathological conditions of obesity or Type II diabetes has also been suggested (The Journal of Clinical Investigation, U.S.A., 2002, Vol. 109, No. 5, pp. 595-601).

As described above, it is thought that through inhibition of GDF-8 activity, these diseases, to the onset or the progress of the pathological conditions of which GDF-8 contributes, can be treated. Moreover, for alleviating side effects, it is preferable to selectively inhibit GDF-8 activity without inhibiting activin activity. As substances that inhibit GDF-8 activity, follistatin (Description of U.S. patent application publication No. 2002/0157126 and JP Patent Publication (Kohyo) No. 2002-506044 A), an anti-GDF-8 antibody (Description of U.S. Pat. No. 6,096,506), a GDF-8 propeptide (International Patent Publication No. 02/09641 pamphlet), a dominant negative GDF-8 variant (International Patent Publication No. 01/53350 pamphlet, and International Patent Publication No. 00/43781 pamphlet), a GDF-8 antigen (Description of U.S. Pat. No. 6,369,201, International Patent Publication No. 01/05820 pamphlet, and International Patent Publication No. 99/42573 pamphlet), a GDF-8 receptor and an anti-GDF-8 receptor antibody (International Patent Publication No. 02/10214 pamphlet), and a Smad2 or Smad3 phosphorylation inhibitor (International Patent Publication No. 02/055077 pamphlet), for example, are known.

DISCLOSURE OF THE INVENTION

An object to be achieved by the present invention is to provide a follistatin variant capable of selectively inhibiting GDF-8 activity which has been suggested to contribute to the onset of and/or progression of pathological conditions of cachexia, muscular dystrophy, obesity, and Type II diabetes, as compared with its inhibition of activin activity, without inhibiting activin activity which has important functions such as pituitary FSH secretion, luteal maturation, erythroblastic differentiation induction, and insulin secretion.

The present invention relates to the following (1) to (28).

(1) A follistatin variant polypeptide, which (a) comprises follistatin domain I; (b) does not comprise an amino acid sequence that is represented by formula (I): Cys-$(X^1)_a$-Cys-$(X^2)_b$-Cys-$(X^3)_c$-Cys-$(X^4)_d$-Cys-$(X^5)_e$-Cys-$(X^6)_f$-Cys-$(X^7)_g$-Cys-$(X^8)_h$-Cys-$(X^9)_i$-Cys (SEQ ID NO: 30) wherein $X^1$, $X^2$, $X^3$, $X^4$, $X^5$, $X^6$, $X^7$, $X^8$, and $X^9$ each independently represents the same or a different naturally occurring amino acid residue other than cysteine, "a" represents an integer between 2 and 6, "b" represents an integer between 3 and 7, "c" represents an integer between 7 and 11, "d" represents an integer between 0 and 4, "e" represents an integer between 1 and 6, "f" and "g" represent integers between 8 and 12, "h" represents an integer between 4 and 8, and "i" represents an integer between 11 and 15) and has 50% or more homology with the amino acid sequence of SEQ ID NO: 2 or SEQ ID NO: 29; and (c) selectively inhibits GDF-8 activity as compared with its inhibition of activin activity.

(2) The follistatin variant polypeptide according to (1), which comprises follistatin domain I and lacks follistatin domain II.
(3) The follistatin variant polypeptide according to (1) or (2), which further does not comprise follistatin domain III.
(4) The follistatin variant polypeptide according to any one of (1) to (3), which comprises 2 or more follistatin domains I.
(5) The follistatin variant polypeptide according to any one of (1) to (4), which further comprises an N-terminal domain.
(6) The follistatin variant polypeptide according to (1) or (2), which comprises any one domain structure selected from FSI, FSI-FSI, FSI-FSI-FSIII, FSN-FSI, FSN-FSI-FSI, and FSN-FSI-FSI-FSIII wherein FSI denotes follistatin domain I, FSIII denotes follistatin domain III, FSN denotes an N-terminal domain, and the domains are each linked directly or via a linker polypeptide.
(7) The follistatin variant polypeptide according to any one of (1) to (6), wherein follistatin domain I is a polypeptide comprising the amino acid sequence of SEQ ID NO: 1.
(8) The follistatin variant polypeptide according to (7), which comprises the amino acid sequence ranging from the 30$^{th}$ to the 166$^{th}$ amino acids of SEQ ID NO: 4.
(9) The follistatin variant polypeptide according to any one of (1) to (8), wherein another polypeptide is fused to the N-terminus or the C-terminus of the amino acid sequence of a follistatin domain.
(10) A polypeptide, which comprises the amino acid sequence of SEQ ID NO: 6, 8, or 10.
(11) A polynucleotide, which encodes the polypeptide according to any one of (1) to (10).
(12) The polynucleotide according to (11), which comprises the nucleotide sequence of SEQ ID NO: 5, 7, or 9.
(13) A vector, which comprises the polynucleotide according to (11) or (12).
(14) A transformed cell, which is obtained by introducing the vector according to (13) into a host cell.
(15) A method for producing a polypeptide, which comprises culturing the transformed cell according to (14) in a medium, causing the polypeptide according to any one of (1) to (10) expressed in the cell to be accumulated in the medium or the cell, and harvesting the polypeptide from the medium or the cell.
(16) A GDF-8-selective inhibitor, which comprises the polypeptide according to any one of (1) to (10), the polynucleotide according to (11) or (12), or the vector according to (13) and does not inhibit activin.
(17) A pharmaceutical composition, which comprises the polypeptide according to any one of (1) to (10), the polynucleotide according to (11) or (12), or the vector according to (13).
(18) An agent for increasing skeletal muscle, which comprises as an active ingredient the polypeptide according to any one of (1) to (10), the polynucleotide according to (11) or (12), or the vector according to (13).
(19) An agent for decreasing fat, which comprises as an active ingredient the polypeptide according to any one of (1) to (10), the polynucleotide according to (11) or (12), or the vector according to (13).
(20) A therapeutic agent or a prophylactic agent for amyotrophic symptoms, which comprises as an active ingredient the polypeptide according to any one of (1) to (10), the polynucleotide according to (11) or (12), or the vector according to (13).
(21) A therapeutic agent or a prophylactic agent for cachexia, disease accompanied by muscular atrophy, Type II diabetes, obesity, or acquired immunodeficiency syndrome, which comprises as an active ingredient the polypeptide according to any one of (1) to (10), the polynucleotide according to (11) or (12), or the vector according to (13).
(22) The therapeutic agent or the prophylactic agent according to (21), wherein the disease accompanied by muscular atrophy is hereditary muscular dystrophy, amyotrophic lateral sclerosis, spinocerebellar degeneration, or Parkinson's disease.
(23) A transgenic non-human mammal, into which a foreign gene containing the polynucleotide according to (11) or (12) is introduced.
(24) A method for increasing the muscle of a non-human animal, which comprises administering the polypeptide according to any one of (1) to (10), the polynucleotide according to (11) or (12), or the vector according to (13) to the non-human animal.
(25) A method for decreasing the fat of a non-human animal, which comprises administering the polypeptide according to any one of (1) to (10), the polynucleotide according to (11) or (12), or the vector according to (13) to the non-human animal.
(26) A method for assaying activity of a test substance to inhibit activin functions and GDF-8 functions, which comprises culturing a cell having a reporter plasmid in the presence of activin, GDF-8, activin and the test substance, or GDF-8 and the test substance and then performing reporter assay.
(27) The method according to (26), wherein luciferase is used as a reporter.
(28) The method according to (26) or (27), wherein a follistatin variant polypeptide (a) which comprises a follistatin domain I and (b) does not comprise an amino acid sequence that is represented by formula (I): Cys-$(X^1)_a$-Cys-$(X^2)_b$-Cys-$(X^3)_c$-Cys-$(X^4)_d$-Cys-$(X^5)_e$-Cys-$(X^6)_f$-Cys -$(X^7)_g$-Cys-$(X^8)_h$-Cys-$(X^9)_i$-Cys (SEQ ID NO: 30) wherein, $X^1$, $X^2$, $X^3$, $X^4$, $X^5$, $X^6$, $X^7$, $X^8$, and $X^9$ each independently represents the same or a different naturally occurring amino acid residue other than cysteine, "a" represents an integer between 2 and 6, "b" represents an integer between 3 and 7, "c" represents an integer between 7 and 11, "d" represents an integer between 0 and 4, "e" represents an integer between 1 and 6, "f" and "g" represent integers between 8 and 12, "h" represents an integer between 4 and 8, and "i" represents an integer between 11 and 15, and has 50% or more homology with the amino acid sequence of SEQ ID NO: 2 or SEQ ID NO: 29, is used as a test substance.

BRIEF DESCRIPTION OF THE DRAWINGS

FIG. 1 shows a comparison of the amino acid sequences of human (SEQ ID NO: 32), mouse (SEQ ID NO: 33), rat (SEQ ID NO: 34), cattle (SEQ ID NO: 35), pig (SEQ ID NO: 36), sheep (SEQ ID NO: 37), horse (SEQ ID NO: 38), and chicken (SEQ ID NO: 39) follistatins, and the consensus sequences of FSI and FSII (SEQ ID NOs: 1 and 2, respectively). Regions each separately corresponding to FSN, FSI, FSII, and FSIII domains are shown with upper lines, and the cysteine residues conserved in each follistatin domain are shown with dots.

FIG. 14 shows an amino acid sequence comparison of a mouse follistatin FSII domain (SEQ ID NO: 40) and a mouse FLRG FSII-like domain (SEQ ID NO: 29). Matched amino acids are indicated with "|."

BEST MODE OF CARRYING OUT THE INVENTION

Figure 2:
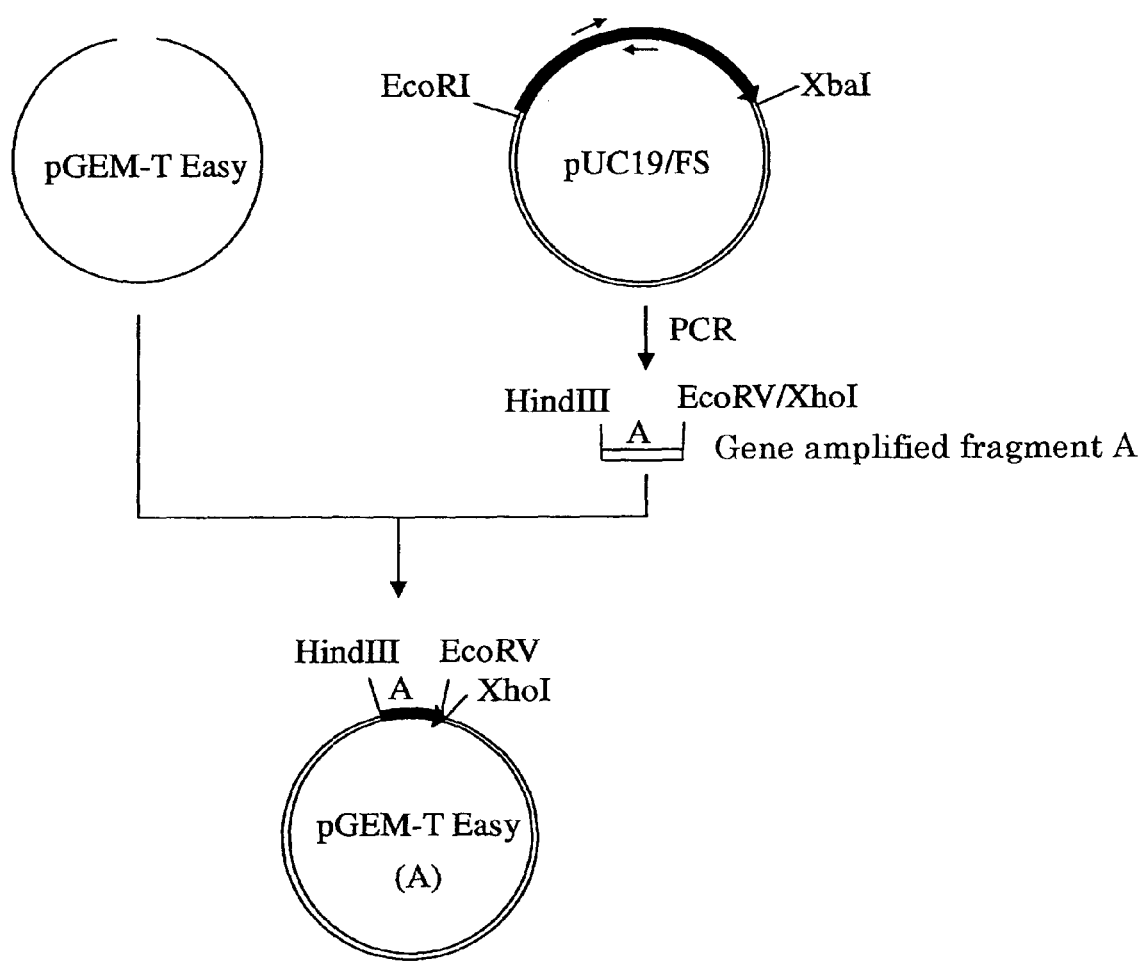
FIG. 2 shows construction steps for plasmid pGEM-T Easy (A).

1. Follistatin Variant Polypeptide of the Present Invention

The original follistatin used for preparing a variant in the present invention may be of any animal species. Follistatins of mammalian or avian, and specifically human, mouse, rat, cattle, pig, sheep, horse, chicken or the like are preferable. In particular, human follistatin is preferable. Furthermore, follistatin molecules may vary in their C-terminal amino acid sequences because of difference in mRNA splicing or post-translation processing, and any such follistatin molecules may be used. Specific examples of such follistatin include human follistatin comprising the amino acid sequence between the $30^{th}$ and the $344^{th}$ amino acids of SEQ ID NO: 4, mouse follistatin comprising the sequence between the $30^{th}$ and the $344^{th}$ amino acids of the amino acid sequence under accession No. P47931 of the NCBI protein database, mouse follistatin comprising the sequence between the $30^{th}$ and the $343^{rd}$ amino acids of the amino acid sequence under accession No. NP_032072 of the NCBI protein database, rat follistatin comprising the sequence between the $30^{th}$ and the $344^{th}$ amino acids of the amino acid sequence under accession No. P21674 of the NCBI protein database, cattle follistatin comprising the sequence between the $30^{th}$ and the $344^{th}$ amino acids of the amino acid sequence under accession No. P50291 of the NCBI protein database, pig follistatin comprising the sequence between the $30^{th}$ and the $344^{th}$ amino acids of the amino acid sequence under accession No. P10669 of the NCBI protein database, sheep follistatin comprising the sequence between the $30^{th}$ and the $344^{th}$ amino acids of the amino acid sequence under accession No. P31514 of the NCBI protein database, horse follistatin comprising the sequence between the $30^{th}$ and the $344^{th}$ amino acids of the amino acid sequence under accession No. 062650 of the NCBI protein database, chicken follistatin comprising the sequence between the $29^{th}$ and the $343^{rd}$ amino acids of the amino acid sequence under accession No. NP_990531 of the NCBI protein database, polypeptides comprising sequences derived from those of any of the above follistatins by deletion of 27 amino acids or 12 amino acids from the C-terminus, and naturally occurring polypeptides encoded by the genes of these polypeptides, which have experienced allele mutation or exhibit single nucleotide polymorphism.

In the present invention, a follistatin domain means a region containing 10 conserved cysteines that are repeated 3 times within follistatin and comprising the sequence of approximately 70 amino acids represented by Cys-(Xaa)$_4$-Cys-(Xaa)$_5$-Cys-(Xaa)$_{9-10}$-Cys-(Xaa)$_{1-2}$-Cys-(Xaa)$_3$-Cys-(Xaa)$_{9-10}$-Cys-(Xaa)$_{10}$-Cys-(Xaa)$_6$-Cys-(Xaa)$_{13}$-Cys (SEQ ID NO: 31) ("Xaa" indicates any amino acid sequence). From the N-terminal side, they are referred to as follistatin domain I (hereinafter, abbreviated as FSI), follistatin domain II (hereinafter, abbreviated as FSII), and follistatin domain III (hereinafter, abbreviated as FSIII). For example, in the amino acid sequence of a human follistatin precursor represented by SEQ ID NO: 4 (the nucleotide sequence encoding the amino acid sequence is shown in SEQ ID NO: 3), the region between the $95^{th}$ and the $164^{th}$ amino acids is FSI, the region between the $168^{th}$ and the $239^{th}$ amino acids is FSII, and the region between the $245^{th}$ and the $316^{th}$ amino acids is FSIII. Furthermore, the N-terminal domain (hereinafter, abbreviated as FSN) is a region between the N-terminus of follistatin and FSI, such as the region between the $30^{th}$ and the $94^{th}$ amino acids in the amino acid sequence of the human follistatin precursor represented by SEQ ID NO: 4. FIG. 1 shows the amino acid sequences of human, mouse, rat, cattle, pig, sheep, horse, and chicken follistatins, domain positions of FSN, FSI, FSII, and FSIII, and the consensus sequence of FSI and FSII.

The follistatin variant polypeptide of the present invention is a follistatin variant polypeptide that selectively inhibits GDF-8 activity as compared with its inhibition of activin activity, comprises FSI, and does not comprise the amino acid sequence that is represented by formula (I): Cys-(X$^1$)$_a$-Cys-(X$^2$)$_b$-Cys-(X$^3$)$_c$-Cys-(X$^4$)$_d$-Cys-(X$^5$)$_e$-Cys-(X$^6$)$_f$-Cys-(X$^7$)$_g$-Cys-(X$^8$)$_h$-Cys-(X$^9$)$_i$-Cys (SEQ ID NO: 30) (wherein, X$^1$, X$^2$, X$^3$, X$^4$, X$^5$, X$^6$, X$^7$, X$^8$, and X$^9$ each independently represents the same or a different naturally occurring amino acid residue other than cysteine, "a" represents an integer between 2 and 6, "b" represents an integer between 3 and 7, "c" represents an integer between 7 and 11, "d" represents an integer between 0 and 4, "e" represents an integer between 1 and 6, "f" and "g" represent integers between 8 and 12, "h" represents an integer between 4 and 8, and "i" represents an integer between 11 and 15) and has 50% or more, preferably 60% or more, more preferably 80% or more, and more preferably 95% or more homology (hereinafter, referred to as an FSII homologous sequence) with the amino acid sequence of SEQ ID NO: 2 or SEQ ID NO: 29. "Naturally occurring amino acid residue other than cysteine" means any one of the following amino acid residues: asparagine, aspartic acid, alanine, arginine, isoleucine, glutamine, glutamic acid, glycine, serine, threonine, tyrosine, tryptophan, histidine, valine, phenylalanine, proline, methionine, lysine, and leucine. The amino acid sequence of SEQ ID NO: 2 is the consensus amino acid sequence of mammalian follistatin FSII and chicken follistatin FSII. The amino acid sequence of SEQ ID NO: 29 is the second follistatin domain-like sequence among the two follistatin domain-like sequences of the FLRG protein encoded by a mouse follistatin related gene (FLRG) and has 61% homology with the sequence of SEQ ID NO: 2. Examples of FSII homologous sequence also include the amino acid sequence of SEQ ID NO: 2 and the amino acid sequence of SEQ ID NO: 29. Specific examples of the FSII homologous sequence include the amino acid sequence represented by the above formula (I) wherein $(X^1)_a$ is the amino acid sequence between amino acid positions 2 and 5 of SEQ ID NO: 2 or is the amino acid sequence between amino acid positions 2 and 5 of SEQ ID NO: 29, the same wherein $(X^2)_b$ is the amino acid sequence between amino acid positions 7 and 11 of SEQ ID NO: 2 or the amino acid sequence between amino acid positions 7 and 11 of SEQ ID NO: 29, the same wherein $(X^3)_c$ is the amino acid sequence between amino acid positions 13 and 21 of SEQ ID NO: 2 or the amino acid sequence between amino acid positions 13 and 21 of SEQ ID NO: 29, the same wherein $(X^4)_d$ is the amino acid sequence between amino acid positions 23 and 24 of SEQ ID NO: 2 or the amino acid sequence between amino acid positions 23 and 24 of SEQ ID NO: 29, the same wherein $(X^5)_e$ is the amino acid sequence between amino acid positions 26 and 28 of SEQ ID NO: 2 or the amino acid sequence between amino acid positions 26 and 29 of SEQ ID NO: 29, the same wherein $(X^6)_f$ is the amino acid sequence between amino acid positions 30 and 39 of SEQ ID NO: 2 or the amino acid sequence between amino acid positions 31 and 40 of SEQ ID NO: 29, the same wherein $(X^7)_g$ is the amino acid sequence between amino acids 41 and 50 of SEQ ID NO: 2 or the amino acid sequence between amino acid positions 42 and 51 of SEQ ID NO: 29, the same wherein $(X^8)_h$ is the amino acid sequence between amino acid positions 52 and 57 of SEQ ID NO: 2 or the amino acid sequence between amino acid positions 53 and 58 of SEQ ID NO: 29, and the same wherein $(X^9)_i$ is the amino acid sequence between amino acid positions 59 and 71 of SEQ ID NO: 2 or the amino acid sequence between amino acid positions 60 and 72 of SEQ ID NO: 29.

Examples of a follistatin variant that is a sequence which does not comprise a sequence FSII homologous sequence include a variant obtained through deletion of the entire FSII, a variant obtained through deletion of a partial region containing one or more cysteine residues of FSII, a variant obtained through deletion of one or more cysteine residues of FSII or substitution of the same with (an)other amino acids, and a variant obtained through insertion of an amino acid sequence containing no FSII homologous sequence and comprising 10 or more amino acids into FSII. Regarding amino acid sequences of domains other than FSI and FSII, the position and the number of amino acids that are deleted, added, or substituted are not limited, as long as the relevant sequence comprises FSI and does not comprise FSII homologous sequence. The number of amino acids to be mutated (specifically, the number of amino acids to be deleted, added, or substituted) preferably ranges from 1 to 50, more preferably 1 to 30, further preferably 1 to 20, further preferably 1 to 10, and particularly preferably 1 to 5. Moreover, as long as a follistatin variant polypeptide can selectively inhibit GDF-8 activity as compared with its inhibition of activin activity, deletion, addition, or substitution of amino acid may be present also in an FSI amino acid sequence. The number of amino acids to be mutated in such FSI amino acid sequence is preferably 1 to 10, more preferably 1 to 8, and further preferably 1 to 5. It is preferable that FSIII has been further deleted from the follistatin variant polypeptide of the present invention. Moreover, the number of FSI may be 1. Preferably, the follistatin variant polypeptide comprises 2 or more FSIs. The follistatin variant polypeptide may comprise FSN.

Examples of the follistatin variant polypeptide of the present invention include polypeptides having domain structures such as FSI, FSI-FSI, FSI-FSI-FSIII, FSN-FSI, FSN-FSI-FSI or FSN-FSI-FSI-FSIII, and polypeptides obtained by fusing other polypeptides to the N-termini or the C-termini of these polypeptides. The domains are directly linked or linked via a linker polypeptide comprising 1 to 50, preferably 1 to 10, and more preferably 1 to 5 amino acids. The amino acid sequence of the linker polypeptide may be any sequence, as long as it contains no cysteines. A polypeptide sequence to be fused to the N-terminus or the C-terminus may be any sequence or a single amino acid, as long as it contains no FSII homologous sequence described above. Examples of such polypeptide to be fused to the N-terminus or the C-terminus include an immunoglobulin constant region, protein A, protein G, green fluorescent protein, β-galactosidase, chloramphenicol acetyltransferase, maltose binding protein, glutathione-S-transferase, thioredoxin, polyhistidine, S peptide, FLAG peptide, HA epitope peptide, and myc epitope peptide.

Examples of FSI sequences include the amino acid sequence between the 95$^{th}$ and the 164$^{th}$ amino acids of SEQ ID NO: 4 and the amino acid sequence of SEQ ID NO: 1, which is the FSI consensus sequence of mammalian and chicken follistatins. Examples of FSII sequences include the amino acid sequence between the 168$^{th}$ and the 239$^{th}$ amino acids of SEQ ID NO: 4 and the amino acid sequence of SEQ ID NO: 2, which is the FSII consensus sequence of mammalian and chicken follistatins. An example of an FSN sequence is the amino acid sequence between the 1$^{st}$ and the 94$^{th}$ amino acids of SEQ ID NO: 4. An example of an FSIII sequence is the amino acid sequence between the 245$^{th}$ and the 316$^{th}$ amino acids of SEQ ID NO: 4.

Specific examples of the follistatin variant polypeptide of the present invention include polypeptides comprising the amino acid sequences of SEQ ID NOS: 6, 8, and 10.

The follistatin variant polypeptide of the present invention may be a modified polypeptide. The term "modification" used in the present invention must be most broadly interpreted as including chemical modification and biological modification. Examples of such modification include, but are not limited to, functional group introduction such as alkylation, esterification, halogenation, and amination, functional group conversion such as oxidation, reduction, addition, and elimination, introduction of a sugar compound (monosaccharide, disaccharide, oligosaccharide, or polysaccharide), a lipid compound, or the like, phosphorylation, biotinylation, and modification with polyethylene glycol.

The above-described polypeptide of the present invention may be in a free state and may be provided as an acid addition salt or a base addition salt. Examples of an acid addition salt include: mineral acid salts such as hydrochloride, sulfate, nitrate, and phosphate; and organic acid salts such as p-toluenesulfonate, methanesulfonate, citrate, oxalate, maleate, and tartrate. Examples of a base addition salt include: metal salts such as a sodium salt, a potassium salt, a calcium salt, and a magnesium salt; ammonium salts; and organic ammonium salts such as a methyl ammonium salt and a triethyl ammonium salt. The polypeptide of the present invention may form a salt with an amino acid such as glycine, or may form a counter ion within the molecule.

Furthermore, these polypeptides or salts thereof may be present as hydrates or solvates. The polypeptide of the present invention has a plurality of asymmetric carbons. The steric configuration of each asymmetric carbon is not particularly limited, but amino acid residues are preferably L-amino acids. Optically active substances based on these asymmetric carbons, stereoisomers such as diastereoisomers, and an arbitrary mixture of stereoisomers, racemic bodies, and the like are all included within the scope of the present invention.

A method for producing the follistatin variant of the present invention, a method for evaluating activity, and a method of using the follistatin variant will be described as follows.

2. Method for Producing Follistatin Variant Polypeptide (1) Construction of DNA Encoding Follistatin Variant Polypeptide The structure of the follistatin variant polypeptide that selectively inhibits GDF-8 as compared with its inhibition of activin activity is designed based on the conditions described in 1. DNA encoding the polypeptide is constructed as follows.

First, DNAs encoding partial fragments that contain follistatin regions required for composing the entirety of follistatin or a designed follistatin variant polypeptide are obtained. The nucleotide sequences of various mammalian and chicken follistatin cDNAs or genomic DNAs are known. Hence, PCR is performed using primers obtained based on the sequence information and using template cDNAs isolated from testis of various mammalian and chicken. Arbitrary partial fragments of such mammalian or chicken follistatin cDNAs can thus be obtained. Furthermore, follistatin cDNA is cloned through screening of a testis cDNA library, and the cDNA may be used as a template. Examples of the nucleotide sequences of various mammalian and chicken follistatin cDNAs or genomic DNAs include the nucleotide sequences described under NCBI nucleotide database accession Nos. NM_013409 (human follistatin cDNA), NM_008046 (mouse follistatin cDNA), NM_012561 (rat follistatin cDNA), NM_175801 (cattle follistatin cDNA), M63123 (sheep follistatin cDNA), AB010829 (cattle follistatin cDNA), M19529 (pig follistatin genomic DNA), NM_205200 (chicken follistatin cDNA), and the like. DNA containing a sequence complementary to a 15- to 30-nucleotide sequence on the 5' end of a region to be obtained and a sequence complementary to a 15- to 30-nucleotide sequence on the 3'end of the same is synthesized, and then the sequences are used as primers. It is preferable to previously add recognition sequences for appropriate restriction enzymes to the 5' ends of both primers in PCR for use in ligation of partial fragments or insertion into a vector. cDNA preparation and PCR can be performed according to the description in experimental protocols such as Sambrook, J. and Russel, D. W., Molecular Cloning: A Laboratory Manual, 3rd ed., Cold Spring Harbor Laboratory Press (2001). If necessary, similar procedures may be performed using the thus obtained DNA as a template, so that partial fragments of the DNA encoding regions required for composing the designed follistatin variant polypeptide may be obtained.

Based on the structure of the designed follistatin variant polypeptide, each obtained partial fragment is ligated to fit the frame. If necessary, such partial fragment is ligated to DNA encoding another polypeptide, a termination codon is added to the 3' end of the coding region, or mutation is introduced. Hence, DNA encoding the follistatin variant polypeptide can be constructed.

As described in (3), when transformed cells are cultured and then the follistatin variant polypeptide is secreted extracellularly, a DNA is constructed, which encodes a polypeptide wherein a signal peptide existing on the N-terminus of a precursor of a secretory protein is added to the N-terminus of the designed follistatin variant polypeptide. As such signal peptide, a follistatin signal peptide can be used, for example. The DNA encoding such follistatin signal peptide can be obtained by amplifying a fragment that contains a follistatin signal peptide upon obtainment of a DNA encoding a follistatin fragment containing FSI required for composing the above follistatin variant polypeptide.

When follistatin variant polypeptide is not secreted and when the N-terminus of the designed follistatin variant polypeptide is not methionine, an initiation codon (atg) is added before the region encoding such follistatin variant polypeptide.

For example, when a follistatin variant polypeptide having a domain structure of FSN-FSI-FSI is secreted, first, a partial fragment A of a follistatin cDNA encoding a region that contains signal peptide-FSN-FSI and a partial fragment B of a follistatin cDNA encoding a region containing FSI are each obtained by PCR. Through ligation of the thus obtained cDNA fragment B downstream of the thus obtained cDNA fragment A, a DNA encoding the follistatin variant polypeptide having the domain structure of signal peptide-FSN-FSI-FSI can be prepared.

Furthermore, when a follistatin variant polypeptide having the domain structure of FSN-FSI-FSI-FSIII is secreted, a follistatin cDNA partial fragment C encoding a region that contains FSIII is obtained by PCR. The cDNA fragment B is ligated downstream of the above cDNA fragment A, and then the cDNA fragment C is further ligated downstream of the resultant. Thus a DNA encoding the follistatin variant polypeptide having the domain structure of signal peptide-FSN-FSI-FSI-FSIII can be prepared.

(2) Construction of Follistatin Variant Expression Vector and Introduction of the Vector into Host Cell The DNA encoding the follistatin variant polypeptide prepared in (1) is inserted into an expression vector appropriate for a host cell, so that a follistatin variant expression vector is constructed.

As host cells, any prokaryotes such as bacteria, eukaryotic microorganisms such as yeast, animal cells, insect cells, plant cells, or the like can be used, as long as they can express follistatin variant polypeptides. For a follistatin variant polypeptide that is expressed by cells (hereinafter, also referred to as transformed cells) wherein a follistatin variant expression vector has been introduced to be able to keep its normal higher order structure and to retain its GDF-8-specific inhibition activity, the polypeptide is preferably expressed by animal cells, insect cells, or the like.

As an expression vector for insertion of a DNA encoding the follistatin variant polypeptide, a vector that is autonomously replicable in the above host cells or can be incorporated into a chromosome, and contains a promoter that is functional in host cells can be used. Furthermore, for construction of a vector using *Escherichia coli*, it is preferred that the vector contains a drug-resistance gene containing an endogenous promoter for *Escherichia coli* and a replication origin required for replication within *Escherichia coli*. Examples of such drug-resistance gene for *Escherichia coli* include an ampicillin-resistance gene (β-lactamase gene) derived from *Escherichia coli*, tetracycline-resistance gene, and a kanamycin-resistance gene. Examples of a replication origin required for replication in *Escherichia coli* include a pBR322 replication origin and a colE1 replication origin.

When a host cell is an animal cell, an example of an expression vector for insertion of a DNA encoding the follistatin variant polypeptide is a plasmid having a promoter that is functional in such animal cell and a polyadenylation signal.

Any promoter that is functional in animal cells can be used. Examples of such promoter include an IE (immediate early) gene promoter of human cytomegalovirus (CMV), an SV40 early promoter, a long terminal repeat (LTR) of Moloney mouse leukemia virus, LTR of Rous sarcoma virus, a thymidine kinase (TK) gene promoter of simple herpes virus (HSV), a retrovirus promoter, a heat shock promoter, an SRα promoter, and a metallothionein promoter. With the above promoter, an IE gene enhancer of human CMV can also be used, for example. Preferably, a promoter has an appropriate restriction enzyme site downstream of which a DNA encoding the follistatin variant polypeptide can be inserted.

As a polyadenylation signal, any polyadenylation signal can also be used. For example, a polyadenylation signal of an SV40 early gene, a polyadenylation signal of a rabbit β globin gene, a polyadenylation signal of a bovine growth hormone gene, and the like can be used.

Furthermore, an expression vector to be used herein may further have an expression unit (structure wherein a drug-resistance gene and a polyadenylation signal are ligated in turn downstream of a promoter) of a drug-resistance gene for animal cells. Examples of such drug-resistance gene for animal cells include a neomycin-resistance gene, a hygromycin-resistance gene, a blasticidin-resistance gene, a puromycin-resistance gene, and a Zeocin-resistance gene. The above-described promoters and polyadenylation signals can be used. When an expression vector having an expression unit of a drug-resistance gene is used, transformed cells that can perform expression non-transiently and stably can be obtained by culturing transformed cells in the presence of the drug.

With the use of an expression vector containing an expression unit of a dihydrofolate reductase (dhfr) gene and animal cells deficient in the dhfr gene as host cells, transformed cells are cultured in the presence of methotrexate. Methotrexate concentration is elevated stepwise under such conditions, so as to amplify the copy number of a DNA encoding the follistatin variant polypeptide, which has been introduced together with the dhfr gene. Thus, transformed cells with high expression levels of the follistatin variant polypeptide can be obtained.

Furthermore, an expression vector to be used herein may also have a replication origin required for replication in animal cells. As such replication origin, the SV40 replication origin or replication origin oriP of the Epstein-Barr virus can be used. A plasmid vector having the SV40 replication origin is suitable for the expression of a target gene at a high level, because the copy number in host cells expressing an SV40 large T antigen is increased. A vector containing oriP is maintained outside the host's chromosome without being incorporated by the chromosome in the host expressing EBNA-1 (Epstein-Barr virus nuclear antigen-1) of Epstein-Barr virus.

Examples of the above-described expression vectors for animal cells include pcDNA3 (produced by Invitrogen), pcDNA3.1(+) (produced by Invitrogen), pSI (produced by QIAGEN), pCI-neo (produced by QIAGEN), pAGE107, pAGE103, and pAMo (J. Biol. Chem., 268, 22782 (1993)).

The DNA encoding the follistatin variant polypeptide prepared in (1) is inserted downstream of the promoter of the above expression vector for animal cells, so that an expression vector for the follistatin variant polypeptide is constructed.

Examples of host cells include cells of monkey kidney cell lines COS-1 (ATCC NO: CRL-1650) and COS-7 (ATCC NO: CRL-1651), Chinese hamster ovary cell lines CHO-K1 (ATCC NO: CCL-61) and CHO/dhFr- (ATCC NO: CRL-9096), human B lymphocyte cell line Namalwa (ATCC NO: CRL-1432), human kidney cell line HEK293 (ATCC NO: CRL-1573), human cervix epithelial cell line HeLa (ATCC NO: CCL-2), and mouse embryo cell line NIH/3T3 (ATCC NO: CRL-1658), for example.

Any method for introducing a recombination vector can be employed, as long as it is a method for introducing DNA into animal cells. Examples of such method include an electroporation method (Cytotechnology, 3, 133 (1990)), a calcium phosphate method (JP Patent Publication (Kokai) No. 2-227075 A (1990)), a lipofection method (Proc. Natl. Acad. Sci. U.S.A., 84, 7413 (1987)), and a method described in Virology, 52, 456 (1973). Furthermore, a commercial DNA transfection reagent can also be used. Examples of such DNA transfection reagent include TransFast (produced by Promega), Lipofectamine 2000 (produced by Invitrogen), SuperFect (produced by QIAGEN), and PolyFect (produced by QIAGEN).

When insect cells are used as hosts, insect cells that express the follistatin variant polypeptide can be obtained by a method described in Baculovirus Expression Vectors, A Laboratory Manual, W. H. Freeman and Company, New York (1992); Molecular Cloning: A Laboratory Manual, 3rd ed., Cold Spring Harbor Laboratory Press (2001); or Bio/Technology, 6, 47 (1988), for example.

Specifically, a recombination gene transfer vector and baculovirus are together introduced into insect cells so as to obtain recombinant virus in the culture supernatant of the insect cells. Insect cells are further infected with the recombinant virus, so that insect cells expressing the polypeptide can be obtained.

Examples of such gene transfer vector that is used in the method include pVL1392, pVL1393 (both produced by Pharmingen), and pBlueBac4.5 (produced by Invitrogen).

As a baculovirus, the *Autographa californica* nuclear polyhedrosis virus that infects insects of the family Noctuidae, for example can be used.

Examples of insect cells include cell lines such as Sf9 and Sf21 derived from *Spodoptera frugiperda* (produced by Invitrogen), High 5 derived from *Trichoplusia ni* (produced by Invitrogen), and Bm5 (produced by Invitrogen) and N4 derived from silkworm (*Bombyx mori*).

Examples of a method for introducing together a transfer vector and the above baculovirus for preparation of a recombinant virus include a calcium phosphate method (JP Patent Publication (Kokai) No. 2-227075 A (1990)) and a lipofection method (Proc. Natl. Acad. Sci. U.S.A., 84, 7413 (1987)).

When prokaryotes such as bacteria are used as host cells, an expression vector to be used herein is autonomously replicable in a host prokaryote and has a promoter, a ribosome binding sequence located downstream of the promoter, and a cloning site into which a DNA encoding the follistatin variant polypeptide is inserted. It is preferable, but is not always required, that a transcription termination sequence be located immediately following the cloning site. Furthermore, for selection of a transformant, the vector further contains a sequence that expresses a gene that serves as a marker, such as a drug-resistance gene. A DNA encoding a follistatin variant polypeptide is inserted at the cloning site located downstream of a ribosome binding sequence. The distance between a ribosome binding sequence and an initiation codon is preferably regulated to be an appropriate length (e.g., 6 to 18 nucleotides when a vector is used with an *Escherichia coli* host).

Any promoter can be used, as long as it can be expressed in host cells. For example, when *Escherichia coli* is used as a host, examples of promoters include those derived from

*Escherichia coli*, phages, or the like such as a trp promoter, a lac promoter, a PL promoter, a T7 promoter, and a PR promoter. Furthermore, artificially designed and altered promoters such as two trp promoters that are serially arrayed, a tac promoter, a T7lac promoter, and a letI promoter, can also be used, for example. When *Bacillus subtilis* is used as a host, examples of promoters include promoters of SPO1, SPO2, and PenP, which are phages of *Bacillus subtilis*.

Examples of expression vectors include pGEMEX-1 (produced by Promega), pQE-30 (produced by QIAGEN), pKYP200 (Agric. Biol. Chem., 48, 669 (1984)), pLSA1 (Agric. Biol. Chem., 53, 277 (1989)), pGEL1 (Proc. Natl. Acad. Sci., U.S.A., 82, 4306 (1985)), pTrS30 (prepared from *Escherichia coli* JM109/pTrS30 (FERM BP-5407)), pGEX-5X-3 (produced by Amersham Biosciences), pET14 (produced by Novagen), pPROTet.E (produced by Clontech), and pRSET A (produced by Invitrogen).

Examples of host cells include microorganisms belonging to the genus *Escherichia*, the genus *Serratia*, the genus *Bacillus*, the genus *Brevibacterium*, the genus *Corynebacterium*, the genus *Microbacterium*, and the genus *Pseudomonas*, such as *Escherichia coli* XL1-Blue, *Escherichia coli* XL2-Blue, *Escherichia coli* DH1, *Escherichia coli* MC1000, *Escherichia coli* KY3276, *Escherichia coli* W1485, *Escherichia coli* JM109, *Escherichia coli* HB101, *Escherichia coli* No. 49, *Escherichia coli* W3110, *Escherichia coli* NY49, *Escherichia coli* BL21 (DE3) pLysS, *Serratia ficaria*, *Serratia fonticola*, *Serratia liquefaciens*, *Serratia marcescens*, *Bacillus subtilis*, *Bacillus amyloliquefaciens*, *Brevibacterium ammoniagenes*, *Brevibacterium immariophilum* ATCC14068, *Brevibacterium saccharolyticum* ATCC14066, *Corynebacterium glutamicum* ATCC13032, *Corynebacterium glutamicum* ATCC14067, *Corynebacterium glutamicum* ATCC13869, *Corynebacterium acetoacidophilum* ATCC13870, *Microbacterium ammoniaphilum* ATCC15354, and *Pseudomonas* sp. D-0110.

Any method for introducing a recombination vector can be used, as long as it is a method for introducing DNA into the above host cells. Examples of such method include an electroporation method (Nucleic Acids Res., 16, 6127 (1988)), a method using calcium ions (Proc. Natl. Acad. Sci. U.S.A., 69, 2110 (1972); Gene, 17, 107 (1982)), and a protoplast method (JP Patent Publication (Kokai) No. 63-248394 A (1988); Mol. Gen. Genet., 168, 111 (1979)).

An expression vector that is used when yeast is used as a host cell contains a promoter that serves for transcription in host yeast, a transcription termination sequence, and a gene that serves as a transformation marker in yeast, such as a sequence capable of expressing a drug-resistance gene or a gene of an amino acid synthesis system (e.g., TRP1, HIS3, or LEU2). Moreover, to facilitate construction or maintenance of an expression vector, the vector that is used herein is preferably autonomously replicable in *Escherichia coli* and can express a drug-resistance gene that serves as a gene transfer marker.

Any promoter may be used, as long as it can serve for transcription in yeast. Examples of such promoter that is used herein include a *Saccharomyces cerevisiae* alcohol dehydrogenase gene ADH1, galactose metabolic system gene GAL1 and GAL10 promoters, an acid phosphatase gene PHO5 promoter, a phosphoglycerate kinase gene PGK promoter, a glyceraldehyde-3-phosphate dehydrogenase gene GAP promoter, a heat shock protein gene promoter, an α conjugon gene MFα1 promoter, a copper-metallothionein gene CUP1 promoter, and a *Pichia pastoris* alcohol oxidase gene AOX1 promoter.

Examples of host cells include cells of yeast strains belonging to the genus *Saccharomyces*, the genus *Schizosaccharomyces*, the genus *Pichia*, and the like. Specific examples of such host cells include cells of *Saccharomyces cerevisiae*, *Schizosaccharomyces pombe*, and *Pichia pastoris*.

Any method for introducing a recombination vector can be used, as long as it is a method for introducing DNA into yeast. Examples of such method include an electroporation method (Methods Enzymol., 194, 182 (1991)), a spheroplast method (Proc. Natl. Acad. Sci. U.S.A., 81, 4889 (1984)), and a lithium acetate method (J. Bacteriol., 153, 163 (1983)).

(3) Culture of Transformed Cell and Purification of Follistatin Variant Polypeptide When the transformed cells prepared in (2) are prokaryotes such as *Escherichia coli* or eukaryotes such as yeast, a medium that may be used for culturing the cells may be either a natural or synthetic medium, as long as it contains a carbon source which are assimilable by the cells, a nitrogen source, inorganic salts, and the like, and enables efficient culture of transformants. A carbon source that can be used herein may be a source that is assimilable by the relevant organism. Examples of such carbon source include glucose, fructose, sucrose, molasses containing the same, carbohydrates such as starch or starch hydrolysate, organic acids such as acetic acid and propionic acid, and alcohols such as ethanol and propanol. As nitrogen sources, ammonia, and inorganic acid or organic acid ammonium salts such as ammonium chloride, ammonium sulfate, ammonium acetate, and ammonium phosphate, and other nitrogen-containing compounds can be used. Furthermore, as nitrogen sources, peptone, a meat extract, a yeast extract, corn steep liquor, a casein hydrolysate, soybean cake and a soybean cake hydrolysate, various fermentation microbial bodies, digests thereof, and the like can be used. As inorganic salts, dipotassium hydrogen phosphate, potassium dihydrogenphosphate, magnesium phosphate, magnesium sulfate, sodium chloride, ferrous sulfate, manganese sulfate, copper sulfate, calcium carbonate, and the like can be used.

Culture is performed generally under aerobic conditions such as those of shake culture or submerged aeration and agitation culture. Temperature for culture preferably ranges from 15° C. to 40° C. The culture period is generally between 16 and 96 hours. pH is maintained between 3.0 and 9.0 during culture. pH adjustment is performed using inorganic or organic acid, an alkaline solution, urea, calcium carbonate, ammonia, or the like. If necessary, antibiotics such as ampicillin and tetracycline may be added to a medium during a culture period. When a microorganism that has been transformed with an expression vector having an inducible promoter used therein is cultured, an inducer may be added to a medium, if necessary. For example, when a microorganism that has been transformed with an expression vector having an lac promoter used therein is cultured, isopropylthiogalactoside (IPTG) or the like may be added to a medium. When a microorganism that has been transformed with an expression vector having a trp promoter used therein is cultured, indoleacrylic acid or the like may be added to a medium.

When transformed cells prepared in (2) are animal cells, a generally used RPMI 1640 medium (J. Am. Med. Assoc., 199, 519 (1967)), an Eagle MEM medium (Science, 122, 501 (1952)), Dulbecco's modified eagle medium (Virology, 8, 396 (1959)), a 199 medium (Proc. Soc. Exp. Biol. Med., 73, 1 (1950)), a MEM medium, an EX-CELL 301 medium (produced by JRH Biosciences), or media prepared by adding fetal calf serum or the like to these media can be used as media for culturing the cells, for example. Culture is generally performed under conditions of pH 6 to 8 and 30° C. to 40° C. in the presence of 5% $CO_2$, and the like for 1 to 7 days. During culture, antibiotics such as kanamycin and penicillin may also be added, if necessary.

When transformed cells prepared in (2) are insect cells, as a medium for culturing the cells, a TNM-FH medium (produced by Pharmingen), Sf-900 II SFM medium (produced by Invitrogen), EX-CELL 400, EX-CELL 405 (produced by JRH Biosciences), Grace's insect medium (Nature, 195, 788 (1962)), and the like that are generally used can be used. Preferable culture conditions comprise pH 6 to 7, culture temperature ranging from 25° C. to 30° C., and culture time generally ranging from 1 to 5 days. Moreover, antibiotics such as gentamicin may be added to a medium during culture, if necessary.

The follistatin variant polypeptide may be secreted outside the cells or may be expressed within the cells without being secreted. Preferably, the follistatin variant polypeptide is secreted outside the cells. When the follistatin variant polypeptide is secreted outside the cells, an expression vector is constructed using a DNA (as a DNA encoding the follistatin variant polypeptide in (2)) that encodes a polypeptide wherein a signal peptide has been added to the N-terminus of the designed follistatin variant polypeptide, and then transformed cells are obtained. Upon secretion, the signal peptide is cleaved. Hence, the follistatin variant polypeptide from which the signal peptide has been removed is accumulated in the medium.

Through culture of cells as described above, the expressed follistatin variant polypeptide is accumulated in the medium wherein the transformed cells have been cultured or in the transformed cells. The follistatin variant polypeptide can be isolated and purified from the medium or the transformed cells as described below.

When the follistatin variant polypeptide is secreted outside the cells, the medium is harvested. When transformed cells are free-floating, the medium is subjected to centrifugation or filtration, so as to separate the medium from the cells, and then the medium is harvested. From the thus harvested medium, the follistatin variant polypeptide can be efficiently purified by affinity chromatography using a sulfated cellulofine column. Furthermore, purification methods that are generally employed for protein purification, such as gel filtration, ion exchange chromatography, reverse phase column chromatography, ultrafiltration, and the like are performed in combination, so that the follistatin variant polypeptide can be purified. Moreover, the follistatin variant polypeptide can also be purified by affinity chromatography using an antibody that specifically recognizes follistatin FSI.

Furthermore, when the follistatin variant polypeptide is a fusion protein with another polypeptide, such follistatin variant polypeptide can also be purified by affinity chromatography using a substance that specifically binds to the other polypeptide that has been fused to form such fusion protein. The follistatin variant polypeptide can be purified by affinity chromatography using: a column to which protein A or an anti-IgG antibody has been immobilized when such fusion protein is formed with an IgG constant region; a column to which IgG has been immobilized when such fusion protein is formed with protein A; a column to which an antibody against the following peptide has been immobilized when such fusion protein is formed with FLAG peptide, S peptide, HA epitope peptide, or myc epitope peptide; a column to which nickel ions have been immobilized when such fusion protein is formed with polyhistidine; or a column to which glutathione has been immobilized when such fusion protein is formed with glutathione-S-transferase.

When the follistatin variant polypeptide is expressed within cells, the transformed cells are harvested. The thus harvested cells are disrupted by a homogenizer, ultrasonication, or the like in an appropriate buffer containing a protease inhibitor. Subsequently, the supernatant is collected by centrifugation, so that a cell lysis solution is obtained. From the thus obtained cell lysis solution, the follistatin variant polypeptide can be isolated and purified by techniques similar to methods for isolation and purification from media.

Furthermore, according to known methods (J. Biomolecular NMR, 6, 129, Science, 242, 1162 (1988); J. Biochem., 110, 166 (1991)), the follistatin variant polypeptide can also be produced using in vitro transcription and translation systems.

The molecular amount of a purified follistatin variant can be measured by SDS-polyacrylamide gel electrophoresis (SDS-PAGE; Nature, 227, 680 (1970)) or a Western blotting method (Antibodies: A Laboratory Manual, Cold Spring Harbor Laboratory, Chapter 12 (1988), Monoclonal Antibodies: Principles and Practice, Academic Press Limited (1996)); or the like.

3. Confirmation of Selective Inhibition of GDF-8 by the Follistatin Variant of the Present Invention That the follistatin variant polypeptide of the present invention "selectively inhibits GDF-8 activity" means that it "selectively inhibits GDF-8 activity as compared with its inhibition of activin activity." The phrase "selectively inhibits GDF-8 activity as compared with its inhibition of activin activity" means that, according to the method described in claim 3, when the inhibition of activin activity by the follistatin variant polypeptide and the inhibition of GDF-8 activity by the same polypeptide having the same concentration as the former polypeptide are measured, whereas the follistatin variant polypeptide inhibits GDF-8 activity by 50% or more, preferably 60% or more, more preferably 70% or more, and further preferably 80% or more, the follistatin variant polypeptide inhibits activin activity by less than 50%, preferably 30% or less, and more preferably 10% or less, and further preferably does not inhibit activin activity; that is, the follistatin variant polypeptide inhibits GDF-8 activity more strongly than it inhibits activin activity.

The follistatin variant polypeptide of the present invention is a follistatin variant polypeptide that selectively inhibits GDF-8 activity as compared with its inhibition of activin activity. Preferably, the follistatin variant polypeptide selectively inhibits GDF-8 activity without inhibiting activin activity. As described below, the activity of the follistatin variant polypeptide of the present invention (activity of selectively inhibiting GDF-8 activity as compared with its inhibition of activin activity) can be confirmed through measurement of the transcription-promoting activity of activin and the same of GDF-8 using reporter assay, for example.

Animal cells are prepared, into which a reporter plasmid $(CAGA)_{12}$-MLP-Luc (EMBO J., 17, 3091 (1998)) has been introduced. $(CAGA)_{12}$-MLP-Luc has a structure wherein an adenovirus major late promoter is present, upstream of which 12 response sequences (each consisting of AGCCAGACA and referred to as a CAGA box) to activin and GDF-8 have been inserted, and downstream of which a firefly luciferase gene has been ligated as a reporter gene. Such reporter plasmid can be introduced by the method described in 2. Luciferase activity is measured when (a) GDF-8, (b) activin, (c) the follistatin variant polypeptide, (d) GDF-8 and the follistatin variant polypeptide, (e) activin and the follistatin variant polypeptide, and (f) no substances are each added to the thus obtained transformed cells. The transformed cells are transcriptionally activated to lead to elevated luciferase activity in the cases of addition of (a) GDF-8 and (b) activin, unlike the case of (f) no addition. Furthermore, no elevated luciferase activity is observed in the case of addition of (c) the follistatin variant polypeptide. That the follistatin variant polypeptide of the present invention selectively inhibits GDF-8 activity can be confirmed by: (I) the fact that luciferase activity is lowered in the case of addition of (d) GDF-8 and the follistatin variant polypeptide, as compared with the case of addition of (a) GDF-8, and the resulting luciferase activity becomes close to the level of luciferase activity observed in the case of addition of (c) the follistatin variant polypeptide alone or (e) no addition; while (II) as compared with the case of addition of (a) activin, lowered luciferase activity is not observed in the case of addition of (d) activin and the follistatin variant polypeptide, or the degree of lowered luciferase activity is clearly weaker than that of lowered luciferase activity in the case of addition of GDF-8.

4. Pharmaceutical Composition Comprising Follistatin Variant Polypeptide of the Present Invention The follistatin variant polypeptide of the present invention, a polynucleotide encoding the polypeptide for the expression of the polypeptide within a living body to which the polypeptide is administered, and a vector comprising the polynucleotide selectively inhibit GDF-8 activity as compared with their inhibition of activin activity. Hence, they can be used for treating or preventing symptoms or diseases where GDF-8 is associated with the onset or progress thereof. Moreover, fewer side effects due to inhibition of activin are expected. Examples of such symptoms and diseases include: diseases, aging, the condition of being confined to bed, or the like, accompanied by decreases in or muscular atrophy of skeletal muscle; increases in fat such as subcutaneous fat and visceral fat; cachexia; diseases accompanied by muscular atrophy; Type II diabetes; obesity; and acquired immunodeficiency syndrome. Examples of diseases accompanied by muscular atrophy include hereditary muscular dystrophy such as Duchenne muscular dystrophy and diseases through which muscular atrophy is secondarily developed due to neurodegeneration such as amyotrophic lateral sclerosis, spinocerebellar degeneration, and Parkinson's disease.

The follistatin variant polypeptide of the present invention, a polynucleotide encoding the polypeptide for the expression of the polypeptide within a living body to which the polypeptide is administered, or a vector containing the polynucleotide can be used alone as an agent for selectively inhibiting GDF-8, an agent for increasing skeletal muscle, an agent for decreasing fat, a therapeutic agent or a prophylactic agent for amyotrophic symptoms, or a therapeutic agent or a prophylactic agent for cachexia, disease accompanied by muscular atrophy, Type II diabetes, obesity, or acquired immunodeficiency syndrome. In general, it is preferable to provide them in the forms of various pharmaceutical preparations. Furthermore, these pharmaceutical preparations are used for animals or humans.

A pharmaceutical preparation relating to the present invention can contain the above active ingredient or a pharmacologically acceptable salt alone or can contain a mixture of such ingredient with any active ingredient for another therapy. Furthermore, such pharmaceutical preparation is produced by an any method that is known in the technical field of pharmaceutics, specifically by mixing an active ingredient with one or more types of pharmacologically acceptable carrier.

The route of administration that is most effective for prevention or treatment is preferably used. Examples of such route of administration include oral administration and parenteral administration such as intravenous administration. Parenteral administration is preferable.

Examples of forms of administration include tablets and injections.

Tablets that are appropriate for oral administration, for example, can be produced using, as additives, an excipient such as lactose or mannite, a disintegrating agent such as starch, a lubricant such as magnesium stearate, a binder such as hydroxypropylcellulose, a surfactant such as fatty ester, and a plasticizer such as glycerin.

A pharmaceutical preparation that is appropriate for parenteral administration preferably comprises a sterile aqueous agent containing an active compound that is isoosmotic to a recipient's blood. For example, in the case of an injection, a solution for injection is prepared using a carrier of a saline solution, a glucose solution, or a mixture of saline water and a glucose solution. Furthermore, to these parenteral agents, one or more types of the following supplementary ingredients can also be added: an excipient, a disintegrating agent, a lubricant, a binder, a surfactant, a plasticizer and a diluent, an antiseptic agent, flavors, and the like as exemplified for oral agents.

Furthermore, it can also be attempted to maintain peptide absorption by appropriately selecting and adding fat, hyaluronic acid, a temperature-sensitive polymer, a macromolecule that is dissolved in water with difficulty, a surfactant, or the like.

When the above active ingredients or pharmacologically acceptable salts are used for the above purposes, they are generally administered systemically or locally in an oral or parenteral form. The dose and the number of instances of administration differ depending on the form of administration, the age and body weight of the patient, and the characteristics or severity of the symptoms to be treated. Generally in the case of oral administration, the dose ranges from 0.01 mg to 1000 mg and preferably from 0.05 mg to 500 mg per instance of administration for an adult. The dose is administered once or several times (in divided doses) a day. In the case of parenteral administration such as intravenous administration, generally the dose ranges from 0.001 mg to 1000 mg and preferably from 0.01 mg to 300 mg per adult administered once or several times (in divided doses) a day, or the dose is continuously administered intravenously within a time ranging from 1 to 24 hours per day. However, such dose and numbers of instances of administration are varied depending on the various conditions above.

Furthermore, in the case of a gene therapy agent, nucleic acids such as DNA or RNA are used as active ingredients of an agent for selectively inhibiting GDF-8, an agent for increasing skeletal muscle, an agent for decreasing fat, a therapeutic agent or a prophylactic agent for amyotrophic symptoms, or a therapeutic agent or a prophylactic agent for cachexia, disease accompanied by muscular atrophy, Type II diabetes, obesity, or acquired immunodeficiency syndrome. In such case, a method for pharmaceutically formulating, prescribing, and administering the DNA or the RNA alone or administering such DNA or RNA after insertion thereof into an appropriate vector such as a retroviral vector, an adenovirus vector, an adeno-associated virus vector, or the like according to the above-described standard method can be employed. Alternatively, a method for administering such DNA or RNA alone using a non-viral gene transfer method can be employed.

A recombinant viral vector can be constructed according to a method described below.

A DNA (hereinafter, also referred to as a subject DNA) fragment that is used as an active ingredient is prepared. A recombinant viral vector is constructed by inserting the DNA fragment downstream of a promoter within a viral vector.

In the case of an RNA viral vector, a recombinant virus is prepared by preparing an RNA fragment homologous to a subject DNA and then inserting the resultant downstream of a promoter within a viral vector. Regarding an RNA fragment, in addition to double strands, either a sense strand or an antisense strand is selected according to the viral vector type. For example, RNA homologous to a sense strand is selected in the case of a retroviral vector, and RNA homologous to an antisense strand is selected in the case of a sense viral vector.

The recombinant viral vector is introduced into packaging cells adequate for the vector. Packaging cells may be any packaging cells, as long as they can supply a deficient protein of a recombinant viral vector that lacks at least one gene encoding a protein required for viral packaging. For example, human-kidney-derived HEK293 cells, mouse fibroblasts NIH3T3, and the like can be used. Examples of such protein that is supplied by packaging cells include, in the case of a retroviral vector, gag, pol, and env derived from a mouse retrovirus, in the case of a lentivirus vector, gag, pol, env, vpr, vpu, vif, tat, rev, and nef derived from HIV, in the case of an adenovirus vector, E1A and E1B derived from an adenovirus, and in the case of an adeno-associated virus, Rep (p5, p19, p40), and Vp(Cap).

A viral vector that is used herein enables production of a recombinant virus in the above packaging cells and contains a promoter at a position such that a subject DNA can be transcribed in target cells. As a plasmid vector, MFG (Proc. Natl. Acad. Sci. U.S.A., 92, 6733 (1995)), pBabePuro (Nucleic Acids Res., 18, 3587 (1990)), LL-CG, CL-CG, CS-CC, CLG (J. Virol., 72, 8150 (1998)), pAdex1 (Nucleic Acids Res., 23, 3816 (1995)), or the like is used. Any promoter can be used, as long as it is functional in human tissue. Examples of such promoter include a cytomegalovirus (CMV) IE (immediate early) gene promoter, an SV40 early promoter, a retrovirus promoter, a metallothionein promoter, a heat shock protein promoter, and an SRα promoter. In addition, a human CMV IE gene enhancer can be used together with a promoter.

Examples of a method for introducing a recombinant viral vector into packaging cells include a calcium phosphate method (JP Patent Publication (Kokai) No. 2-227075 A (1990)) and a lipofection method (Proc. Natl. Acad. Sci. U.S.A., 84, 7413 (1987)).

Furthermore, as a method for administering the above recombinant viral vector, through combination with direct in vivo gene transfer using liposome delivery in addition to the above method, a viral vector can also be directed to a patient's cancer tissue. Specifically, a complex is prepared by combining a subject DNA of an appropriate size with a polylysine-conjugate antibody specific to an adenovirus-hexon protein. The thus obtained complex is bound to an adenovirus vector, so that a viral vector can be prepared. Such viral vectors can stably reach target cells, are incorporated by endosome into the cells, and then are decomposed within the cells. Hence, the gene can be efficiently expressed.

In the present invention, a vector expressing a subject DNA can also be transported to foci by a non-viral gene transfer method.

Examples of a non-viral gene transfer method known in the art include a calcium phosphate coprecipitation method (Virology, 52, 456 (1973); Science, 209, 1414 (1980)), a microinjection method (Proc. Natl. Acad. Sci. U.S.A., 77, 5399 (1980); Proc. Natl. Acad. Sci. U.S.A., 77, 7380 (1980); Cell, 27, 223 (1981); Nature, 294, 92 (1981)), a liposome-mediated and membrane-fusion-mediated transfection method (Proc. Natl. Acad. Sci. U.S.A., 84, 7413 (1987); Biochemistry, 28, 9508 (1989); J. Biol. Chem., 264, 12126 (1989); Hum. Gene Ther., 3, 267 (1992); Science, 249, 1285 (1990); Circulation, 83, 2007 (1992)), and a DNA transfer method mediated by direct DNA incorporation and a receptor (Science, 247, 1465 (1990); J. Biol. Chem., 266, 14338 (1991); Proc. Natl. Acad. Sci. U.S.A., 87, 3655 (1991); J. Biol. Chem., 264, 16985 (1989); BioTechniques, 11, 474 (1991); Proc. Natl. Acad. Sci. U.S.A., 87, 3410 (1990); Proc. Natl. Acad. Sci. U.S.A., 88, 4255 (1991); Proc. Natl. Acad. Sci. U.S.A., 87, 4033 (1990); Proc. Natl. Acad. Sci. U.S.A., 88, 8850 (1991); Hum. Gene Ther., 3, 147 (1991)).

With such liposome-mediated and membrane-fusion-mediated transfection method, direct administration of a product prepared with the use of a liposome to a target tissue enables local gene incorporation and expression in the tissue. A technique for direct DNA incorporation is preferable for DNA to directly target a patient's cancer tissue. DNA transfer mediated by a receptor is performed by conjugating a DNA (generally taking a form of supercoiled plasmid that is a covalently closed circular DNA) to a protein ligand via polylysine. A ligand to be used herein is selected based on the presence of the corresponding ligand receptor on target cells or cell surfaces of a target tissue. Such ligand-DNA conjugate can be directly injected into a blood vessel if necessary, so that it can be directed to a target tissue where binding to a receptor and internalization of a DNA-protein complex take place. To prevent intracellular disruption of DNA, endosome functions can also be destroyed by simultaneous infection with an adenovirus.

5. Transgenic Non-Human Mammal into Which Foreign Gene Containing Polynucleotide that Encodes the Follistatin Variant Polypeptide of the Present Invention is Introduced A transgenic non-human mammal can be produced by introduction of a foreign gene containing a polynucleotide that encodes the follistatin variant polypeptide of the present invention into a non-human mammal. The above transgenic non-human mammal wherein the follistatin variant polypeptide of the present invention is overexpressed is preferably characterized by increased skeletal muscle mass. Such transgenic non-human mammal is useful as a model animal that is used in research of the mechanism for skeletal muscle formation or research of diseases accompanied by abnormal skeletal muscle.

Specific examples of "non-human mammals" in this description include mice, rats, guinea pigs, hamsters, rabbits, dogs, cats, sheep, pigs, goats, cattle, and monkeys. Such non-human mammals are preferably rodents such as mice, rats, guinea pigs, hamsters, and rabbits and most preferably mice.

A method for producing the transgenic non-human mammal of the present invention will be hereafter described below.

(1) Preparation of Transgene

When a DNA encoding the follistatin variant polypeptide of the present invention is introduced into a subject animal, it is generally advantageous to use a gene construct wherein the DNA is ligated downstream of a promoter that enables expression of the DNA within the cells of the animal to be subjected to introduction. A gene to be introduced can be prepared by a standard method as described below, for example.

A DNA fragment with an appropriate length containing a portion that encodes the polypeptide is prepared if necessary, based on the full-length complementary DNA of a gene to be introduced. Subsequently, the DNA fragment or the full-length complementary DNA is inserted downstream of a promoter of an appropriate expression vector, so that a recombination vector is constructed.

As an expression vector for a gene to be introduced into an animal, a plasmid derived from *Escherichia coli*, a plasmid derived from *Bacillus subtilis*, a plasmid derived from yeast, a bacteriophage such as a λ phage, a retrovirus such as Moloney leukemia virus, or an animal virus such as vaccinia virus or Baculovirus is used. Of these plasmids, a plasmid derived from *Escherichia coli*, a plasmid derived from *Bacillus subtilis*, a plasmid derived from yeast, or the like is preferable. A plasmid derived from *Escherichia coli* is particularly preferable.

Specific examples of promoters that are used in the present invention are as described above in this description. An expression vector to be used in the present invention preferably has a sequence (generally referred to as a terminator) that terminates the transcription of a target messenger RNA in a transgenic mammal. For example, gene expression can be manipulated using a sequence (having such a transcription-terminating function) contained in genes derived from viruses, various mammals, and birds. Preferably, simian virus SV40 terminator or the like is frequently used. Furthermore, for the purpose of expressing a target gene at a higher level, a splicing signal of each gene, an enhancer region, and a part of an intron of a eukaryotic gene can be ligated to the 5' upstream of a promoter region, between the promoter region and a translation region, or the 3' downstream of the translation region, depending on purpose.

(2) Production of Transgenic Non-human Mammal

The transgenic non-human mammal of the present invention can be produced by introducing a DNA that encodes the follistatin variant polypeptide into a subject animal. Specifically, the gene is introduced into fertilized eggs, embryonic stem cells, somatic cells, sperm, or unfertilized eggs of a subject non-human mammal. The transgenic non-human mammal can thus be produced by obtaining such transgenic non-human mammal wherein the DNA encoding the target follistatin variant polypeptide has been incorporated on the chromosomes of all cells, including germinal cells. The gene is introduced into fertilized eggs, embryonic stem cells, somatic cells, sperm, or unfertilized eggs, preferably in such a way that the presence of the gene on the chromosomes of all cells, including germinal cells and somatic cells, of a subject non-human mammal, is ensured. The presence of such transgene in the germinal cells of a produced animal after introduction of the gene means that progenies of the produced animal have the transgene in all their germinal cells and somatic cells.

Selection of individual animals can be performed by confirming the expression of the transgene product at the protein or mRNA level. Progenies of the animal of this species, which have inherited the genes of the selected individual animals, have the transgene product. A homozygote animal having the transgene on both homologous chromosomes is obtained. Through crossing the female animal with the male animal, all the progenies stably retain the gene. Moreover, after confirmation of the possession of the gene, the progenies can be bred and passaged under a general breeding environment.

Transgenic animals can be produced through introduction of genes into fertilized eggs or embryonic stem cells using methods described in Manipulating Mouse Embryo, $2^{nd}$ edition, Gene Targeting, A Practical Approach, IRL Press at Oxford University Press (1993); Biomanual Series 8, Gene Targeting, Production of Mutant Mouse Using ES Cells, Yodosha Co., Ltd., (1995); Developmental Engineering Experimental Manual, How to Produce Transgenic Mice, Kodansha Ltd., (1987); and the like. Transgenic animals can be produced through introduction of genes into mammalian cells and nuclear transplantation using methods reported by Cibelli et al. (Science, 280, 1256, 1998), Schnieke et al. (Science, 278, 2130, 1997), Baguisi et al. (Nature Biotechnology, 17, 456, 1999), and the like. Transgenic animals can be produced through introduction of genes into sperm using methods reported by Perry et al. (Science, 284, 1180, 1999) and Wakayama et al. (Nature Biotechnology, 16, 639, 1998). Transgenic animals can be produced through introduction of genes into unfertilized eggs and external fertilization using a method reported by Chan et al. (Proc. Natl. Acad. Sci. U.S.A., 95, 14028, 1998).

6. Application for Improvement of Domestic Animals

Through administration of the follistatin variant polypeptide of the present invention, a polynucleotide encoding the polypeptide for expression within a living body to which the polypeptide is administered, or a vector containing the polynucleotide to a non-human animal such as cattle, a pig, sheep, a chicken, or the like, the skeletal muscle of the thus produced non-human animal can be increased and the fat of the same can be decreased. Furthermore, through production of a transgenic non-human animal into which a DNA encoding the follistatin variant polypeptide of the present invention is introduced in a manner similar to that of the method described in 5, the skeletal muscle of the thus produced non-human animal can be increased and the fat of the same can be decreased. Particularly, when a non-human animal is a domestic animal, a domestic animal with a greater amount of meat but with a lesser amount of fat can be produced as described above. Hence, the production amount of meat can be increased and high quality meat with less fat can be produced. Moreover, the working power of domestic animals can be improved by increasing their skeletal muscle.

Examples of the present invention will be hereafter described in detail, but the scope of the present invention is not limited by these examples.

EXAMPLES

Example 1

Construction of Expression Vectors for Follistatin Variant Polypeptides

A human follistatin precursor cDNA (Proc. Natl. Acad. Sci. U.S.A., 85, 4218, (1988)) was cloned from the human testis cDNA library (produced by Clontech) by hybridization using a pig follistatin precursor cDNA as a probe. The human follistatin precursor cDNA was inserted between the EcoR I site and the Xba I site in a plasmid pUC19 (produced by Takara Holdings), so that template pUC19/FS for a follistatin variant was prepared.

To a reaction solution containing 0.2 mmol/l dNTPs and 1 mmol/l magnesium chloride, 100 ng of the template for the follistatin variant and 10 pmol of each of synthetic DNAs (produced by Genset) having the nucleotide sequences shown in SEQ ID NO: 11 and SEQ ID NO: 12, were added. Furthermore, 2.5 units of Taq polymerase (TaKaRa Ex Taq; Produced by Takara Holdings) were added to a total amount of 25 μl, and then PCR was performed. Reaction conditions consisted of 3 cycles of 94° C. for 30 seconds, 74° C. for 15 seconds, and 72° C. for 30 seconds, 3 cycles of 94° C. for 30 seconds, 70° C. for 15 seconds, and 72° C. for 30 seconds, 3 cycles of 94° C. for 30 seconds, 66° C. for 15 seconds, and 72° C. for 30 seconds, 3 cycles of 94° C. for 30 seconds, 62° C. for 15 seconds, and 72° C. for 30 seconds, 3 cycles of 94° C. for 30 seconds, 58° C. for 15 seconds, and 72° C. for 30 seconds, and 12 cycles of 94° C. for 30 seconds, 54° C. for 15 seconds, and 72° C. for 30 seconds, followed by 1 cycle of 72° C. for 10 minutes. The reaction solution was fractionated by 1% agarose gel electrophoresis, and then an approximately 0.25-kb gene amplification fragment A was collected (FIG. 2). The amino acid sequence encoded by the gene amplification fragment A contains the sequence ranging from the $95^{th}$ to the $168^{th}$ amino acids of SEQ ID NO: 4 and contains human follistatin FSI.

Figure 3:
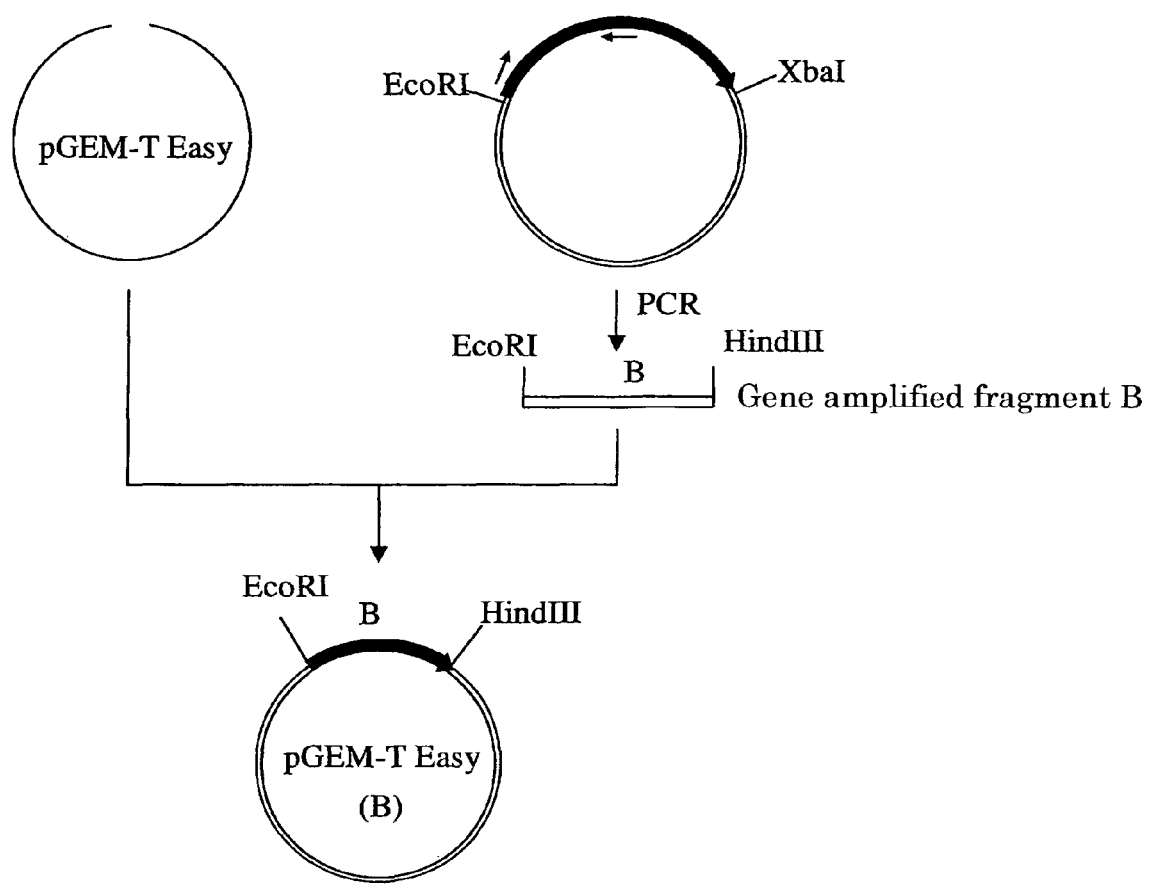
FIG. 3 shows construction steps for plasmid pGEM-T Easy (B).

By the use of 10 pmol each of synthetic DNAs (produced by Genset) having the nucleotide sequences shown in SEQ ID NO: 13 and SEQ ID NO: 14, respectively, as primers, PCR was performed under conditions similar to those employed for the above gene amplification fragment A. The reaction solution was fractionated by 1% agarose gel electrophoresis, so that an approximately 0.6-kb gene amplification fragment B was harvested (FIG. 3). The amino acid sequence encoded by the gene amplification fragment B contains the sequence ranging from the $1^{st}$ to the $166^{th}$ amino acids of SEQ ID NO: 4, and contains human follistatin FSN and FSI.

The thus obtained gene amplification fragments A and B were each ligated to pGEM-T Easy vectors using a pGEM-T Easy TA cloning kit (produced by Promega) according to the attached instructions, thereby resulting in plasmids pGEM-T Easy (A) and pGEM-T Easy (B) shown in FIG. 2 and FIG. 3, respectively.

Figure 4:
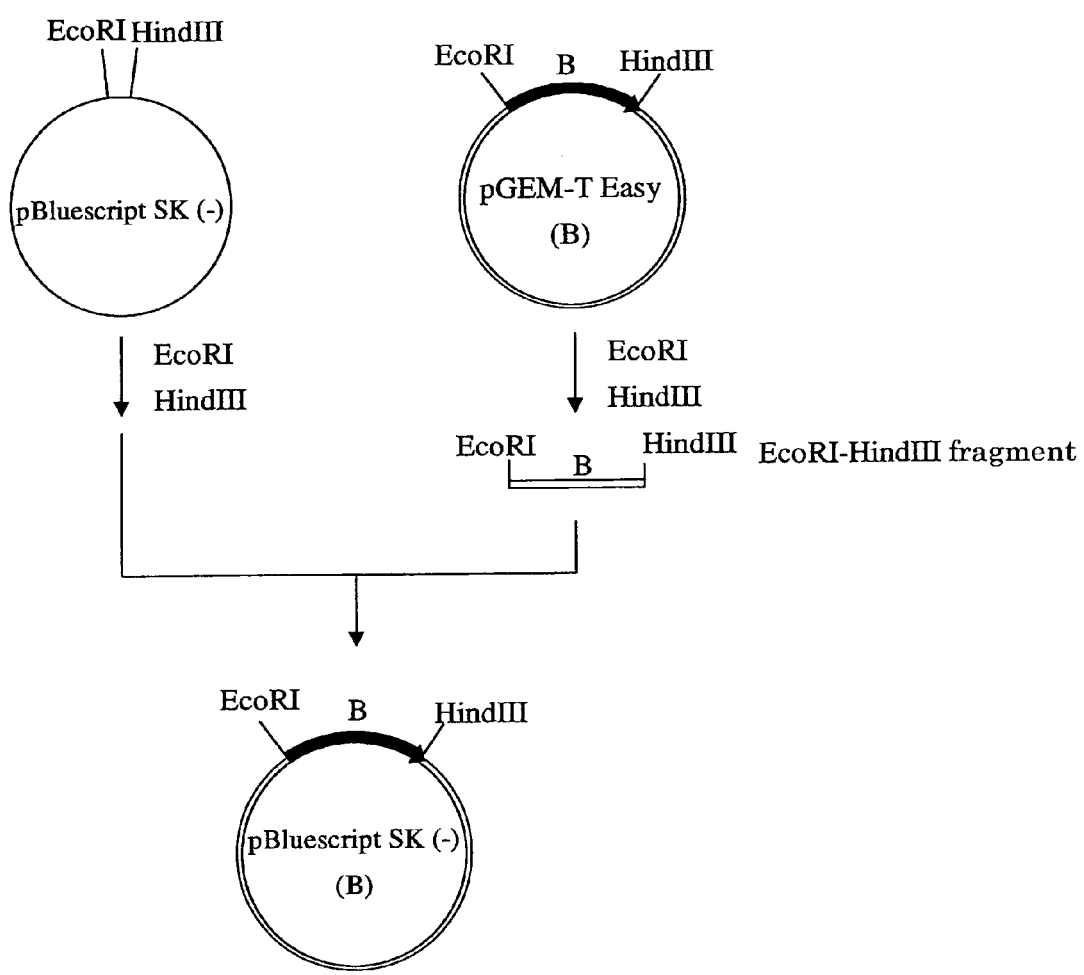
FIG. 4 shows construction steps for plasmid pBluescript SK(−)(B).

Next, an approximately 0.59-kb EcoR I-Hind III fragment (B) containing the amplification fragment B, which had been obtained by digesting plasmid pGEM-T Easy (B) with restriction enzymes EcoR I (produced by Takara Holdings) and Hind III (produced by Takara Holdings), was ligated to an approximately 2.95-kb EcoR I-Hind III fragment that had been obtained by digesting pBluescript SK (−) (produced by Stratagene) with EcoR I and Hind III. Hence, plasmid pBluescript SK (−) (B) shown in FIG. 4 was prepared.

Figure 5:
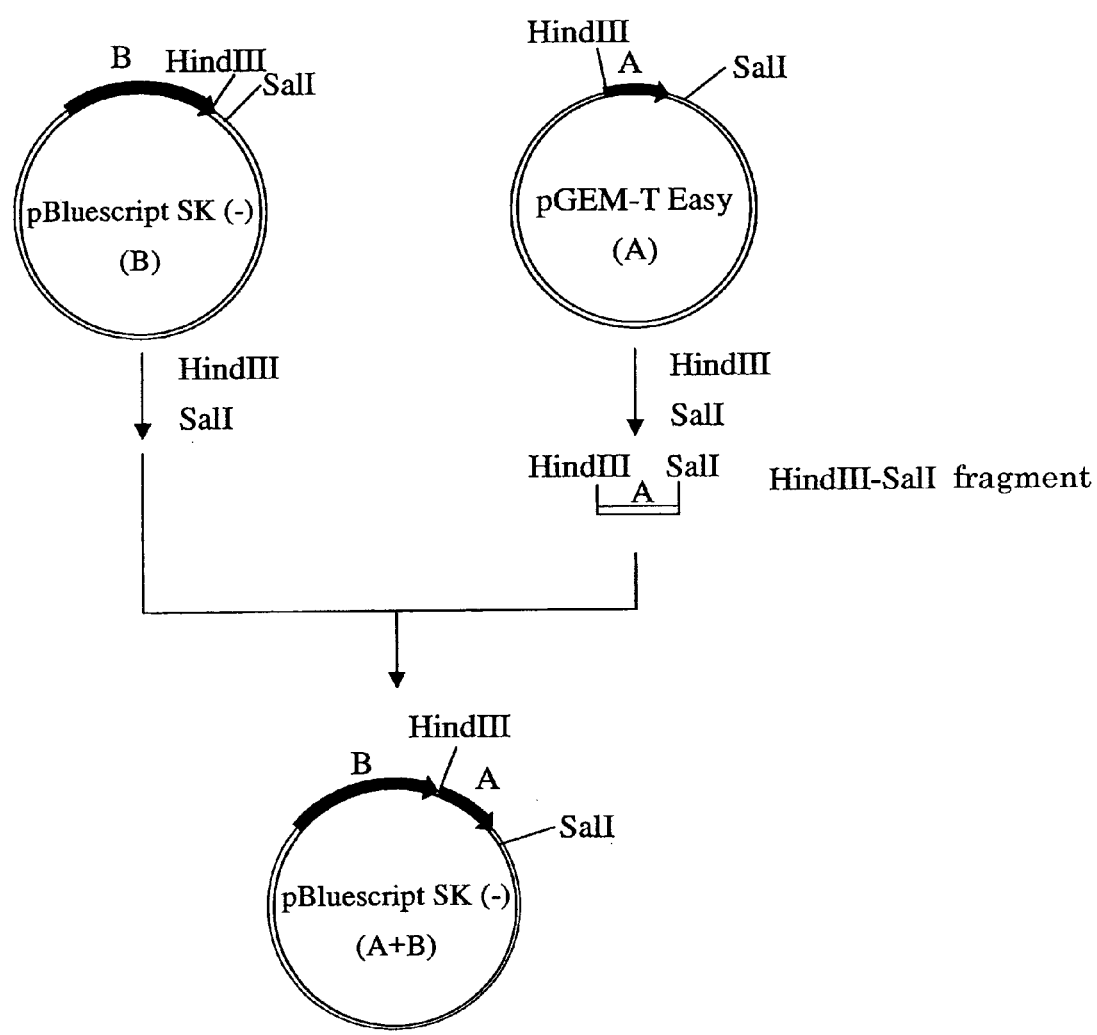
FIG. 5 shows construction steps for plasmid pBluescript SK(−)(A+B).

Next, an approximately 0.27-kb Hind III-Sal I fragment (A) containing the amplification fragment A, which had been obtained by digesting plasmid pGEM-T Easy (A) with restriction enzymes Hind III and Sal I (produced by Takara Holdings), was ligated to an approximately 3.54-kb Hind III-Sal I fragment (B) that had been obtained by digesting plasmid pBluescript SK (−) (B) with Hind III and Sal I. Thus, plasmid pBluescript SK (−) (A+B) shown in FIG. 5 was prepared.

Figure 6:
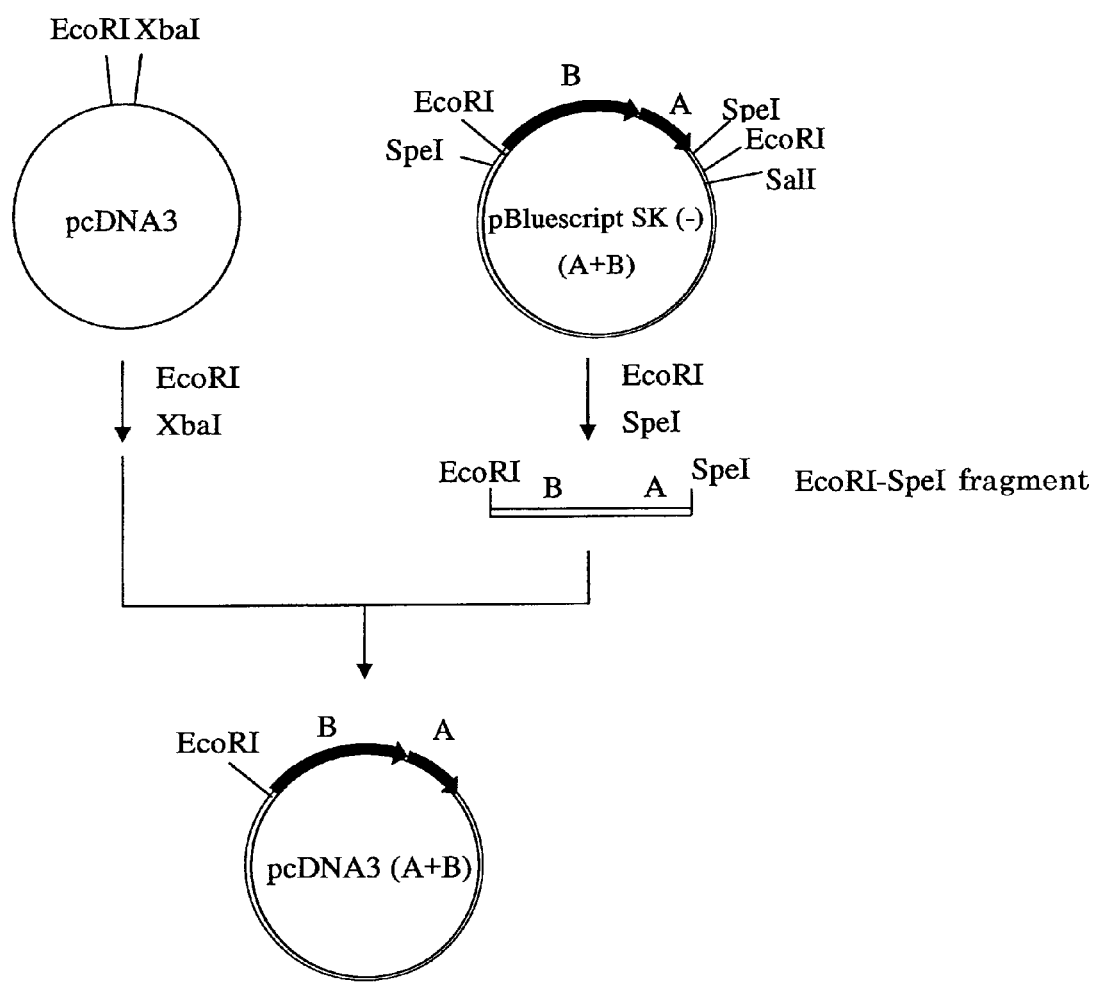
FIG. 6 shows construction steps for plasmid pcDNA3 (A+B).

Next, an approximately 0.84-kb Eco RI-Spe I fragment (A+B) containing the amplification fragments A and B, which had been obtained by digesting plasmid pBluescript SK (−) (A+B) with restriction enzymes EcoR I and Spe I (produced by Takara Holdings), was ligated to an approximately 5.4-kb EcoR I-Xba I fragment that had been obtained by digesting plasmid pcDNA3 (produced by Invitrogen) for expression in animal cells with EcoR I and Xba I (produced by Takara Holdings). Thus, follistatin variant polypeptide expression vector pcDNA3 (A+B) shown in FIG. 6 was obtained. The nucleotide sequence of the region encoding a follistatin variant polypeptide contained in pcDNA3 (A+B) is shown in SEQ ID NO: 15. The amino acid sequence of the polypeptide is shown in SEQ ID NO: 16. The amino acid sequence ranging from the $1^{st}$ to the $29^{th}$ amino acids of SEQ ID NO: 16 is a signal peptide and is cleaved upon secretion of the polypeptide. Hence, animal cells into which pcDNA3 (A+B) has been introduced secrete the follistatin variant polypeptide (hereinafter referred to as FS 1-1) comprising the amino acid sequence of SEQ ID NO: 6. FS1-1 contains human follistatin FSN and two FSIs, but is the follistatin variant polypeptide that lacks FSII and FSIII.

Figure 7:
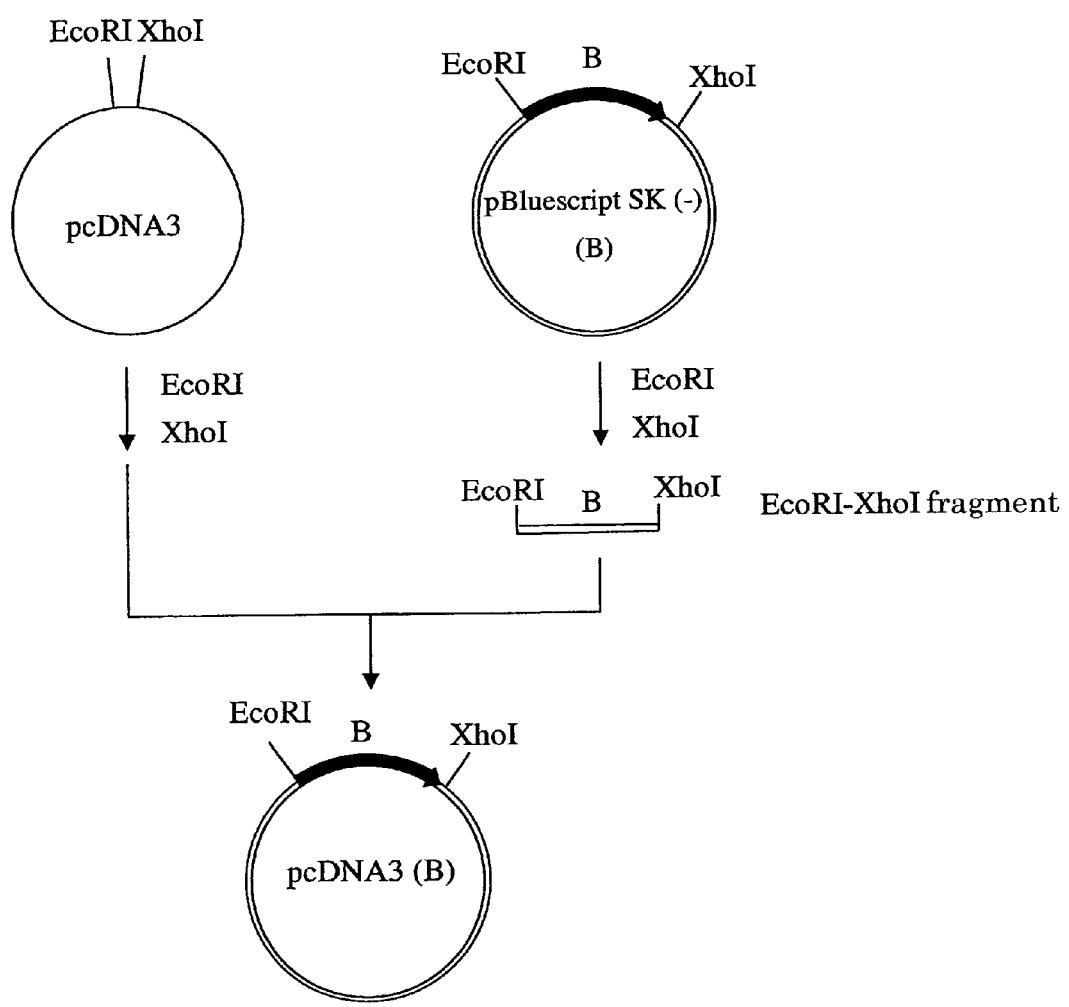
FIG. 7 shows construction steps for plasmid pcDNA3 (B).

Furthermore, an approximately 0.6-kb EcoR I-Xho I fragment containing the amplification fragment B, which had been obtained by digesting pBluescript SK (−) (B) with EcoR I and Xho I, was ligated to an approximately 5.4-kb EcoR I-Xho I fragment that had been obtained by digesting plasmid pcDNA3 for expression in animal cells with EcoR I and Xho I. Thus, follistatin variant polypeptide expression vector pcDNA3 (B) shown in FIG. 7 was obtained. The nucleotide sequence of the region encoding a follistatin variant polypeptide contained in pcDNA3 (B) is shown in SEQ ID NO: 17 and the amino acid sequence of the polypeptide is shown in SEQ ID NO: 18. The amino acid sequence ranging from the $1^{st}$ to the $29^{th}$ amino acids of SEQ ID NO: 18 is a signal peptide and is cleaved upon secretion of the polypeptide. Therefore, animal cells wherein pcDNA3 (B) has been introduced secrete the follistatin variant polypeptide (hereinafter, referred to as FS1) comprising the amino acid sequence of the SEQ ID NO: 8. FS1 contains human follistatin FSN and one FSI and is the follistatin variant polypeptide that lacks FSII and FSIII.

Figure 8:
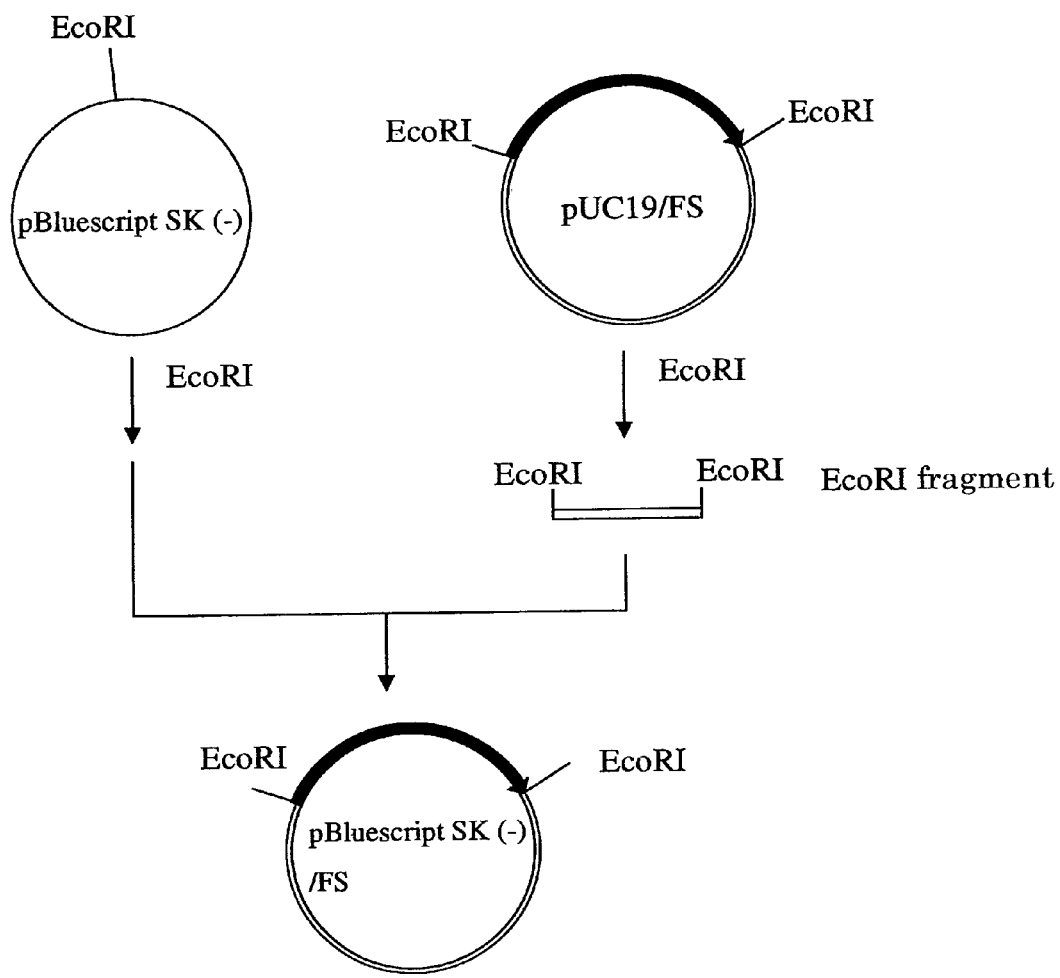
FIG. 8 shows construction steps for plasmid pBluescript SK(−)/FS.
Figure 9:
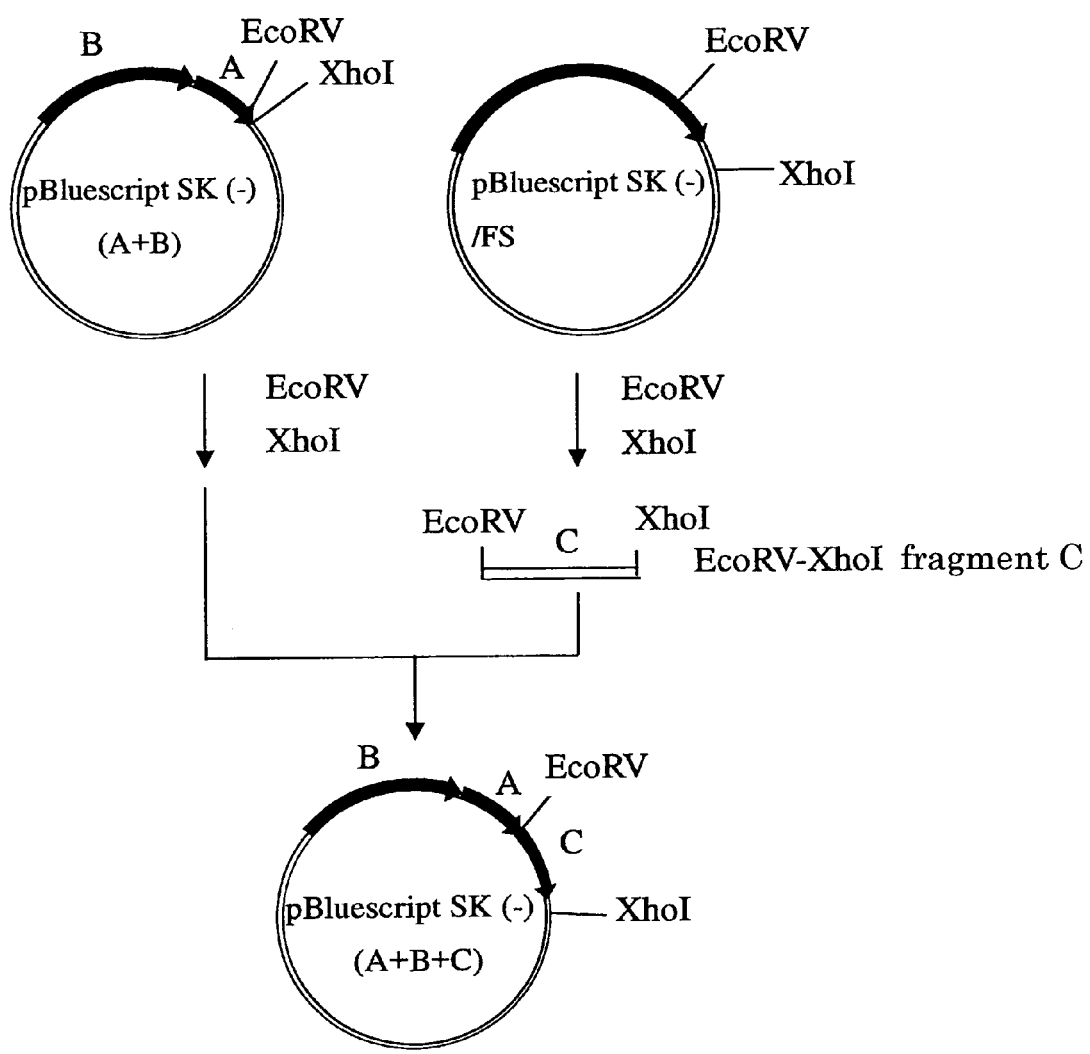
FIG. 9 shows construction steps for plasmid pBluescript SK(−) (A+B+C).

Furthermore, an approximately 1.1-kb EcoR I fragment containing a human follistatin precursor cDNA, which had been obtained by digesting a template for a follistatin variant with EcoR I, was inserted into the EcoR I site of plasmid pBluescript SK(−), thereby resulting in pBluescript SK(−)/ FS shown in FIG. 8. An approximately 0.4-kb EcoR V-Xho I fragment C obtained by digesting plasmid pBluescript SK (−)/FS with EcoR V and Xho I was ligated to an approximately 3.8-kb EcoR V-Xho I fragment obtained by digesting plasmid pBluescript SK(−)(A+B) with EcoR V and Xho I. Thus, plasmid pBluescript SK(−)(A+B+C) shown in FIG. 9 was prepared.

Figure 10:
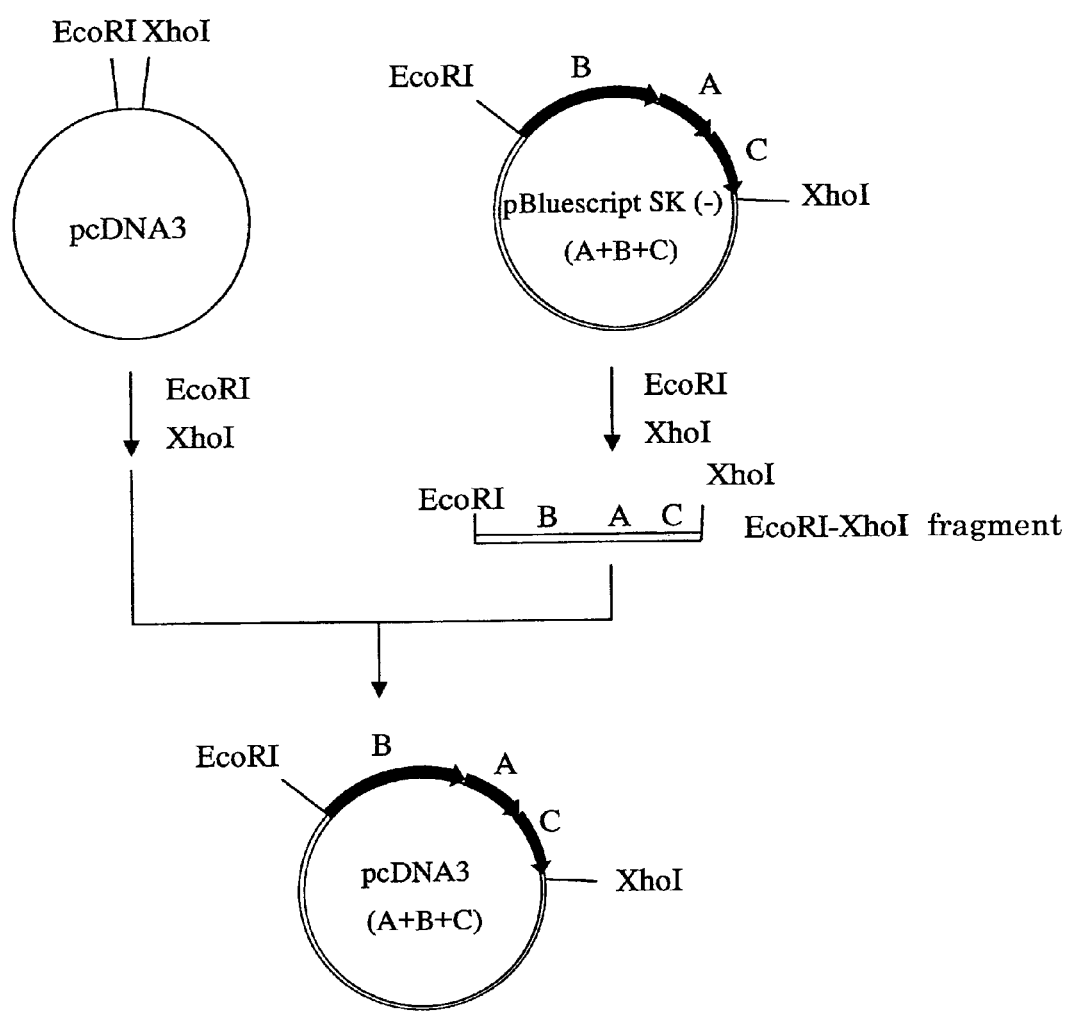
FIG. 10 shows construction steps for plasmid pcDNA3 (A+B+C).

Next, an approximately 1.2-kb EcoR I-Xho I fragment obtained by digesting pBluescript SK(−)(A+B+C) with EcoR I and Xho I was ligated to an approximately 5.4-kb EcoR I-Xho I fragment obtained by digesting plasmid pcDNA3 for expression in animal cells with EcoR I and Xho I. Thus, follistatin variant polypeptide expression vector pcDNA3(A+ B+C) shown in FIG. 10 was obtained. The nucleotide sequence of the region encoding a follistatin variant polypeptide contained in pcDNA3(A+B+C) is shown in SEQ ID NO: 19, and the amino acid sequence of the polypeptide is shown in SEQ ID NO: 20. The amino acid sequence ranging from the $1^{st}$ to the $29^{th}$ amino acids of SEQ ID NO: 20 is a signal peptide and is cleaved upon secretion of the polypeptide. Therefore, animal cells wherein pcDNA3 (A+B+C) has been introduced secrete the follistatin variant polypeptide (hereinafter, referred to as FS1-1-3) comprising the amino acid sequence of SEQ ID NO: 10. FS1-1-3 contains human follistatin FSN, two FSIs, and almost the whole FS3, and is the follistatin variant polypeptide that lacks FSII.

Figure 11:
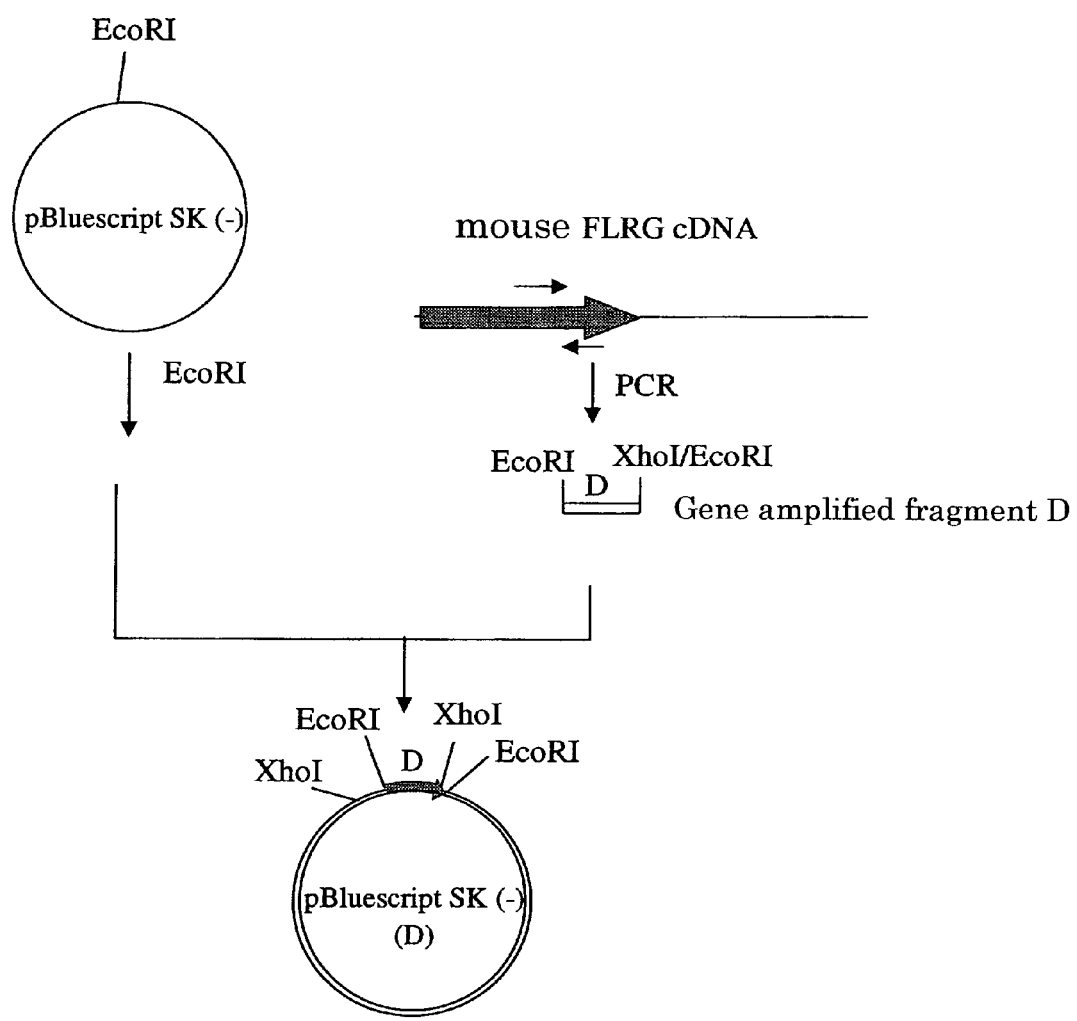
FIG. 11 shows construction steps for plasmid pBluescript SK(−) (D).

With the use of mouse FLRG cDNA (J. Biol. Chem., 275, 40788 (2000)) as a template and 10 pmol each of synthetic DNAs (produced by Genset) having nucleotide sequences shown in SEQ ID NO: 21 and SEQ ID NO: 22, respectively, as primers, PCR was performed under similar conditions as those employed for the above gene amplification fragment A. The reaction solution was fractionated by 1% agarose gel electrophoresis, and then an approximately 0.3-kb gene amplification fragment D was collected (FIG. 11). The amino acid sequence encoded by the gene amplification fragment contains the amino acid sequence ranging from the $165^{th}$ to the $256^{th}$ amino acids of mouse FLRG (NCBI protein database: accession No. BAB32663), and contains a mouse FLRG FSII-like domain (the region ranging from the 169th to the 241st amino acids of NCBI protein database: accession No. BAB32663). As shown in FIG. 14, the mouse FLRG FSII-like domain has 56% (41/73) homology with mouse follistatin FSII in terms of amino acid sequence and has 61.6% (45/73) homology with the amino acid sequence of SEQ ID NO: 2.

Figure 12:
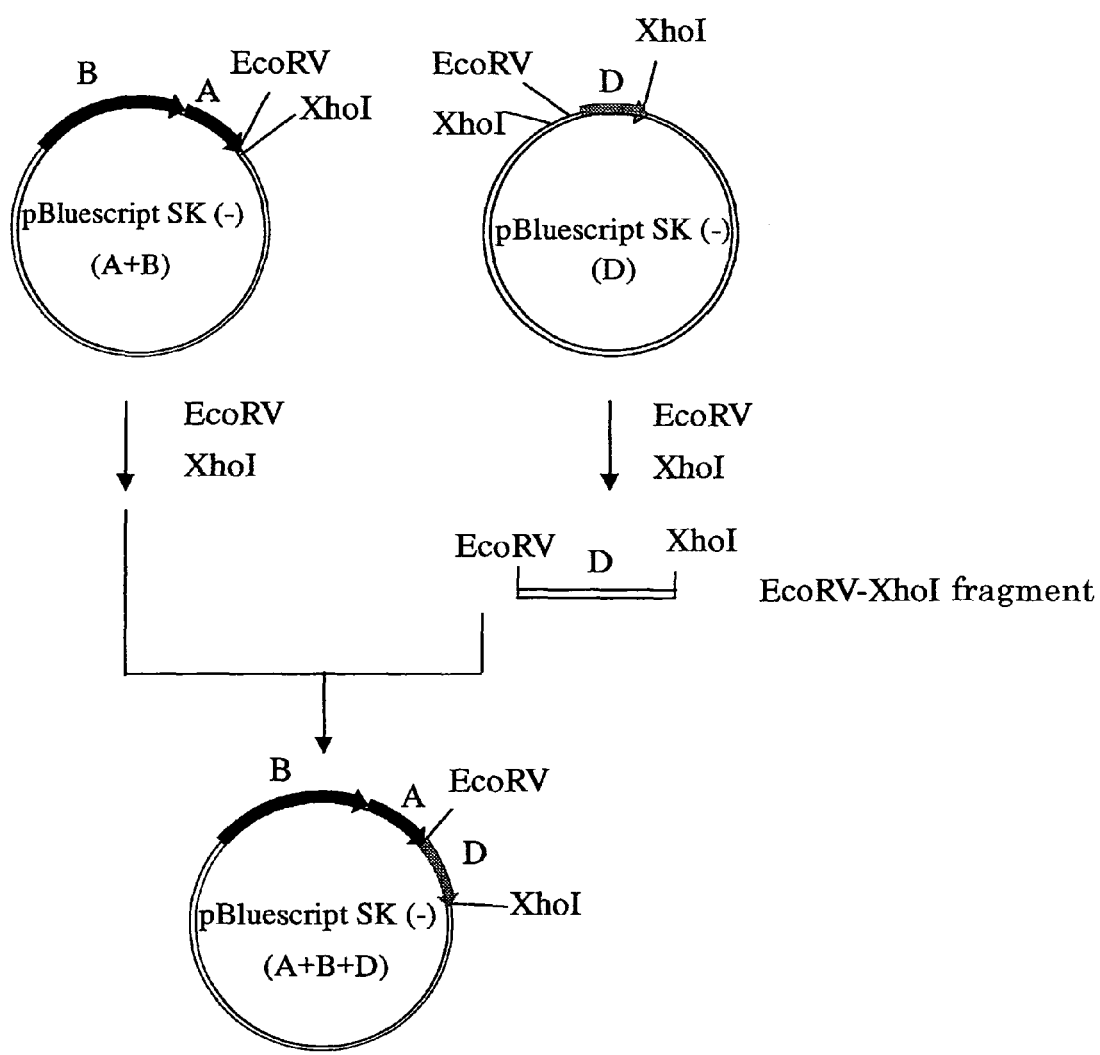
FIG. 12 shows construction steps for plasmid pcDNA3 (A+B+D).

The thus obtained gene amplification fragment D was digested with EcoR I and then inserted into the EcoR I site of pBluescript SK(−), resulting in pBluescript SK(−)(D) shown in FIG. 11. An approximately 0.3-kb EcoR V-Xho I fragment obtained by digesting the thus obtained plasmid pBluescript SK(−)(D) with EcoR V and Xho I was ligated to an approximately 3.8-kb EcoR V-Xho I fragment obtained by digesting plasmid pBluescript SK(−)(A+B) with EcoRV and Xho I. Thus, plasmid pBluescript SK(−)(A+B+D) shown in FIG. 12 was prepared.

Figure 13:
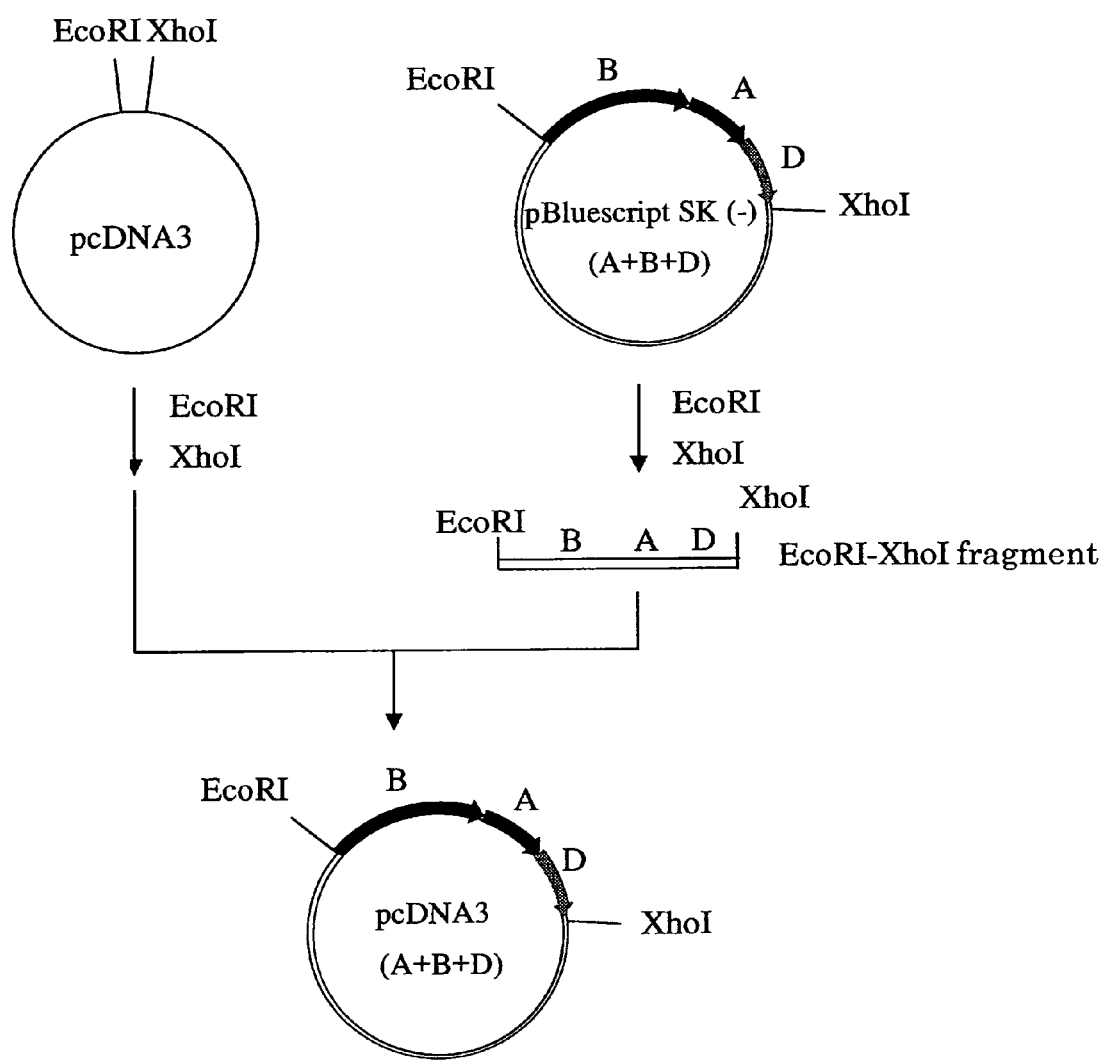
FIG. 13 shows construction steps for plasmid pcDNA3 (A+B+D).

Next, an approximately 1.1-kb EcoRI-Xho I fragment obtained by digesting pBluescript SK(−)(A+B+D) with EcoR I and Xho I was ligated to an approximately 5.4-kb EcoRI-Xho I fragment obtained by digesting plasmid pcDNA3 for expression in animal cells with EcoRI and Xho I. Thus, follistatin variant polypeptide expression vector pcDNA3(A+B+D) shown in FIG. 13 was obtained. The nucleotide sequence of the region encoding a follistatin variant polypeptide contained in pcDNA3(A+B+D) is shown in SEQ ID NO: 23, and the amino acid sequence of the polypeptide is shown in SEQ ID NO: 24. The amino acid sequence ranging from the 1st to the 29th amino acids of SEQ ID NO: 24 is a signal peptide and is cleaved upon secretion of the polypeptide. Therefore, animal cells into which pcDNA3 (A+B+D) has been introduced secrete the follistatin variant polypeptide (hereinafter, referred to as FS1-1-2') comprising the amino acid sequence of SEQ ID NO: 25. FS1-1-2' contains human follistatin FSN and two FSIs, and is the follistatin variant polypeptide that contains a mouse FLRG FSII-like domain instead of FSII.

Example 2

Expression and Purification of the Follistatin Variant Polypeptides Using Animal Cells (1) Introduction of Expression Vectors Into COS-7 Cells and Culture of the COS-7 Cells The follistatin variant polypeptides were expressed in animal cells using the follistatin variant polypeptide expression vectors pcDNA3(A+B), pcDNA3(B), pcDNA3(A+B+C), and pcDNA3(A+B+D) obtained in Example 1, as described below.

20 µg of plasmid pcDNA3(A+B) was introduced per $1 \times 10^6$ COS-7 (ATCC CRL-1651) cells by an electroporation method (Cytotechnology, 3, 133 (1990)). Subsequently, the COS-7 cells were suspended in 10 ml of Dulbecco's Modified Eagle Medium (DMEM; produced by Sigma-Aldrich) supplemented with 10% fetal calf serum (FCS). The resultant was inoculated on cell culture dishes (produced by Corning) each having a diameter of 10 cm. The cells were cultured within a 5% $CO_2$ incubator at 37° C. for 24 hours. Each medium was exchanged with 10 ml of DMEM and then the cells were cultured for 3 days. The above culture was performed using six cell culture dishes. Approximately 60 ml of the culture supernatant was collected. pcDNA3(B), pcDNA3(A+B+C), and pcDNA3 (A+B+D) were similarly introduced into COS-7 cells, culture was performed, and then approximately 60 ml of each culture supernatant was collected.

(2) Purification and Detection of the Follistatin Variant Polypeptides

Approximately 60 ml each of the culture supernatants of the COS-7 cells expressing each of four types of follistatin variant polypeptide obtained in (1) was applied to 2 ml of a sulfated cellulofine column (produced by Seikagaku Corporation) equilibrated with 20 mmol/L Tris-HCl (pH 7.2), 0.3 mol/L NaCl, and 0.03% 3-[(3-cholamidopropyl)dimethylammonio]-1-propane sulfonate (CHAPS). Subsequently, the column was washed with a total 20 ml of 20 mmmol/L Tris-HCl (pH 7.2), 0.3 mol/L NaCl, and 0.03% CHAPS, and then with a total 6 ml of 20 mmmol/L Tris-HCl (pH 7.2), 0.5 mol/L NaCl, and 0.03% CHAPS. Subsequently, adsorbed proteins were eluted from the column using a total 10 ml of 20 mmmol/L Tris-HCl (pH 7.2), 1.0 mol/L NaCl, and 0.03% CHAPS. The eluate was concentrated using the Ultrafree-15 Centrifugal Filter Unit (provided with Biomax10 membrane; produced by Millipore) according to the attached instructions, thereby resulting in 200 µl of a follistatin variant polypeptide solution.

The peptide comprising the amino acid sequence of SEQ ID NO: 26, the human follistatin FSI partial sequence, was chemically synthesized. Rabbits were immunized with the peptide as an antigen according to a standard method (Antibodies: A Laboratory Manual, Cold Spring Harbor Laboratory (1988)). Sera were collected from the rabbits with elevated antibody titers, and thereby a rabbit anti-follistatin polyclonal antibody was obtained. The antibody class was IgG.

Each of the thus obtained follistatin variant polypeptides was subjected to SDS-PAGE according to a known method (Nature, 227, 680 (1970)). Phoresed proteins were transferred to membranes (Immobilon P; produced by Millipore), followed by blocking of the membranes with 5% skim milk (produced by Nacalai Tesque). The resultants were caused to react with the rabbit anti-follistatin polyclonal antibody. Detection was performed using a horseradish peroxidase-labeled rat anti-rabbit IgG antibody (produced by Chemicon) and a chemiluminescence reagent (ECL detection reagent; produced by Amersham Biosciences). Each of the follistatin variant polypeptides was detected with the use of the rabbit anti-follistatin polyclonal antibody.

Figure 15:
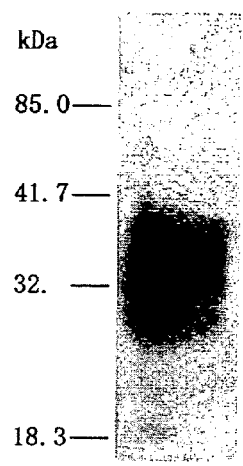
FIG. 15 shows FS1-1 as detected by Western blotting.

FIG. 15 shows Western blot analysis of FS1-1. FS1-1 comprises 254 amino acids and has a presumed molecular weight of approximately 27 kD. On the other hand, the molecular weights obtained by Western blot analysis were 31 kD, 33 kD, and 37 kD. Since FS1-1 has a sugar chain addition site, it is thought that the molecular weights became bigger because of sugar chain addition.

Example 3

Assay of the Activity of the Follistatin Variant Polypeptides to Inhibit the Activin Functions and GDF-8 Functions by Reporter Assay HEK293 cells (ATCC NO: CRL-1573) were inoculated on a 24-well plate at $5 \times 10^4$ cells/well and then cultured in 1 ml of a high-glucose-containing DMEM medium (produced by Sigma-Aldrich) supplemented with 10% FCS, penicillin (100 units/ml), and streptomycin (100 µg/ml) (hereinafter, referred to as a serum-containing DMEM medium) for 24 hours. The resultant was washed with phosphate buffered saline (PBS) and then transfected with reporter plasmid $(CAGA)_{12}$-MLP-Luc (EMBO J., 17, 3091 (1998)) (3 µg/well) and internal standard plasmid CMV-β-gal (1 µg/well). Transfection was performed by culturing the cells in a serum-free DMEM medium (200 µl) supplemented with a mixed solution of a plasmid and cationic liposome (Transfast; produced by Promega) for 2 hours at 37° C. A serum-containing DMEM medium (1 ml) was further added, followed by 24 hours of culture at 37° C.

The cells were washed with PBS. A serum-free DMEM medium containing (a) activin (10 ng/ml), (b) GDF-8 (15 ng/ml), (c) activin (10 ng/ml) and follistatin (100 ng/ml), (d) GDF-8 (15 ng/ml) and follistatin (100 ng/ml), (e) activin (10 ng/ml) and 5 µl of a follistatin variant polypeptide FS1-1 solution, or (f) GDF-8 (15 ng/ml) and 5 µl of a follistatin variant polypeptide FS1-1 solution was added at 200 µl/well, followed by 24 hours of culture at 37° C. The cells were washed with PBS. Subsequently, a cell lysis buffer (1% (v/v) triton X-100, 15 mmol/l $MgSO_4$, 4 mmol/l ethylene glycol-bis(2-aminoethylether)-N,N,N',N'-tetraacetic acid, 1 mmol/l DL-dithiothreitol, 25 mmol/l glycylglycine, pH 7.0) was added at 100 µl/well. The resultants were allowed to stand at 0° C. for 15 minutes. Thus, cell lysis solutions were prepared. 50 µl of each cell lysis solution was mixed with 105 µl of a luciferase assay buffer (0.24 mmol/l luciferin, 1.4 mmol/l ATP, 4.8 mmol/l $KH_2PO_4$, 4.8 mmol/l $MgCl_2$, pH 7.4), and then the amount of light emitted was measured using a luminometer (MicroLumat) LP98P; produced by BERTHOLD). Relative light units (RLU) during the period from the initiation of reaction to 20 seconds after the initiation were accumulated, and luciferase activity was thereby obtained. Subsequently, 35 µl of each cell lysis solution was mixed with 235µl of a β-galactosidase assay buffer (1.6 mg/ml o-nitrophenyl-β-D-galactoside, 60 mmol/l $Na_2HPO_4$, 40 mmol/l $NaH_2PO_4$, 10 mmol/l KCl, 1 mmol/l $MgCl_2$, and 50 mmol/l β-mercaptoethanol). Optical density (OD) was measured using an absorption spectrometer (Microplate Reader Benchmark; produced by BIO-RAD). The value obtained by the following equation was designated as standardized luciferase activity and then used as an index of transcription-promoting activity.

Standardized luciferase activity=$RLU/OD$

Figure 16:
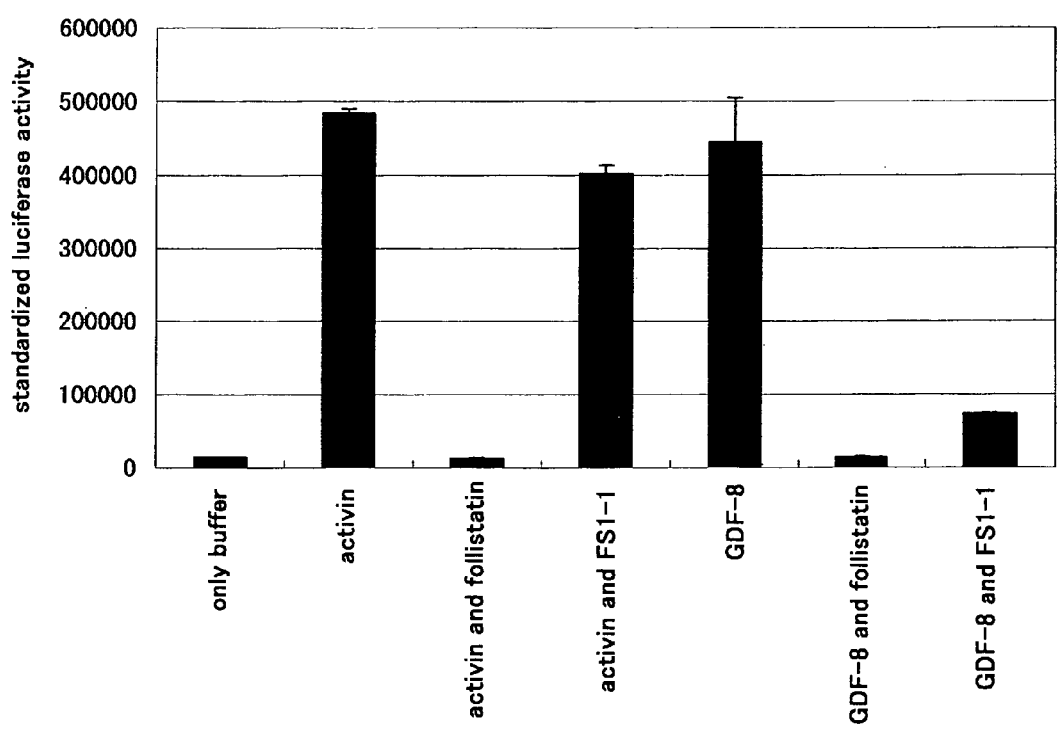
FIG. 16 shows the results of reporter assay to measure the inhibition of activin activity and GDF-8 activity by FS1-1.

Measurement results are shown in FIG. 16. Follistatin inhibited 100% of elevation in both the standardized luciferase activity due to activin and the same due to GDF-8. In the meantime, whereas the follistatin variant polypeptide inhibited 86% of elevation in the standardized luciferase activity due to GDF-8, it inhibited only 17% of elevation in standardized luciferase activity due to activin.

Figure 17:
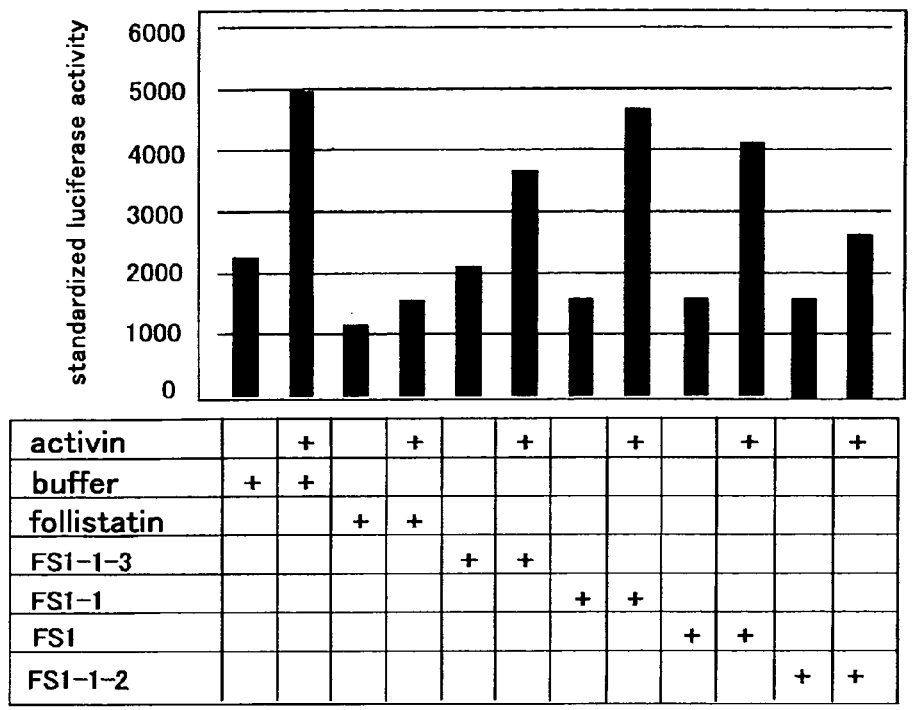
FIG. 17 shows the results of reporter assay to measure the inhibition of activin activity by various follistatin variants. Polypeptides indicated with "+" were each added.
Figure 18:
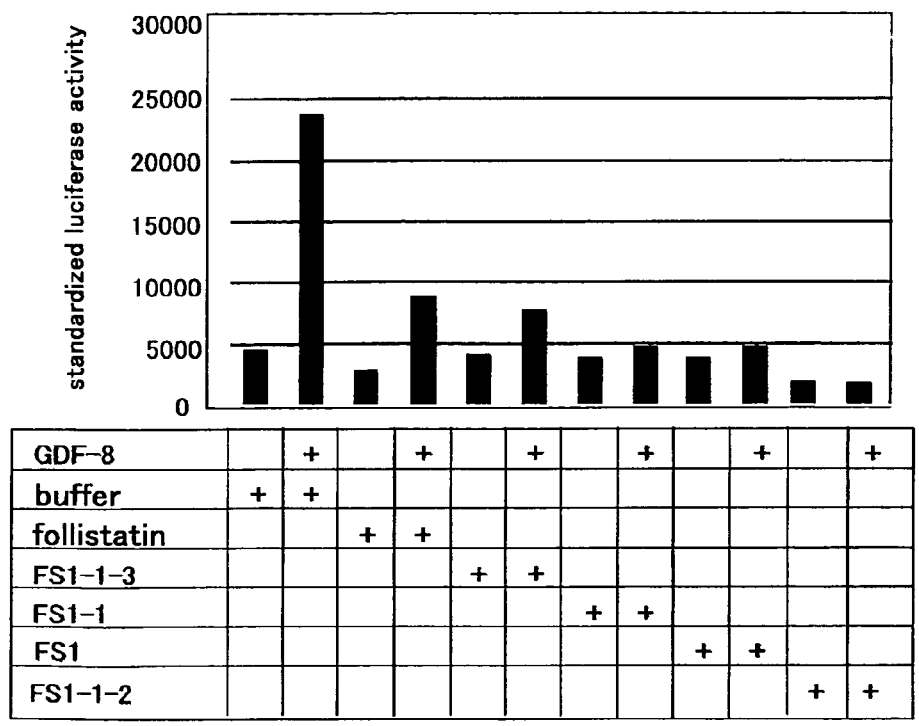
FIG. 18 shows the results of reporter assay to measure the inhibition of GDF-8 activity by various follistatin variants. Polypeptides indicated with "+" were each added.

Also for the follistatin variant polypeptides FS1, FS1-1-3, and FS1-1-2', assay was performed in a manner similar to that performed for the above FS1-1. As a result, as shown in FIG. 17 and FIG. 18, FS1 and FS 1-1-3 almost completely inhibited elevation in standardized luciferase activity due to GDF-8, similarly to the case of FS1-1, but almost never inhibited elevation in standardized luciferase activity due to activin. However, the degree of inhibiting elevation in standardized luciferase activity due to activin was somewhat stronger in the case of FS1 than that in the case of FS1-1, and in the case of FS1-1-3 than that in the case of FS1. Of these 3 types, it was demonstrated that FS1-1 inhibited GDF-8 activity most selectively. Therefore, it was revealed that to selectively inhibit GDF-8 activity, the follistatin variant polypeptide preferably contains 2 or more FSIs and also lacks FSIII in addition to FSII. Moreover, FS1-1-2' inhibited not only elevation in standardized luciferase activity due to GDF-8, but also elevation in standardized luciferase activity due to activin. Therefore, it was demonstrated that to selectively inhibit GDF-8 activity, the follistatin variant polypeptide preferably contains no FSII and no FSII-like domains.

Example 4

Increases in Skeletal Muscle Mass and Decreases in Fat Level of Mice Caused to Overexpress the Follistatin Variant Polypeptides An EcoR I-Sac I fragment containing a DNA encoding the follistatin variant polypeptide FS1-1, which had been obtained by digesting the pcDNA3 (A+B) prepared in Example 1 with EcoR I and Sac I, was inserted between the EcoR I site and the Sac I site of vector pSP72 (produced by Promega). The EcoR I-Sac I fragment containing a DNA encoding the follistatin variant polypeptide FS1-1, which had been obtained by digesting the thus obtained plasmid with EcoR I and Sma I, was inserted between the EcoR I site and the Sac I site located downstream of a myosin light chain promoter of an MDAF2 vector (Proc. Natl. Acad. Sci. U.S.A., 98, 9306 (2001)). Thus, plasmid MDAF2-FS1-1 was obtained.

Figure 19:
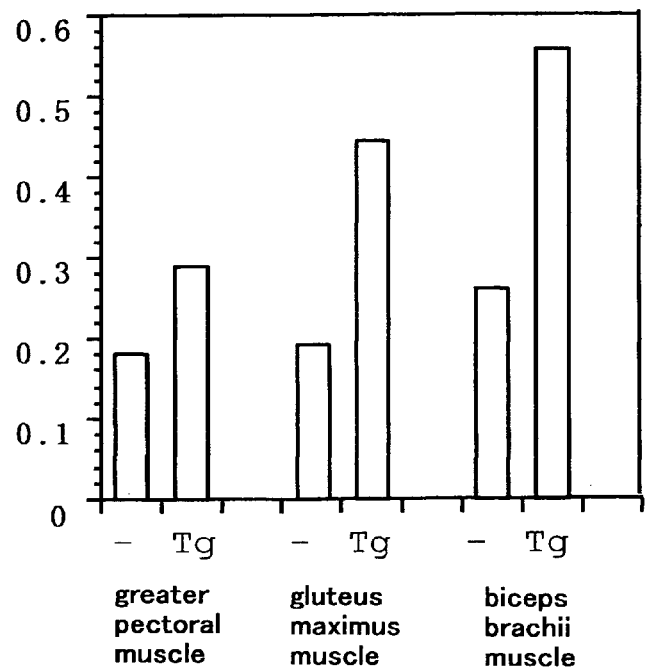
FIG. 19 shows increases in the masses of various skeletal muscles of transgenic mice into which the FS1-1 gene was introduced.

An approximately 3.7-kbp Cla I fragment of MDAF2-FS1-1 was isolated and then microscopically injected into 221 BDF1 mouse fertilized eggs. The fertilized eggs in good condition were transplanted into recipient mice. The mice were caused to naturally deliver progenies, so that 33 progenies were obtained. A transgenic mouse lineage for which successful introduction of the DNA derived from MDAF2-FS1-1 in the genomic DNA had been confirmed was maintained. Such transgenic mice over-express the follistatin variant polypeptide FS1-1 in a manner specific to skeletal muscle due to the myosin light chain promoter. In the thus obtained transgenic mice, clear increases in skeletal muscle were observed. As an example, FIG. 19 shows the results of collecting greater pectoral muscle, gluteus maximus muscle, and biceps brachii muscle from 14-week-old male transgenic mice and wild type mice and then weighing such muscles. Compared with the wild-type mice, in the case of the transgenic mice, the weights of all skeletal muscles measured were increased.

Figure 20:
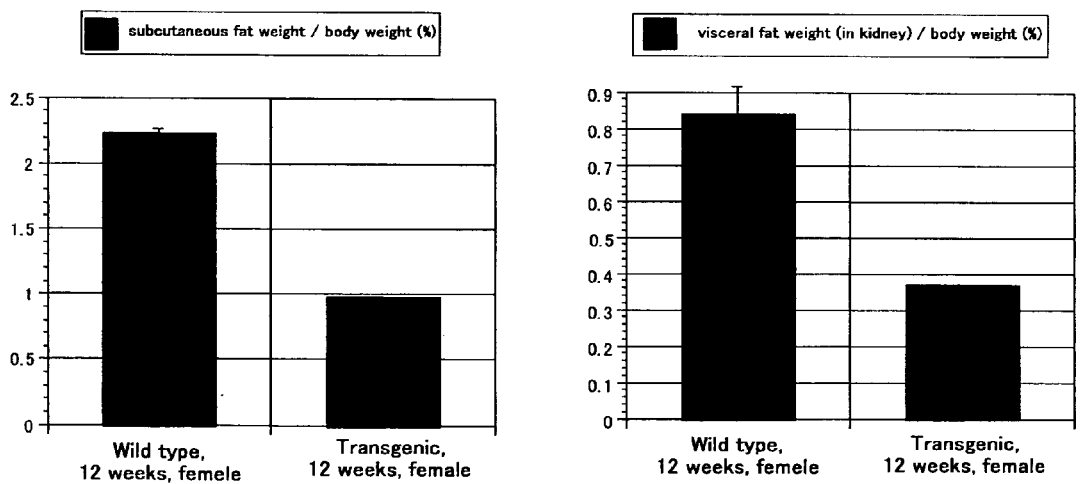
FIG. 20 shows decreases in the proportions of subcutaneous fat weight and visceral fat weight in the kidney to the body weight of a transgenic mouse into which the FS1-1 gene was introduced.

Furthermore, subcutaneous fat and visceral fat levels of the thus obtained transgenic mice were measured so that the effects of the follistatin variant polypeptide on these fat levels were examined. The weight of subcutaneous fat of the inguinal region was measured as subcutaneous fat, and the weight of fat around the kidney was measured as visceral fat. The proportion (%) of each of such weights to each mouse body weight was used as an indicator of fat level. As a result, it was demonstrated that in the case of the transgenic mice, both subcutaneous fat and visceral fat levels had been significantly decreased compared with the case of wild type mice. As an example, FIG. 20 shows the proportion (%) of subcutaneous fat weight to each mouse body weight and the proportion (%) of visceral fat weight to each mouse body weight in the case of a 12-week-old female transgenic mouse and 12-week-old female wild type mice. The results for wild type mice were represented by mean values of the results for all three wild type mice. Moreover, similar to the case of male transgenic mice, significant decreases were observed in subcutaneous fat and visceral fat levels. In addition, in the case of the transgenic mice, abnormalities other than increases in skeletal muscle and decreases in fat were not observed.

Example 5

Inhibition of GDF-8-specific Functions by Fusion Proteins of the Follistatin Variant Polypeptides and an Immunoglobulin Constant Region (1) Construction of Expression Vectors of Fusion Proteins of the Follistatin Variant Polypeptides and an Immunoglobulin Constant Region Expression vectors of fusion proteins each comprised of the follistatin variant polypeptide FS1 or FS1-1 and an immunoglobulin constant region were constructed as follows.

By the use of pGEM-T Easy (B) prepared in Example 1 as a template and 10 pmol each of synthetic DNAs (produced by Genset) having nucleotide sequences shown in SEQ ID NO: 27 and SEQ ID NO: 28, respectively, as primers, PCR was performed under conditions similar to those employed for the gene amplification fragment A in Example 1. The reaction solution was fractionated by agarose gel electrophoresis, so that an FS1-encoding amplification fragment was collected, wherein a Kpn I site had been added to the 5' end and a BamH I site had been added to the 3' end. The thus obtained amplification fragment was digested with Kpn I and BamH I. The product was ligated to a Kpn I-BamH I fragment containing the genome sequence encoding the human IgG1 constant region, which had been obtained by digesting a CD5-IgG1 vector (Cell, 61, 1303 (1990)) with restriction enzymes Kpn I and BamH I. Thus, a fusion protein (hereinafter, referred to as FSI-Fc) expression plasmid pcDNA3 FS1-Fc wherein the human IgG1 constant region had been fused to the C-terminus of FS1 was prepared. In the case of the CD5-IgG1 vector, the sequence encoding the human IgG1 constant region is inserted between Xho I site-Aba I site located downstream of a vector pcDNA3 promoter. Hence, pcDNA3 FS1-Fc has a structure wherein the sequence encoding FS1-Fc has been inserted downstream of the pcDNA3 promoter.

A fragment containing the sequence encoding FS1-1, which had been obtained by digesting pBluscript (A+B) prepared in Example 1 with EcoRI and EcoRV, was inserted between EcoRI site-Sma I site of a vector pSP72 (produced by Promega). A fragment containing the sequence encoding FS1-1, which had been obtained by digesting the thus obtained plasmid with EcoRI and BamHI was inserted between EcoRI site-BamHI site of pBluescript SK(−). A fragment containing the sequence encoding FS1-1, which had been obtained by digesting the thus obtained plasmid with Kpn I and BamH I was ligated to a Kpn I-BamH I fragment containing the genome sequence encoding the human IgG1 constant region, which had been obtained by digesting the CD5-IgG1 vector with restriction enzymes Kpn I and BamHI. Thus, the fusion protein expression plasmid pcDNA3 FS1-1-Fc was prepared (hereinafter, referred to as FS1-1-Fc), wherein a human IgG1 constant region had been fused to the C-terminus of FS1-1. pcDNA3 FS1-1-Fc has a structure wherein the sequence encoding FS1-1-Fc has been inserted downstream of the pcDNA3 promoter.

(2) Transfection of Expression Vectors into CHO-K1 Cells and Culture of the CHO-K1 Cells CHO-K1 (ATCC NO: CCL-61) cells were transfected with pcDNA3 FS1-Fc or pcDNA3 FS1-1-Fc using a liposome reagent Transfast (produced by Promega). Single clones were obtained, into which the introduced genes had been stably incorporated. Each single clone was suspended in 10 ml of an α MEM medium supplemented with 10% FCS and then inoculated on a cell culture dish with a diameter of 10 cm. The cells were cultured to confluency within a 5% $CO_2$ incubator at 37° C. Subsequently, the media were exchanged with EX-CELL 301 media (produced by JRH Biosciences). After 1 week of culture using 6 cell culture dishes, approximately 60 ml of each culture supernatant was collected.

(3) Purification of FS1-Fc and FS1-1-Fc

To the culture supernatant of CHO-K1 cells obtained in (2) expressing FS1-Fc or FS1-1-Fc, heparin cellulofine (produced by Seikagaku Corporation) was added in an amount one-tenth of that of the culture supernatant. The resultants were mixed for 2 hours at room temperature, so as to cause proteins to be adsorbed. The heparin cellulofine was washed with a washing buffer (20 mmmol/L Tris-HCl (pH 7.4) and 0.15 mol/L NaCl) and then the adsorbed proteins were eluted using an elution buffer (20 mmmol/L Tris-HCl (pH 7.4) and 1.5 mol/L NaCl). An FS1-Fc solution and an FS1-1-Fc solution were each obtained from the obtained eluates according to a standard method using a resin to which protein A specifically binding to the immunoglobulin constant region had been immobilized.

Figure 21:
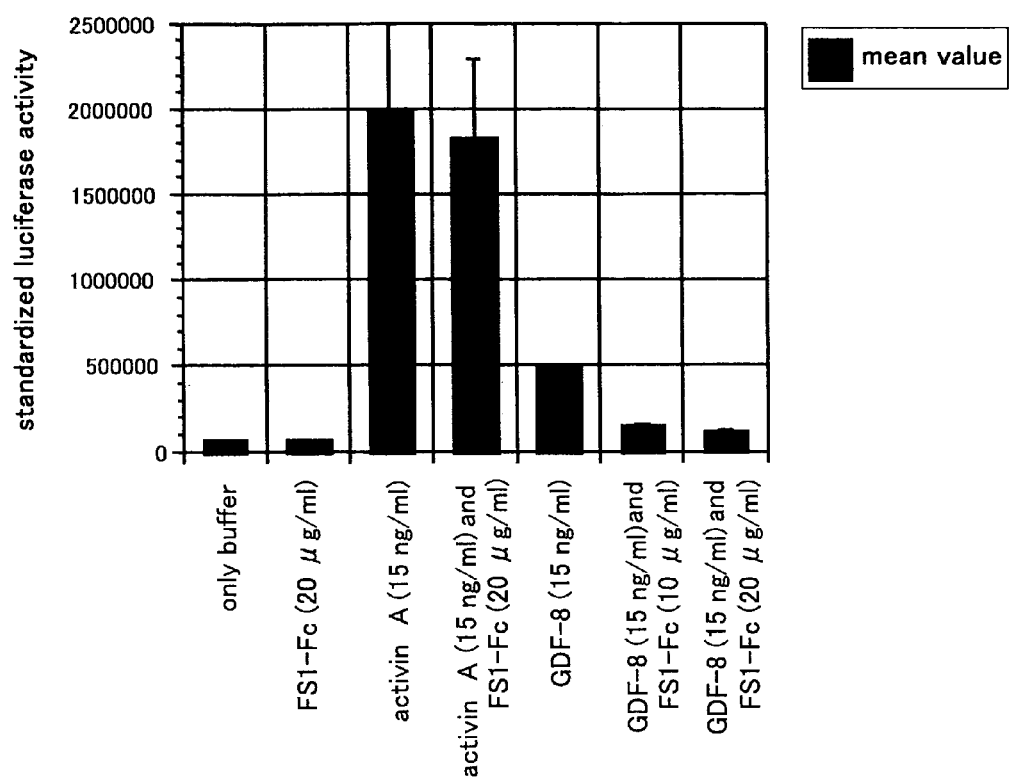
FIG. 21 shows the results of reporter assay to measure the inhibition of activin activity and GDF-8 activity by FS1-Fc.

(4) Assay of Activity of FS1-Fc and FS1-1-Fc to Inhibit Activin Functions and GDF-8 Functions Under conditions of (a) a buffer alone, (b) FS1-Fc (20 μg/ml), (c) activin (15 ng/ml), (d) activin (15 ng/ml) and FS1-Fc (20 μg/ml), (e) GDF-8 (15 ng/ml), (f) GDF-8 (15 ng/ml) and FS1-Fc (10 μg/ml), or (g) GDF-8 (15 ng/ml) and FS1-Fc (20 μg/ml), the activity of FS1-Fc to inhibit activin functions and GDF-8 functions was assayed by reporter assay in a manner similar to that in Example 3. As shown in FIG. 21, FS1-Fc almost completely inhibited elevation in standardized luciferase activity due to GDF-8, but almost never inhibited elevation in standardized luciferase activity due to activin.

Figure 22:
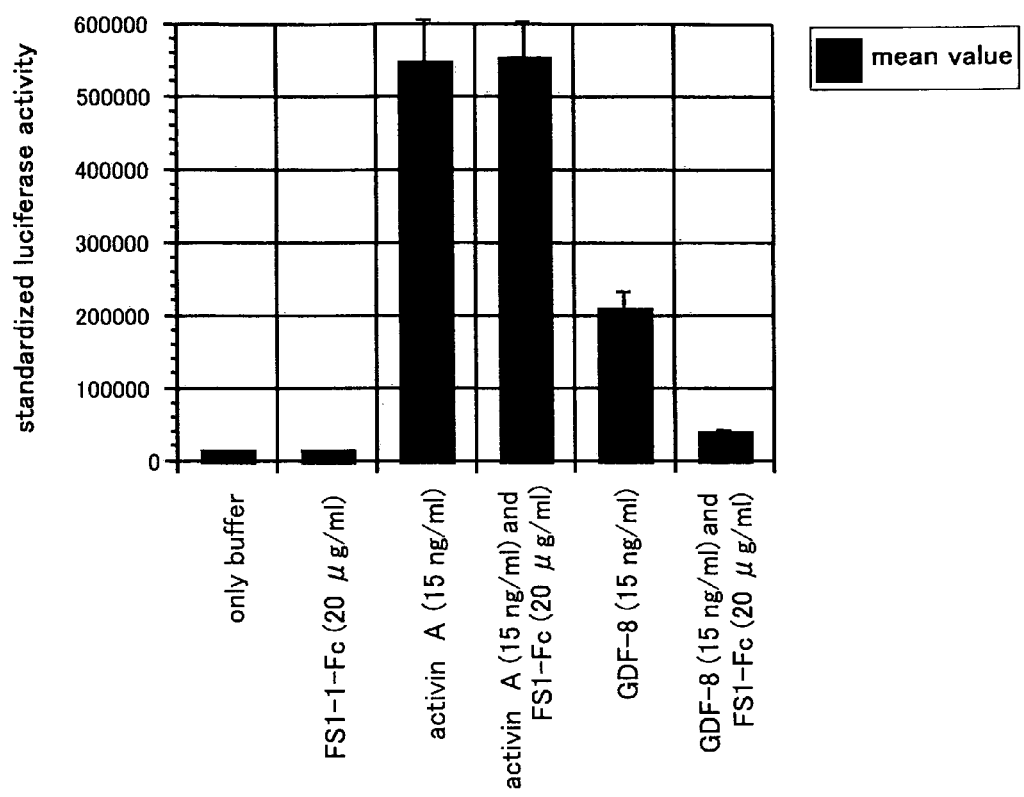
FIG. 22 shows the results of reporter assay to measure the inhibition of activin activity and GDF-8 activity by FS1-1-Fc.

Similarly, under conditions of (a) a buffer alone, (b) FS1-1-Fc (20 μg/ml), (c) activin (15 ng/ml), (d) activin (15 ng/ml) and FS1-1-Fc (20 μg/ml), (e) GDF-8 (15 ng/ml), or (f) GDF-8 (15 ng/ml) and FS1-1-Fc (20 μg/ml), the activity of FS1-1-Fc to inhibit activin functions and GDF-8 functions was assayed. As shown in FIG. 22, FS1-1-Fc almost completely inhibited elevation in standardized luciferase activity due to GDF-8, but almost never inhibited elevation in standardized luciferase activity due to activin.

As described above, it was confirmed that FS1-Fc or FS1-1-Fc, the fusion protein of the follistatin variant polypeptide and the immunoglobulin constant region, can selectively inhibit GDF-8 activity, similarly to the cases of FS1 and FS1-1.

INDUSTRIAL APPLICABILITY

According to the present invention, a follistatin variant polypeptide that selectively inhibits GDF-8 activity as compared with its inhibition of activin activity is provided. This follistatin variant polypeptide can be used for increasing skeletal muscle and decreasing fat. Furthermore, the follistatin variant polypeptide can also be used for treating amyotrophic symptoms, cachexia, disease accompanied by muscular atrophy, Type II diabetes, obesity, and acquired immunodeficiency syndrome.

The invention claimed is:

1. A follistatin variant polypeptide, which
   (a) comprises any one domain structure selected from FSI-FSI, FSI-FSI-FSIII, FSN-FSI-FSI, and FSN-FSI-FSI-FSIII, wherein
      FSI denotes follistatin domain I comprising SEQ ID NO: 1 or amino acids 95-164 of SEQ ID NO: 4,
      FSIII denotes follistatin domain III comprising amino acids 245-316 of SEQ ID NO: 4, and
      FSN denotes an N-terminal domain comprising amino acids 1-94 of SEQ ID NO: 4, and
   the domains are each linked directly or via a linker polypeptide, wherein the linker polypeptide contains no cysteines and the length of the linker polypeptide is 1-10 amino acids;
   (b) does not comprise an amino acid sequence that is represented by formula (I): Cys-$(X^1)_a$-Cys-$(X^2)_b$-Cys-$(X^3)_c$-Cys-$(X^4)_d$-Cys-$(X^5)_e$-Cys-$(X^6)_f$-Cys-$(X^7)_g$-Cys-$(X^8)_h$-Cys-$(X^9)_i$-Cys (SEQ ID NO: 30) wherein $X^1$, $X^2$, $X^3$, $X^4$, $X^5$, $X^6$, $X^7$, $X^8$, and $X^9$ each independently represents the same or a different naturally occurring amino acid residue other than cysteine, "a" represents an integer between 2 and 6, "b" represents an integer between 3 and 7, "c" represents an integer between 7 and 11, "d" represents an integer between 0 and 4, "e" represents an integer between 1 and 6, "f" and "g" represent integers between 8 and 12, "h" represents an integer between 4 and 8, and "i" represents an integer between 11 and 15 and has 50% or more homology with the amino acid sequence of SEQ ID NO: 2 or SEQ ID NO: 29; and
   (c) selectively inhibits GDF-8 activity as compared with its inhibition of activin activity.

2. The follistatin variant polypeptide according to claim 1, which
comprises any one domain structure selected from FSI-FSI and FSN-FSI-FSI.

3. The follistatin variant polypeptide according to claim 1, which comprises the amino acid sequence ranging from the 30$^{th}$ to the 166$^{th}$ amino acids of SEQ ID NO: 4.

4. The follistatin variant polypeptide according to claim 1, wherein another polypeptide is fused thereto.

5. A pharmaceutical composition, which comprises the polypeptide according to claim 1, and further comprises a pharmaceutically acceptable carrier.

6. The follistatin variant polypeptide according to claim 1, wherein the length of the linker polypeptide is 1-5 amino acids.

7. A polypeptide, which comprises the amino acid sequence of SEQ ID NO: 6, 8 or 10.

8. A polypeptide according to claim 7, which comprises the amino acid sequence of SEQ ID NO: 6 or 10.

SEQUENCE LISTING

<160> NUMBER OF SEQ ID NOS: 40

<210> SEQ ID NO 1
<211> LENGTH: 70
<212> TYPE: PRT
<213> ORGANISM: Artificial Sequence
<220> FEATURE:
<223> OTHER INFORMATION: Description of Artificial Sequence: Synthetic
      follistatin domain I consensus sequence
<220> FEATURE:
<221> NAME/KEY: modified_base
<222> LOCATION: (2)
<223> OTHER INFORMATION: Glu or Asp
<220> FEATURE:
<221> NAME/KEY: modified_base
<222> LOCATION: (13)
<223> OTHER INFORMATION: Arg or Lys
<220> FEATURE:
<221> NAME/KEY: modified_base
<222> LOCATION: (69)
<223> OTHER INFORMATION: Lys or Arg

<400> SEQUENCE: 1

Cys Xaa Asn Val Asp Cys Gly Pro Gly Lys Lys Cys Xaa Met Asn Lys
 1               5                  10                  15

Lys Asn Lys Pro Arg Cys Val Cys Ala Pro Asp Cys Ser Asn Ile Thr
            20                  25                  30

Trp Lys Gly Pro Val Cys Gly Leu Asp Gly Lys Thr Tyr Arg Asn Glu
        35                  40                  45

Cys Ala Leu Leu Lys Ala Arg Cys Lys Glu Gln Pro Glu Leu Glu Val
    50                  55                  60

Gln Tyr Gln Gly Xaa Cys
 65                  70

<210> SEQ ID NO 2
<211> LENGTH: 72
<212> TYPE: PRT
<213> ORGANISM: Artificial Sequence
<220> FEATURE:
<223> OTHER INFORMATION: Description of Artificial Sequence: Synthetic
<220> FEATURE:
<221> NAME/KEY: modified_base
<222> LOCATION: (5)
<223> OTHER INFORMATION: any naturally occurring amino acid except Cys
<220> FEATURE:
<221> NAME/KEY: modified_base
<222> LOCATION: (33)
<223> OTHER INFORMATION: any naturally occurring amino acid except Cys
<220> FEATURE:
<221> NAME/KEY: modified_base
<222> LOCATION: (35)
<223> OTHER INFORMATION: any naturally occurring amino acid except Cys
<220> FEATURE:
<221> NAME/KEY: modified_base
<222> LOCATION: (38)
<223> OTHER INFORMATION: any naturally occurring amino acid except Cys
<220> FEATURE:
<221> NAME/KEY: modified_base
<222> LOCATION: (45)
<223> OTHER INFORMATION: any naturally occurring amino acid except Cys
<220> FEATURE:
<221> NAME/KEY: modified_base
<222> LOCATION: (48)
<223> OTHER INFORMATION: any naturally occurring amino acid except Cys

<400> SEQUENCE: 2

Cys Arg Asp Val Xaa Cys Pro Gly Ser Ser Thr Cys Val Val Asp Gln
 1               5                  10                  15

```
                Thr Asn Asn Ala Tyr Cys Val Thr Cys Asn Arg Ile Cys Pro Glu Pro
                             20                  25                  30

Xaa Ser Xaa Glu Gln Xaa Leu Cys Gly Asn Asp Gly Xaa Thr Tyr Xaa
                             35                  40                  45

Ser Ala Cys His Leu Arg Lys Ala Thr Cys Leu Leu Gly Arg Ser Ile
                             50                  55                  60

Gly Leu Ala Tyr Glu Gly Lys Cys
                 65                  70
```

<210> SEQ ID NO 3
<211> LENGTH: 1035
<212> TYPE: DNA
<213> ORGANISM: Homo sapiens
<220> FEATURE:
<221> NAME/KEY: CDS
<222> LOCATION: (1)..(1035)

<400> SEQUENCE: 3

```
atg gtc cgc gcg agg cac cag ccg ggt ggg ctt tgc ctc ctg ctg ctg         48
Met Val Arg Ala Arg His Gln Pro Gly Gly Leu Cys Leu Leu Leu Leu
 1               5                  10                  15 ctc ctc tgc cag ttc atg gag gac cgc agt gcc cag gct ggg aac tgc         96
Leu Leu Cys Gln Phe Met Glu Asp Arg Ser Ala Gln Ala Gly Asn Cys
             20                  25                  30 tgg ctc cgt caa gcg aag aac ggc cgc tgc cag gtc ctg tac aag acc        144
Trp Leu Arg Gln Ala Lys Asn Gly Arg Cys Gln Val Leu Tyr Lys Thr
         35                  40                  45 gaa ctg agc aag gag gag tgc tgc agc acc ggc cgg ctg agc acc tcg        192
Glu Leu Ser Lys Glu Glu Cys Cys Ser Thr Gly Arg Leu Ser Thr Ser
     50                  55                  60 tgg acc gag gag gac gtg aat gac aac aca ctc ttc aag tgg atg att        240
Trp Thr Glu Glu Asp Val Asn Asp Asn Thr Leu Phe Lys Trp Met Ile
 65                  70                  75                  80 ttc aac ggg ggc gcc ccc aac tgc atc ccc tgt aaa gaa acg tgt gag        288
Phe Asn Gly Gly Ala Pro Asn Cys Ile Pro Cys Lys Glu Thr Cys Glu
                 85                  90                  95 aac gtg gac tgt gga cct ggg aaa aaa tgc cga atg aac aag aag aac        336
Asn Val Asp Cys Gly Pro Gly Lys Lys Cys Arg Met Asn Lys Lys Asn
            100                 105                 110 aaa ccc cgc tgc gtc tgc gcc ccg gat tgt tcc aac atc acc tgg aag        384
Lys Pro Arg Cys Val Cys Ala Pro Asp Cys Ser Asn Ile Thr Trp Lys
        115                 120                 125 ggt cca gtc tgc ggg ctg gat ggg aaa acc tac cgc aat gaa tgt gca        432
Gly Pro Val Cys Gly Leu Asp Gly Lys Thr Tyr Arg Asn Glu Cys Ala
    130                 135                 140 ctc cta aag gca aga tgt aaa gag cag cca gaa ctg gaa gtc cag tac        480
Leu Leu Lys Ala Arg Cys Lys Glu Gln Pro Glu Leu Glu Val Gln Tyr
145                 150                 155                 160 caa ggc aga tgt aaa aag act tgt cgg gat gtt ttc tgt cca ggc agc        528
Gln Gly Arg Cys Lys Lys Thr Cys Arg Asp Val Phe Cys Pro Gly Ser
                165                 170                 175 tcc aca tgt gtg gtg gac cag acc aat aat gcc tac tgt gtg acc tgt        576
Ser Thr Cys Val Val Asp Gln Thr Asn Asn Ala Tyr Cys Val Thr Cys
            180                 185                 190 aat cgg att tgc cca gag cct gct tcc tct gag caa tat ctc tgt ggg        624
Asn Arg Ile Cys Pro Glu Pro Ala Ser Ser Glu Gln Tyr Leu Cys Gly
        195                 200                 205 aat gat gga gtc acc tac tcc agt gcc tgc cac ctg aga aag gct acc        672
Asn Asp Gly Val Thr Tyr Ser Ser Ala Cys His Leu Arg Lys Ala Thr
    210                 215                 220
```

-continued

```
tgc ctg ctg ggc aga tct att gga tta gcc tat gag gga aag tgt atc    720
Cys Leu Leu Gly Arg Ser Ile Gly Leu Ala Tyr Glu Gly Lys Cys Ile
225                 230                 235                 240 aaa gca aag tcc tgt gaa gat atc cag tgc act ggt ggg aaa aaa tgt    768
Lys Ala Lys Ser Cys Glu Asp Ile Gln Cys Thr Gly Gly Lys Lys Cys
            245                 250                 255 tta tgg gat ttc aag gtt ggg aga ggc cgg tgt tcc ctc tgt gat gag    816
Leu Trp Asp Phe Lys Val Gly Arg Gly Arg Cys Ser Leu Cys Asp Glu
        260                 265                 270 ctg tgc cct gac agt aag tcg gat gag cct gtc tgt gcc agt gac aat    864
Leu Cys Pro Asp Ser Lys Ser Asp Glu Pro Val Cys Ala Ser Asp Asn
    275                 280                 285 gcc act tat gcc agc gag tgt gcc atg aag gaa gct gcc tgc tcc tca    912
Ala Thr Tyr Ala Ser Glu Cys Ala Met Lys Glu Ala Ala Cys Ser Ser
290                 295                 300 ggt gtg cta ctg gaa gta aag cac tcc gga tct tgc aac tcc att tcg    960
Gly Val Leu Leu Glu Val Lys His Ser Gly Ser Cys Asn Ser Ile Ser
305                 310                 315                 320 gaa gac acc gag gaa gag gag gaa gat gaa gac cag gac tac agc ttt   1008
Glu Asp Thr Glu Glu Glu Glu Asp Glu Asp Gln Asp Tyr Ser Phe
            325                 330                 335 cct ata tct tct att cta gag tgg taa                                1035
Pro Ile Ser Ser Ile Leu Glu Trp
        340
```

<210> SEQ ID NO 4
<211> LENGTH: 344
<212> TYPE: PRT
<213> ORGANISM: Homo sapiens

<400> SEQUENCE: 4

```
Met Val Arg Ala Arg His Gln Pro Gly Gly Leu Cys Leu Leu Leu Leu
 1               5                  10                  15

Leu Leu Cys Gln Phe Met Glu Asp Arg Ser Ala Gln Ala Gly Asn Cys
            20                  25                  30

Trp Leu Arg Gln Ala Lys Asn Gly Arg Cys Gln Val Leu Tyr Lys Thr
        35                  40                  45

Glu Leu Ser Lys Glu Glu Cys Cys Ser Thr Gly Arg Leu Ser Thr Ser
    50                  55                  60

Trp Thr Glu Glu Asp Val Asn Asp Asn Thr Leu Phe Lys Trp Met Ile
65                  70                  75                  80

Phe Asn Gly Gly Ala Pro Asn Cys Ile Pro Cys Lys Glu Thr Cys Glu
                85                  90                  95

Asn Val Asp Cys Gly Pro Gly Lys Lys Cys Arg Met Asn Lys Lys Asn
            100                 105                 110

Lys Pro Arg Cys Val Cys Ala Pro Asp Cys Ser Asn Ile Thr Trp Lys
        115                 120                 125

Gly Pro Val Cys Gly Leu Asp Gly Lys Thr Tyr Arg Asn Glu Cys Ala
    130                 135                 140

Leu Leu Lys Ala Arg Cys Lys Glu Gln Pro Glu Leu Glu Val Gln Tyr
145                 150                 155                 160

Gln Gly Arg Cys Lys Lys Thr Cys Arg Asp Val Phe Cys Pro Gly Ser
                165                 170                 175

Ser Thr Cys Val Val Asp Gln Thr Asn Asn Ala Tyr Cys Val Thr Cys
            180                 185                 190

Asn Arg Ile Cys Pro Glu Pro Ala Ser Ser Glu Gln Tyr Leu Cys Gly
        195                 200                 205
```

-continued

```
Asn Asp Gly Val Thr Tyr Ser Ser Ala Cys His Leu Arg Lys Ala Thr
    210                 215                 220
Cys Leu Leu Gly Arg Ser Ile Gly Leu Ala Tyr Glu Gly Lys Cys Ile
225                 230                 235                 240
Lys Ala Lys Ser Cys Glu Asp Ile Gln Cys Thr Gly Lys Lys Cys
                245                 250                 255
Leu Trp Asp Phe Lys Val Gly Arg Gly Arg Cys Ser Leu Cys Asp Glu
            260                 265                 270
Leu Cys Pro Asp Ser Lys Ser Asp Glu Pro Val Cys Ala Ser Asp Asn
        275                 280                 285
Ala Thr Tyr Ala Ser Glu Cys Ala Met Lys Glu Ala Ala Cys Ser Ser
    290                 295                 300
Gly Val Leu Leu Glu Val Lys His Ser Gly Ser Cys Asn Ser Ile Ser
305                 310                 315                 320
Glu Asp Thr Glu Glu Glu Glu Asp Gly Asp Gln Asp Tyr Ser Phe
            325                 330                 335
Pro Ile Ser Ser Ile Leu Glu Trp
            340
```

<210> SEQ ID NO 5
<211> LENGTH: 678
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<221> NAME/KEY: CDS
<222> LOCATION: (1)..(678)

<400> SEQUENCE: 5

```
ggg aac tgc tgg ctc cgt caa gcg aag aac ggc cgc tgc cag gtc ctg      48
Gly Asn Cys Trp Leu Arg Gln Ala Lys Asn Gly Arg Cys Gln Val Leu
  1               5                  10                  15 tac aag acc gaa ctg agc aag gag gag tgc tgc agc acc ggc cgg ctg      96
Tyr Lys Thr Glu Leu Ser Lys Glu Glu Cys Cys Ser Thr Gly Arg Leu
             20                  25                  30 agc acc tcg tgg acc gag gag gac gtg aat gac aac aca ctc ttc aag     144
Ser Thr Ser Trp Thr Glu Glu Asp Val Asn Asp Asn Thr Leu Phe Lys
         35                  40                  45 tgg atg att ttc aac ggg ggc gcc ccc aac tgc atc ccc tgt aaa gaa     192
Trp Met Ile Phe Asn Gly Gly Ala Pro Asn Cys Ile Pro Cys Lys Glu
     50                  55                  60 acg tgt gag aac gtg gac tgt gga cct ggg aaa aaa tgc cga atg aac     240
Thr Cys Glu Asn Val Asp Cys Gly Pro Gly Lys Lys Cys Arg Met Asn
 65                  70                  75                  80 aag aag aac aaa ccc cgc tgc gtc tgc gcc ccg gat tgt tcc aac atc     288
Lys Lys Asn Lys Pro Arg Cys Val Cys Ala Pro Asp Cys Ser Asn Ile
                 85                  90                  95 acc tgg aag ggt cca gtc tgc ggg ctg gat ggg aaa acc tac cgc aat     336
Thr Trp Lys Gly Pro Val Cys Gly Leu Asp Gly Lys Thr Tyr Arg Asn
            100                 105                 110 gaa tgt gca ctc cta aag gca aga tgt aaa gag cag cca gaa ctg gaa     384
Glu Cys Ala Leu Leu Lys Ala Arg Cys Lys Glu Gln Pro Glu Leu Glu
        115                 120                 125 gtc cag tac caa ggc aga tgt aaa aag ctt tgt gag aac gtg gac tgt     432
Val Gln Tyr Gln Gly Arg Cys Lys Lys Leu Cys Glu Asn Val Asp Cys
    130                 135                 140 gga cct ggg aaa aaa tgc cga atg aac aag aag aac aaa ccc cgc tgc     480
Gly Pro Gly Lys Lys Cys Arg Met Asn Lys Lys Asn Lys Pro Arg Cys
```

```
                                                                                     -continued
145                 150                 155                 160
gtc tgc gcc ccg gat tgt tcc aac atc acc tgg aag ggt cca gtc tgc          528
Val Cys Ala Pro Asp Cys Ser Asn Ile Thr Trp Lys Gly Pro Val Cys
                165                 170                 175 ggg ctg gat ggg aaa acc tac cgc aat gaa tgt gca ctc cta aag gca          576
Gly Leu Asp Gly Lys Thr Tyr Arg Asn Glu Cys Ala Leu Leu Lys Ala
            180                 185                 190 aga tgt aaa gag cag cca gaa ctg gaa gtc cag tac caa ggc aga tgt          624
Arg Cys Lys Glu Gln Pro Glu Leu Glu Val Gln Tyr Gln Gly Arg Cys
        195                 200                 205 aaa aag act tgt gaa gat atc tcg agg caa tca cta gag ggc cct att          672
Lys Lys Thr Cys Glu Asp Ile Ser Arg Gln Ser Leu Glu Gly Pro Ile
    210                 215                 220 cta tag                                                                   678
Leu
225

<210> SEQ ID NO 6
<211> LENGTH: 225
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Gly Asn Cys Trp Leu Arg Gln Ala Lys Asn Gly Arg Cys Gln Val Leu
 1               5                  10                  15

Tyr Lys Thr Glu Leu Ser Lys Glu Glu Cys Cys Ser Thr Gly Arg Leu
            20                  25                  30

Ser Thr Ser Trp Thr Glu Glu Asp Val Asn Asp Asn Thr Leu Phe Lys
        35                  40                  45

Trp Met Ile Phe Asn Gly Gly Ala Pro Asn Cys Ile Pro Cys Lys Glu
    50                  55                  60

Thr Cys Glu Asn Val Asp Cys Gly Pro Gly Lys Lys Cys Arg Met Asn
65                  70                  75                  80

Lys Lys Asn Lys Pro Arg Cys Val Cys Ala Pro Asp Cys Ser Asn Ile
                85                  90                  95

Thr Trp Lys Gly Pro Val Cys Gly Leu Asp Gly Lys Thr Tyr Arg Asn
            100                 105                 110

Glu Cys Ala Leu Leu Lys Ala Arg Cys Lys Glu Gln Pro Glu Leu Glu
        115                 120                 125

Val Gln Tyr Gln Gly Arg Cys Lys Lys Leu Cys Glu Asn Val Asp Cys
    130                 135                 140

Gly Pro Gly Lys Lys Cys Arg Met Asn Lys Lys Asn Lys Pro Arg Cys
145                 150                 155                 160

Val Cys Ala Pro Asp Cys Ser Asn Ile Thr Trp Lys Gly Pro Val Cys
                165                 170                 175

Gly Leu Asp Gly Lys Thr Tyr Arg Asn Glu Cys Ala Leu Leu Lys Ala
            180                 185                 190

Arg Cys Lys Glu Gln Pro Glu Leu Glu Val Gln Tyr Gln Gly Arg Cys
        195                 200                 205

Lys Lys Thr Cys Glu Asp Ile Ser Arg Gln Ser Leu Glu Gly Pro Ile
    210                 215                 220

Leu
225
```

<210> SEQ ID NO 7
<211> LENGTH: 480
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<221> NAME/KEY: CDS
<222> LOCATION: (1)..(480)

<400> SEQUENCE: 7

```
ggg aac tgc tgg ctc cgt caa gcg aag aac ggc cgc tgc cag gtc ctg      48
Gly Asn Cys Trp Leu Arg Gln Ala Lys Asn Gly Arg Cys Gln Val Leu
  1               5                  10                  15 tac aag acc gaa ctg agc aag gag gag tgc tgc agc acc ggc cgg ctg      96
Tyr Lys Thr Glu Leu Ser Lys Glu Glu Cys Cys Ser Thr Gly Arg Leu
             20                  25                  30 agc acc tcg tgg acc gag gag gac gtg aat gac aac aca ctc ttc aag     144
Ser Thr Ser Trp Thr Glu Glu Asp Val Asn Asp Asn Thr Leu Phe Lys
         35                  40                  45 tgg atg att ttc aac ggg ggc gcc ccc aac tgc atc ccc tgt aaa gaa     192
Trp Met Ile Phe Asn Gly Gly Ala Pro Asn Cys Ile Pro Cys Lys Glu
     50                  55                  60 acg tgt gag aac gtg gac tgt gga cct ggg aaa aaa tgc cga atg aac     240
Thr Cys Glu Asn Val Asp Cys Gly Pro Gly Lys Lys Cys Arg Met Asn
 65                  70                  75                  80 aag aag aac aaa ccc cgc tgc gtc tgc gcc ccg gat tgt tcc aac atc     288
Lys Lys Asn Lys Pro Arg Cys Val Cys Ala Pro Asp Cys Ser Asn Ile
                 85                  90                  95 acc tgg aag ggt cca gtc tgc ggg ctg gat ggg aaa acc tac cgc aat     336
Thr Trp Lys Gly Pro Val Cys Gly Leu Asp Gly Lys Thr Tyr Arg Asn
            100                 105                 110 gaa tgt gca ctc cta aag gca aga tgt aaa gag cag cca gaa ctg gaa     384
Glu Cys Ala Leu Leu Lys Ala Arg Cys Lys Glu Gln Pro Glu Leu Glu
        115                 120                 125 gtc cag tac caa ggc aga tgt aaa aag ctt atc gat acc gtc gac ctc     432
Val Gln Tyr Gln Gly Arg Cys Lys Lys Leu Ile Asp Thr Val Asp Leu
    130                 135                 140 gag cat gca tct aga ggg ccc tat tct ata gtg tca cct aaa tgc tag     480
Glu His Ala Ser Arg Gly Pro Tyr Ser Ile Val Ser Pro Lys Cys
145                 150                 155
```

<210> SEQ ID NO 8
<211> LENGTH: 159
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 8

```
Gly Asn Cys Trp Leu Arg Gln Ala Lys Asn Gly Arg Cys Gln Val Leu
  1               5                  10                  15

Tyr Lys Thr Glu Leu Ser Lys Glu Glu Cys Cys Ser Thr Gly Arg Leu
             20                  25                  30

Ser Thr Ser Trp Thr Glu Glu Asp Val Asn Asp Asn Thr Leu Phe Lys
         35                  40                  45

Trp Met Ile Phe Asn Gly Gly Ala Pro Asn Cys Ile Pro Cys Lys Glu
     50                  55                  60

Thr Cys Glu Asn Val Asp Cys Gly Pro Gly Lys Lys Cys Arg Met Asn
 65                  70                  75                  80
```

-continued

```
Lys Lys Asn Lys Pro Arg Cys Val Cys Ala Pro Asp Cys Ser Asn Ile
            85                  90                  95

Thr Trp Lys Gly Pro Val Cys Gly Leu Asp Gly Lys Thr Tyr Arg Asn
        100                 105                 110

Glu Cys Ala Leu Leu Lys Ala Arg Cys Lys Glu Gln Pro Glu Leu Glu
            115                 120                 125

Val Gln Tyr Gln Gly Arg Cys Lys Lys Leu Ile Asp Thr Val Asp Leu
    130                 135                 140

Glu His Ala Ser Arg Gly Pro Tyr Ser Ile Val Ser Pro Lys Cys
145                 150                 155

<210> SEQ ID NO 9
<211> LENGTH: 936
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(936)

<400> SEQUENCE: 9 ggg aac tgc tgg ctc cgt caa gcg aag aac ggc cgc tgc cag gtc ctg      48
Gly Asn Cys Trp Leu Arg Gln Ala Lys Asn Gly Arg Cys Gln Val Leu
  1               5                  10                  15 tac aag acc gaa ctg agc aag gag gag tgc tgc agc acc ggc cgg ctg      96
Tyr Lys Thr Glu Leu Ser Lys Glu Glu Cys Cys Ser Thr Gly Arg Leu
             20                  25                  30 agc acc tcg tgg acc gag gag gac gtg aat gac aac aca ctc ttc aag     144
Ser Thr Ser Trp Thr Glu Glu Asp Val Asn Asp Asn Thr Leu Phe Lys
         35                  40                  45 tgg atg att ttc aac ggg ggc gcc ccc aac tgc atc ccc tgt aaa gaa     192
Trp Met Ile Phe Asn Gly Gly Ala Pro Asn Cys Ile Pro Cys Lys Glu
     50                  55                  60 acg tgt gag aac gtg gac tgt gga cct ggg aaa aaa tgc cga atg aac     240
Thr Cys Glu Asn Val Asp Cys Gly Pro Gly Lys Lys Cys Arg Met Asn
 65                  70                  75                  80 aag aag aac aaa ccc cgc tgc gtc tgc gcc ccg gat tgt tcc aac atc     288
Lys Lys Asn Lys Pro Arg Cys Val Cys Ala Pro Asp Cys Ser Asn Ile
                 85                  90                  95 acc tgg aag ggt cca gtc tgc ggg ctg gat ggg aaa acc tac cgc aat     336
Thr Trp Lys Gly Pro Val Cys Gly Leu Asp Gly Lys Thr Tyr Arg Asn
            100                 105                 110 gaa tgt gca ctc cta aag gca aga tgt aaa gag cag cca gaa ctg gaa     384
Glu Cys Ala Leu Leu Lys Ala Arg Cys Lys Glu Gln Pro Glu Leu Glu
        115                 120                 125 gtc cag tac caa ggc aga tgt aaa aag ctt tgt gag aac gtg gac tgt     432
Val Gln Tyr Gln Gly Arg Cys Lys Lys Leu Cys Glu Asn Val Asp Cys
    130                 135                 140 gga cct ggg aaa aaa tgc cga atg aac aag aag aac aaa ccc cgc tgc     480
Gly Pro Gly Lys Lys Cys Arg Met Asn Lys Lys Asn Lys Pro Arg Cys
145                 150                 155                 160 gtc tgc gcc ccg gat tgt tcc aac atc acc tgg aag ggt cca gtc tgc     528
Val Cys Ala Pro Asp Cys Ser Asn Ile Thr Trp Lys Gly Pro Val Cys
                165                 170                 175 ggg ctg gat ggg aaa acc tac cgc aat gaa tgt gca ctc cta aag gca     576
Gly Leu Asp Gly Lys Thr Tyr Arg Asn Glu Cys Ala Leu Leu Lys Ala
            180                 185                 190 aga tgt aaa gag cag cca gaa ctg gaa gtc cag tac caa ggc aga tgt     624
Arg Cys Lys Glu Gln Pro Glu Leu Glu Val Gln Tyr Gln Gly Arg Cys
```

```
                  195                 200                  205
aaa aag act tgt gaa gat atc cag tgc act ggt ggg aaa aaa tgt tta    672
Lys Lys Thr Cys Glu Asp Ile Gln Cys Thr Gly Gly Lys Lys Cys Leu
    210                 215                 220 tgg gat ttc aag gtt ggg aga ggc cgg tgt tcc ctc tgt gat gag ctg    720
Trp Asp Phe Lys Val Gly Arg Gly Arg Cys Ser Leu Cys Asp Glu Leu
225                 230                 235                 240 tgc cct gac agt aag tcg gat gag cct gtc tgt gcc agt gac aat gcc    768
Cys Pro Asp Ser Lys Ser Asp Glu Pro Val Cys Ala Ser Asp Asn Ala
                245                 250                 255 act tat gcc agc gag tgt gcc atg aag gaa gct gcc tgc tcc tca ggt    816
Thr Tyr Ala Ser Glu Cys Ala Met Lys Glu Ala Ala Cys Ser Ser Gly
            260                 265                 270 gtg cta ctg gaa gta aag cac tcc gga tct tgc aac tcc att tcg gaa    864
Val Leu Leu Glu Val Lys His Ser Gly Ser Cys Asn Ser Ile Ser Glu
        275                 280                 285 gac acc gag gaa gag gag gaa gat gaa gac cag gac tac agc ttt cct    912
Asp Thr Glu Glu Glu Glu Glu Asp Glu Asp Gln Asp Tyr Ser Phe Pro
    290                 295                 300 ata tct tct att cta gag tgg taa                                    936
Ile Ser Ser Ile Leu Glu Trp
305                 310

<210> SEQ ID NO 10
<211> LENGTH: 311
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Gly Asn Cys Trp Leu Arg Gln Ala Lys Asn Gly Arg Cys Gln Val Leu
 1               5                  10                  15

Tyr Lys Thr Glu Leu Ser Lys Glu Glu Cys Cys Ser Thr Gly Arg Leu
            20                  25                  30

Ser Thr Ser Trp Thr Glu Glu Asp Val Asn Asp Asn Thr Leu Phe Lys
        35                  40                  45

Trp Met Ile Phe Asn Gly Gly Ala Pro Asn Cys Ile Pro Cys Lys Glu
    50                  55                  60

Thr Cys Glu Asn Val Asp Cys Gly Pro Gly Lys Lys Cys Arg Met Asn
65                  70                  75                  80

Lys Lys Asn Lys Pro Arg Cys Val Cys Ala Pro Asp Cys Ser Asn Ile
                85                  90                  95

Thr Trp Lys Gly Pro Val Cys Gly Leu Asp Gly Lys Thr Tyr Arg Asn
            100                 105                 110

Glu Cys Ala Leu Leu Lys Ala Arg Cys Lys Glu Gln Pro Glu Leu Glu
        115                 120                 125

Val Gln Tyr Gln Gly Arg Cys Lys Lys Leu Cys Glu Asn Val Asp Cys
    130                 135                 140

Gly Pro Gly Lys Lys Cys Arg Met Asn Lys Lys Asn Lys Pro Arg Cys
145                 150                 155                 160

Val Cys Ala Pro Asp Cys Ser Asn Ile Thr Trp Lys Gly Pro Val Cys
                165                 170                 175

Gly Leu Asp Gly Lys Thr Tyr Arg Asn Glu Cys Ala Leu Leu Lys Ala
            180                 185                 190

Arg Cys Lys Glu Gln Pro Glu Leu Glu Val Gln Tyr Gln Gly Arg Cys
        195                 200                 205
```

```
Lys Lys Thr Cys Glu Asp Ile Gln Cys Thr Gly Gly Lys Lys Cys Leu
    210                 215                 220

Trp Asp Phe Lys Val Gly Arg Gly Arg Cys Ser Leu Cys Asp Glu Leu
225                 230                 235                 240

Cys Pro Asp Ser Lys Ser Asp Glu Pro Val Cys Ala Ser Asp Asn Ala
            245                 250                 255

Thr Tyr Ala Ser Glu Cys Ala Met Lys Glu Ala Ala Cys Ser Ser Gly
        260                 265                 270

Val Leu Leu Glu Val Lys His Ser Gly Ser Cys Asn Ser Ile Ser Glu
    275                 280                 285

Asp Thr Glu Glu Glu Glu Asp Glu Asp Gln Asp Tyr Ser Phe Pro
290                 295                 300

Ile Ser Ser Ile Leu Glu Trp
305                 310

<210> SEQ ID NO 11
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
gcaagctttg tgagaacgtg gactgtg                                      27

<210> SEQ ID NO 12
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
gcctcgagat atcttcacaa gtcttttac atctgcc                            37

<210> SEQ ID NO 13
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
cggaattcat ggtccgcgcg aggcaccag                                    29

<210> SEQ ID NO 14
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
cgaagctttt tacatctgcc ttgg                                         24

<210> SEQ ID NO 15
<211> LENGTH: 765
<212> TYPE: DNA
<213> ORGANISM: Artificial Sequence
```

<220> FEATURE:
<223> OTHER INFORMATION: Description of Artificial Sequence: Synthetic
      polynucleotide
<220> FEATURE:
<221> NAME/KEY: CDS
<222> LOCATION: (1)..(765)

<400> SEQUENCE: 15

| | | | | | | | | | | | | | | | | |
|---|---|---|---|---|---|---|---|---|---|---|---|---|---|---|---|---|
| atg | gtc | cgc | gcg | agg | cac | cag | ccg | ggt | ggg | ctt | tgc | ctc | ctg | ctg | | 48 |
| Met | Val | Arg | Ala | Arg | His | Gln | Pro | Gly | Gly | Leu | Cys | Leu | Leu | Leu | | |
| 1 | | | | 5 | | | | | 10 | | | | | 15 | | |

| ctc | ctc | tgc | cag | ttc | atg | gag | gac | cgc | agt | gcc | cag | gct | ggg | aac | tgc | 96 |
|---|---|---|---|---|---|---|---|---|---|---|---|---|---|---|---|---|
| Leu | Leu | Cys | Gln | Phe | Met | Glu | Asp | Arg | Ser | Ala | Gln | Ala | Gly | Asn | Cys | |
| | | | | 20 | | | | | 25 | | | | | 30 | | |

| tgg | ctc | cgt | caa | gcg | aag | aac | ggc | cgc | tgc | cag | gtc | ctg | tac | aag | acc | 144 |
|---|---|---|---|---|---|---|---|---|---|---|---|---|---|---|---|---|
| Trp | Leu | Arg | Gln | Ala | Lys | Asn | Gly | Arg | Cys | Gln | Val | Leu | Tyr | Lys | Thr | |
| | | 35 | | | | | 40 | | | | | 45 | | | | |

| gaa | ctg | agc | aag | gag | gag | tgc | tgc | agc | acc | ggc | cgg | ctg | agc | acc | tcg | 192 |
|---|---|---|---|---|---|---|---|---|---|---|---|---|---|---|---|---|
| Glu | Leu | Ser | Lys | Glu | Glu | Cys | Cys | Ser | Thr | Gly | Arg | Leu | Ser | Thr | Ser | |
| | | 50 | | | | | 55 | | | | | 60 | | | | |

| tgg | acc | gag | gag | gac | gtg | aat | gac | aac | aca | ctc | ttc | aag | tgg | atg | att | 240 |
|---|---|---|---|---|---|---|---|---|---|---|---|---|---|---|---|---|
| Trp | Thr | Glu | Glu | Asp | Val | Asn | Asp | Asn | Thr | Leu | Phe | Lys | Trp | Met | Ile | |
| 65 | | | | | 70 | | | | | 75 | | | | | 80 | |

| ttc | aac | ggg | ggc | gcc | ccc | aac | tgc | atc | ccc | tgt | aaa | gaa | acg | tgt | gag | 288 |
|---|---|---|---|---|---|---|---|---|---|---|---|---|---|---|---|---|
| Phe | Asn | Gly | Gly | Ala | Pro | Asn | Cys | Ile | Pro | Cys | Lys | Glu | Thr | Cys | Glu | |
| | | | | 85 | | | | | 90 | | | | | 95 | | |

| aac | gtg | gac | tgt | gga | cct | ggg | aaa | aaa | tgc | cga | atg | aac | aag | aag | aac | 336 |
|---|---|---|---|---|---|---|---|---|---|---|---|---|---|---|---|---|
| Asn | Val | Asp | Cys | Gly | Pro | Gly | Lys | Lys | Cys | Arg | Met | Asn | Lys | Lys | Asn | |
| | | | | 100 | | | | | 105 | | | | | 110 | | |

| aaa | ccc | cgc | tgc | gtc | tgc | gcc | ccg | gat | tgt | tcc | aac | atc | acc | tgg | aag | 384 |
|---|---|---|---|---|---|---|---|---|---|---|---|---|---|---|---|---|
| Lys | Pro | Arg | Cys | Val | Cys | Ala | Pro | Asp | Cys | Ser | Asn | Ile | Thr | Trp | Lys | |
| | | 115 | | | | | 120 | | | | | 125 | | | | |

| ggt | cca | gtc | tgc | ggg | ctg | gat | ggg | aaa | acc | tac | cgc | aat | gaa | tgt | gca | 432 |
|---|---|---|---|---|---|---|---|---|---|---|---|---|---|---|---|---|
| Gly | Pro | Val | Cys | Gly | Leu | Asp | Gly | Lys | Thr | Tyr | Arg | Asn | Glu | Cys | Ala | |
| | | 130 | | | | | 135 | | | | | 140 | | | | |

| ctc | cta | aag | gca | aga | tgt | aaa | gag | cag | cca | gaa | ctg | gaa | gtc | cag | tac | 480 |
|---|---|---|---|---|---|---|---|---|---|---|---|---|---|---|---|---|
| Leu | Leu | Lys | Ala | Arg | Cys | Lys | Glu | Gln | Pro | Glu | Leu | Glu | Val | Gln | Tyr | |
| 145 | | | | | 150 | | | | | 155 | | | | | 160 | |

| caa | ggc | aga | tgt | aaa | aag | ctt | tgt | gag | aac | gtg | gac | tgt | gga | cct | ggg | 528 |
|---|---|---|---|---|---|---|---|---|---|---|---|---|---|---|---|---|
| Gln | Gly | Arg | Cys | Lys | Lys | Leu | Cys | Glu | Asn | Val | Asp | Cys | Gly | Pro | Gly | |
| | | | | 165 | | | | | 170 | | | | | 175 | | |

| aaa | aaa | tgc | cga | atg | aac | aag | aag | aac | aaa | ccc | cgc | tgc | gtc | tgc | gcc | 576 |
|---|---|---|---|---|---|---|---|---|---|---|---|---|---|---|---|---|
| Lys | Lys | Cys | Arg | Met | Asn | Lys | Lys | Asn | Lys | Pro | Arg | Cys | Val | Cys | Ala | |
| | | | | 180 | | | | | 185 | | | | | 190 | | |

| ccg | gat | tgt | tcc | aac | atc | acc | tgg | aag | ggt | cca | gtc | tgc | ggg | ctg | gat | 624 |
|---|---|---|---|---|---|---|---|---|---|---|---|---|---|---|---|---|
| Pro | Asp | Cys | Ser | Asn | Ile | Thr | Trp | Lys | Gly | Pro | Val | Cys | Gly | Leu | Asp | |
| | | 195 | | | | | 200 | | | | | 205 | | | | |

| ggg | aaa | acc | tac | cgc | aat | gaa | tgt | gca | ctc | cta | aag | gca | aga | tgt | aaa | 672 |
|---|---|---|---|---|---|---|---|---|---|---|---|---|---|---|---|---|
| Gly | Lys | Thr | Tyr | Arg | Asn | Glu | Cys | Ala | Leu | Leu | Lys | Ala | Arg | Cys | Lys | |
| | 210 | | | | | 215 | | | | | 220 | | | | | |

| gag | cag | cca | gaa | ctg | gaa | gtc | cag | tac | caa | ggc | aga | tgt | aaa | aag | act | 720 |
|---|---|---|---|---|---|---|---|---|---|---|---|---|---|---|---|---|
| Glu | Gln | Pro | Glu | Leu | Glu | Val | Gln | Tyr | Gln | Gly | Arg | Cys | Lys | Lys | Thr | |
| 225 | | | | | 230 | | | | | 235 | | | | | 240 | |

| tgt | gaa | gat | atc | tcg | agg | caa | tca | cta | gag | ggc | cct | att | cta | tag | | 765 |
|---|---|---|---|---|---|---|---|---|---|---|---|---|---|---|---|---|
| Cys | Glu | Asp | Ile | Ser | Arg | Gln | Ser | Leu | Glu | Gly | Pro | Ile | Leu | | | |
| | | | | 245 | | | | | 250 | | | | | | | |

<210> SEQ ID NO 16
<211> LENGTH: 254
<212> TYPE: PRT
<213> ORGANISM: Artificial Sequence
<220> FEATURE:

<223> OTHER INFORMATION: Description of Artificial Sequence: Synthetic
      polypeptide

<400> SEQUENCE: 16

Met Val Arg Ala Arg His Gln Pro Gly Gly Leu Cys Leu Leu Leu Leu
 1               5                  10                  15

Leu Leu Cys Gln Phe Met Glu Asp Arg Ser Ala Gln Ala Gly Asn Cys
            20                  25                  30

Trp Leu Arg Gln Ala Lys Asn Gly Arg Cys Gln Val Leu Tyr Lys Thr
        35                  40                  45

Glu Leu Ser Lys Glu Cys Cys Ser Thr Gly Arg Leu Ser Thr Ser
    50                  55                  60

Trp Thr Glu Glu Asp Val Asn Asp Asn Thr Leu Phe Lys Trp Met Ile
 65                  70                  75                  80

Phe Asn Gly Gly Ala Pro Asn Cys Ile Pro Cys Lys Glu Thr Cys Glu
                85                  90                  95

Asn Val Asp Cys Gly Pro Gly Lys Lys Cys Arg Met Asn Lys Lys Asn
            100                 105                 110

Lys Pro Arg Cys Val Cys Ala Pro Asp Cys Ser Asn Ile Thr Trp Lys
        115                 120                 125

Gly Pro Val Cys Gly Leu Asp Gly Lys Thr Tyr Arg Asn Glu Cys Ala
    130                 135                 140

Leu Leu Lys Ala Arg Cys Lys Glu Gln Pro Glu Leu Glu Val Gln Tyr
145                 150                 155                 160

Gln Gly Arg Cys Lys Lys Leu Cys Glu Asn Val Asp Cys Gly Pro Gly
                165                 170                 175

Lys Lys Cys Arg Met Asn Lys Lys Asn Lys Pro Arg Cys Val Cys Ala
            180                 185                 190

Pro Asp Cys Ser Asn Ile Thr Trp Lys Gly Pro Val Cys Gly Leu Asp
        195                 200                 205

Gly Lys Thr Tyr Arg Asn Glu Cys Ala Leu Leu Lys Ala Arg Cys Lys
    210                 215                 220

Glu Gln Pro Glu Leu Glu Val Gln Tyr Gln Gly Arg Cys Lys Lys Thr
225                 230                 235                 240

Cys Glu Asp Ile Ser Arg Gln Ser Leu Glu Gly Pro Ile Leu
                245                 250

<210> SEQ ID NO 17
<211> LENGTH: 567
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(567)

<400> SEQUENCE: 17 atg gtc cgc gcg agg cac cag ccg ggt ggg ctt tgc ctc ctg ctg ctg      48
Met Val Arg Ala Arg His Gln Pro Gly Gly Leu Cys Leu Leu Leu Leu
 1               5                  10                  15 ctg ctc tgc cag ttc atg gag gac cgc agt gcc cag gct ggg aac tgc      96
Leu Leu Cys Gln Phe Met Glu Asp Arg Ser Ala Gln Ala Gly Asn Cys
            20                  25                  30 tgg ctc cgt caa gcg aag aac ggc cgc tgc cag gtc ctg tac aag acc     144
Trp Leu Arg Gln Ala Lys Asn Gly Arg Cys Gln Val Leu Tyr Lys Thr
        35                  40                  45

```
gaa ctg agc aag gag gag tgc tgc agc acc ggc cgg ctg agc acc tcg      192
Glu Leu Ser Lys Glu Glu Cys Cys Ser Thr Gly Arg Leu Ser Thr Ser
    50                  55                  60 tgg acc gag gag gac gtg aat gac aac aca ctc ttc aag tgg atg att      240
Trp Thr Glu Glu Asp Val Asn Asp Asn Thr Leu Phe Lys Trp Met Ile
65                  70                  75                  80 ttc aac ggg ggc gcc ccc aac tgc atc ccc tgt aaa gaa acg tgt gag      288
Phe Asn Gly Gly Ala Pro Asn Cys Ile Pro Cys Lys Glu Thr Cys Glu
                85                  90                  95 aac gtg gac tgt gga cct ggg aaa aaa tgc cga atg aac aag aag aac      336
Asn Val Asp Cys Gly Pro Gly Lys Lys Cys Arg Met Asn Lys Lys Asn
            100                 105                 110 aaa ccc cgc tgc gtc tgc gcc ccg gat tgt tcc aac atc acc tgg aag      384
Lys Pro Arg Cys Val Cys Ala Pro Asp Cys Ser Asn Ile Thr Trp Lys
        115                 120                 125 ggt cca gtc tgc ggg ctg gat ggg aaa acc tac cgc aat gaa tgt gca      432
Gly Pro Val Cys Gly Leu Asp Gly Lys Thr Tyr Arg Asn Glu Cys Ala
130                 135                 140 ctc cta aag gca aga tgt aaa gag cag cca gaa ctg gaa gtc cag tac      480
Leu Leu Lys Ala Arg Cys Lys Glu Gln Pro Glu Leu Glu Val Gln Tyr
145                 150                 155                 160 caa ggc aga tgt aaa aag ctt atc gat acc gtc gac ctc gag cat gca      528
Gln Gly Arg Cys Lys Lys Leu Ile Asp Thr Val Asp Leu Glu His Ala
                165                 170                 175 tct aga ggg ccc tat tct ata gtg tca cct aaa tgc tag                  567
Ser Arg Gly Pro Tyr Ser Ile Val Ser Pro Lys Cys
            180                 185

<210> SEQ ID NO 18
<211> LENGTH: 188
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Met Val Arg Ala Arg His Gln Pro Gly Gly Leu Cys Leu Leu Leu Leu
1               5                   10                  15

Leu Leu Cys Gln Phe Met Glu Asp Arg Ser Ala Gln Ala Gly Asn Cys
            20                  25                  30

Trp Leu Arg Gln Ala Lys Asn Gly Arg Cys Gln Val Leu Tyr Lys Thr
        35                  40                  45

Glu Leu Ser Lys Glu Glu Cys Cys Ser Thr Gly Arg Leu Ser Thr Ser
    50                  55                  60

Trp Thr Glu Glu Asp Val Asn Asp Asn Thr Leu Phe Lys Trp Met Ile
65                  70                  75                  80

Phe Asn Gly Gly Ala Pro Asn Cys Ile Pro Cys Lys Glu Thr Cys Glu
                85                  90                  95

Asn Val Asp Cys Gly Pro Gly Lys Lys Cys Arg Met Asn Lys Lys Asn
            100                 105                 110

Lys Pro Arg Cys Val Cys Ala Pro Asp Cys Ser Asn Ile Thr Trp Lys
        115                 120                 125

Gly Pro Val Cys Gly Leu Asp Gly Lys Thr Tyr Arg Asn Glu Cys Ala
130                 135                 140

Leu Leu Lys Ala Arg Cys Lys Glu Gln Pro Glu Leu Glu Val Gln Tyr
145                 150                 155                 160

Gln Gly Arg Cys Lys Lys Leu Ile Asp Thr Val Asp Leu Glu His Ala
                165                 170                 175
```

```
Ser Arg Gly Pro Tyr Ser Ile Val Ser Pro Lys Cys
            180                 185
```

<210> SEQ ID NO 19
<211> LENGTH: 1023
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(1023)

<400> SEQUENCE: 19

```
atg gtc cgc gcg agg cac cag ccg ggt ggg ctt tgc ctc ctg ctg      48
Met Val Arg Ala Arg His Gln Pro Gly Gly Leu Cys Leu Leu Leu
 1               5                  10                  15 ctc ctc tgc cag ttc atg gag gac cgc agt gcc cag gct ggg aac tgc  96
Leu Leu Cys Gln Phe Met Glu Asp Arg Ser Ala Gln Ala Gly Asn Cys
                20                  25                  30 tgg ctc cgt caa gcg aag aac ggc cgc tgc cag gtc ctg tac aag acc  144
Trp Leu Arg Gln Ala Lys Asn Gly Arg Cys Gln Val Leu Tyr Lys Thr
            35                  40                  45 gaa ctg agc aag gag gag tgc tgc agc acc ggc cgg ctg agc acc tcg  192
Glu Leu Ser Lys Glu Glu Cys Cys Ser Thr Gly Arg Leu Ser Thr Ser
        50                  55                  60 tgg acc gag gag gac gtg aat gac aac aca ctc ttc aag tgg atg att  240
Trp Thr Glu Glu Asp Val Asn Asp Asn Thr Leu Phe Lys Trp Met Ile
 65                  70                  75                  80 ttc aac ggg ggc gcc ccc aac tgc atc ccc tgt aaa gaa acg tgt gag  288
Phe Asn Gly Gly Ala Pro Asn Cys Ile Pro Cys Lys Glu Thr Cys Glu
                85                  90                  95 aac gtg gac tgt gga cct ggg aaa aaa tgc cga atg aac aag aag aac  336
Asn Val Asp Cys Gly Pro Gly Lys Lys Cys Arg Met Asn Lys Lys Asn
                100                 105                 110 aaa ccc cgc tgc gtc tgc gcc ccg gat tgt tcc aac atc acc tgg aag  384
Lys Pro Arg Cys Val Cys Ala Pro Asp Cys Ser Asn Ile Thr Trp Lys
            115                 120                 125 ggt cca gtc tgc ggg ctg gat ggg aaa acc tac cgc aat gaa tgt gca  432
Gly Pro Val Cys Gly Leu Asp Gly Lys Thr Tyr Arg Asn Glu Cys Ala
        130                 135                 140 ctc cta aag gca aga tgt aaa gag cag cca gaa ctg gaa gtc cag tac  480
Leu Leu Lys Ala Arg Cys Lys Glu Gln Pro Glu Leu Glu Val Gln Tyr
145                 150                 155                 160 caa ggc aga tgt aaa aag ctt tgt gag aac gtg gac tgt gga cct ggg  528
Gln Gly Arg Cys Lys Lys Leu Cys Glu Asn Val Asp Cys Gly Pro Gly
                165                 170                 175 aaa aaa tgc cga atg aac aag aag aac aaa ccc cgc tgc gtc tgc gcc  576
Lys Lys Cys Arg Met Asn Lys Lys Asn Lys Pro Arg Cys Val Cys Ala
                180                 185                 190 ccg gat tgt tcc aac atc acc tgg aag ggt cca gtc tgc ggg ctg gat  624
Pro Asp Cys Ser Asn Ile Thr Trp Lys Gly Pro Val Cys Gly Leu Asp
            195                 200                 205 ggg aaa acc tac cgc aat gaa tgt gca ctc cta aag gca aga tgt aaa  672
Gly Lys Thr Tyr Arg Asn Glu Cys Ala Leu Leu Lys Ala Arg Cys Lys
        210                 215                 220 gag cag cca gaa ctg gaa gtc cag tac caa ggc aga tgt aaa aag act  720
Glu Gln Pro Glu Leu Glu Val Gln Tyr Gln Gly Arg Cys Lys Lys Thr
225                 230                 235                 240 tgt gaa gat atc cag tgc act ggt ggg aaa aaa tgt tta tgg gat ttc  768
```

```
Cys Glu Asp Ile Gln Cys Thr Gly Gly Lys Lys Cys Leu Trp Asp Phe
            245                 250                 255 aag gtt ggg aga ggc cgg tgt tcc ctc tgt gat gag ctg tgc cct gac    816
Lys Val Gly Arg Gly Arg Cys Ser Leu Cys Asp Glu Leu Cys Pro Asp
        260                 265                 270 agt aag tcg gat gag cct gtc tgt gcc agt gac aat gcc act tat gcc    864
Ser Lys Ser Asp Glu Pro Val Cys Ala Ser Asp Asn Ala Thr Tyr Ala
    275                 280                 285 agc gag tgt gcc atg aag gaa gct gcc tgc tcc tca ggt gtg cta ctg    912
Ser Glu Cys Ala Met Lys Glu Ala Ala Cys Ser Ser Gly Val Leu Leu
290                 295                 300 gaa gta aag cac tcc gga tct tgc aac tcc att tcg gaa gac acc gag    960
Glu Val Lys His Ser Gly Ser Cys Asn Ser Ile Ser Glu Asp Thr Glu
305                 310                 315                 320 gaa gag gag gaa gat gaa gac cag gac tac agc ttt cct ata tct tct   1008
Glu Glu Glu Glu Asp Glu Asp Gln Asp Tyr Ser Phe Pro Ile Ser Ser
                325                 330                 335 att cta gag tgg taa                                               1023
Ile Leu Glu Trp
            340

<210> SEQ ID NO 20
<211> LENGTH: 340
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Met Val Arg Ala Arg His Gln Pro Gly Gly Leu Cys Leu Leu Leu Leu
 1               5                  10                  15

Leu Leu Cys Gln Phe Met Glu Asp Arg Ser Ala Gln Ala Gly Asn Cys
            20                  25                  30

Trp Leu Arg Gln Ala Lys Asn Gly Arg Cys Gln Val Leu Tyr Lys Thr
        35                  40                  45

Glu Leu Ser Lys Glu Glu Cys Cys Ser Thr Gly Arg Leu Ser Thr Ser
    50                  55                  60

Trp Thr Glu Glu Asp Val Asn Asp Asn Thr Leu Phe Lys Trp Met Ile
65                  70                  75                  80

Phe Asn Gly Gly Ala Pro Asn Cys Ile Pro Cys Lys Glu Thr Cys Glu
                85                  90                  95

Asn Val Asp Cys Gly Pro Gly Lys Lys Cys Arg Met Asn Lys Lys Asn
            100                 105                 110

Lys Pro Arg Cys Val Cys Ala Pro Asp Cys Ser Asn Ile Thr Trp Lys
        115                 120                 125

Gly Pro Val Cys Gly Leu Asp Gly Lys Thr Tyr Arg Asn Glu Cys Ala
    130                 135                 140

Leu Leu Lys Ala Arg Cys Lys Glu Gln Pro Glu Leu Glu Val Gln Tyr
145                 150                 155                 160

Gln Gly Arg Cys Lys Lys Leu Cys Glu Asn Val Asp Cys Gly Pro Gly
                165                 170                 175

Lys Lys Cys Arg Met Asn Lys Lys Asn Lys Pro Arg Cys Val Cys Ala
            180                 185                 190

Pro Asp Cys Ser Asn Ile Thr Trp Lys Gly Pro Val Cys Gly Leu Asp
        195                 200                 205

Gly Lys Thr Tyr Arg Asn Glu Cys Ala Leu Leu Lys Ala Arg Cys Lys
    210                 215                 220
```

-continued

```
Glu Gln Pro Glu Leu Glu Val Gln Tyr Gln Gly Arg Cys Lys Lys Thr
225                 230                 235                 240

Cys Glu Asp Ile Gln Cys Thr Gly Gly Lys Lys Cys Leu Trp Asp Phe
            245                 250                 255

Lys Val Gly Arg Gly Arg Cys Ser Leu Cys Asp Glu Leu Cys Pro Asp
        260                 265                 270

Ser Lys Ser Asp Glu Pro Val Cys Ala Ser Asp Asn Ala Thr Tyr Ala
    275                 280                 285

Ser Glu Cys Ala Met Lys Glu Ala Ala Cys Ser Ser Gly Val Leu Leu
    290                 295                 300

Glu Val Lys His Ser Gly Ser Cys Asn Ser Ile Ser Glu Asp Thr Glu
305                 310                 315                 320

Glu Glu Glu Glu Asp Glu Asp Gln Asp Tyr Ser Phe Pro Ile Ser Ser
                325                 330                 335

Ile Leu Glu Trp
            340

<210> SEQ ID NO 21
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
ccggaattct gtcaaaagtc ttgc                                          24

<210> SEQ ID NO 22
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
ccggaattcc tcgagtcaca cgaagttctc ttcctcctc                          39

<210> SEQ ID NO 23
<211> LENGTH: 1017
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(1017)

<400> SEQUENCE: 23 atg gtc cgc gcg agg cac cag ccg ggt ggg ctt tgc ctc ctg ctg ctg     48
Met Val Arg Ala Arg His Gln Pro Gly Gly Leu Cys Leu Leu Leu Leu
 1               5                  10                  15 ctg ctc tgc cag ttc atg gag gac cgc agt gcc cag gct ggg aac tgc     96
Leu Leu Cys Gln Phe Met Glu Asp Arg Ser Ala Gln Ala Gly Asn Cys
             20                  25                  30 tgg ctc cgt caa gcg aag aac ggc cgc tgc cag gtc ctg tac aag acc    144
Trp Leu Arg Gln Ala Lys Asn Gly Arg Cys Gln Val Leu Tyr Lys Thr
         35                  40                  45 gaa ctg agc aag gag gag tgc tgc agc acc ggc cgg ctg agc acc tcg    192
Glu Leu Ser Lys Glu Glu Cys Cys Ser Thr Gly Arg Leu Ser Thr Ser
```

```
                 50                  55                  60
tgg acc gag gag gac gtg aat gac aac aca ctc ttc aag tgg atg att    240
Trp Thr Glu Glu Asp Val Asn Asp Asn Thr Leu Phe Lys Trp Met Ile
 65                  70                  75                  80 ttc aac ggg ggc gcc ccc aac tgc atc ccc tgt aaa gaa acg tgt gag    288
Phe Asn Gly Gly Ala Pro Asn Cys Ile Pro Cys Lys Glu Thr Cys Glu
                 85                  90                  95 aac gtg gac tgt gga cct ggg aaa aaa tgc cga atg aac aag aag aac    336
Asn Val Asp Cys Gly Pro Gly Lys Lys Cys Arg Met Asn Lys Lys Asn
            100                 105                 110 aaa ccc cgc tgc gtc tgc gcc ccg gat tgt tcc aac atc acc tgg aag    384
Lys Pro Arg Cys Val Cys Ala Pro Asp Cys Ser Asn Ile Thr Trp Lys
        115                 120                 125 ggt cca gtc tgc ggg ctg gat ggg aaa acc tac cgc aat gaa tgt gca    432
Gly Pro Val Cys Gly Leu Asp Gly Lys Thr Tyr Arg Asn Glu Cys Ala
    130                 135                 140 ctc cta aag gca aga tgt aaa gag cag cca gaa ctg gaa gtc cag tac    480
Leu Leu Lys Ala Arg Cys Lys Glu Gln Pro Glu Leu Glu Val Gln Tyr
145                 150                 155                 160 caa ggc aga tgt aaa aag ctt tgt gag aac gtg gac tgt gga cct ggg    528
Gln Gly Arg Cys Lys Lys Leu Cys Glu Asn Val Asp Cys Gly Pro Gly
                165                 170                 175 aaa aaa tgc cga atg aac aag aag aac aaa ccc cgc tgc gtc tgc gcc    576
Lys Lys Cys Arg Met Asn Lys Lys Asn Lys Pro Arg Cys Val Cys Ala
            180                 185                 190 ccg gat tgt tcc aac atc acc tgg aag ggt cca gtc tgc ggg ctg gat    624
Pro Asp Cys Ser Asn Ile Thr Trp Lys Gly Pro Val Cys Gly Leu Asp
        195                 200                 205 ggg aaa acc tac cgc aat gaa tgt gca ctc cta aag gca aga tgt aaa    672
Gly Lys Thr Tyr Arg Asn Glu Cys Ala Leu Leu Lys Ala Arg Cys Lys
    210                 215                 220 gag cag cca gaa ctg gaa gtc cag tac caa ggc aga tgt aaa aag act    720
Glu Gln Pro Glu Leu Glu Val Gln Tyr Gln Gly Arg Cys Lys Lys Thr
225                 230                 235                 240 tgt gaa gat atc gaa ttc tgt caa aag tct tgc gct cag gta gtg tgc    768
Cys Glu Asp Ile Glu Phe Cys Gln Lys Ser Cys Ala Gln Val Val Cys
                245                 250                 255 ccg cgt ccc cag tcg tgc ctt gtg gat cag acc ggc agc gca cac tgc    816
Pro Arg Pro Gln Ser Cys Leu Val Asp Gln Thr Gly Ser Ala His Cys
            260                 265                 270 gtg gtg tgt cgc gct gcg ccc tgc cca gta cct tcc aac ccc ggc caa    864
Val Val Cys Arg Ala Ala Pro Cys Pro Val Pro Ser Asn Pro Gly Gln
        275                 280                 285 gaa ctc tgt ggc aac aac aac gtt acc tac atc tcg tcg tgt cac ctg    912
Glu Leu Cys Gly Asn Asn Asn Val Thr Tyr Ile Ser Ser Cys His Leu
    290                 295                 300 cgc cag gcc act tgc ttc ctg ggc cgc tcc att ggg gtt cgg cac cca    960
Arg Gln Ala Thr Cys Phe Leu Gly Arg Ser Ile Gly Val Arg His Pro
305                 310                 315                 320 ggc atc tgc aca ggt ggc ccc aaa gta cca gca gag gag gaa gag aac   1008
Gly Ile Cys Thr Gly Gly Pro Lys Val Pro Ala Glu Glu Glu Glu Asn
                325                 330                 335 ttc gtg tga                                                       1017
Phe Val

<210> SEQ ID NO 24
<211> LENGTH: 338
<212> TYPE: PRT
<213> ORGANISM: Artificial Sequence
<220> FEATURE:
```

<223> OTHER INFORMATION: Description of Artificial Sequence: Synthetic
      polypeptide

<400> SEQUENCE: 24

```
Met Val Arg Ala Arg His Gln Pro Gly Gly Leu Cys Leu Leu Leu Leu
  1               5                  10                  15

Leu Leu Cys Gln Phe Met Glu Asp Arg Ser Ala Gln Ala Gly Asn Cys
             20                  25                  30

Trp Leu Arg Gln Ala Lys Asn Gly Arg Cys Gln Val Leu Tyr Lys Thr
         35                  40                  45

Glu Leu Ser Lys Glu Glu Cys Cys Ser Thr Gly Arg Leu Ser Thr Ser
 50                  55                  60

Trp Thr Glu Glu Asp Val Asn Asp Asn Thr Leu Phe Lys Trp Met Ile
 65                  70                  75                  80

Phe Asn Gly Gly Ala Pro Asn Cys Ile Pro Cys Lys Glu Thr Cys Glu
                 85                  90                  95

Asn Val Asp Cys Gly Pro Gly Lys Lys Cys Arg Met Asn Lys Lys Asn
            100                 105                 110

Lys Pro Arg Cys Val Cys Ala Pro Asp Cys Ser Asn Ile Thr Trp Lys
        115                 120                 125

Gly Pro Val Cys Gly Leu Asp Gly Lys Thr Tyr Arg Asn Glu Cys Ala
    130                 135                 140

Leu Leu Lys Ala Arg Cys Lys Glu Gln Pro Glu Leu Glu Val Gln Tyr
145                 150                 155                 160

Gln Gly Arg Cys Lys Lys Leu Cys Glu Asn Val Asp Cys Gly Pro Gly
                165                 170                 175

Lys Lys Cys Arg Met Asn Lys Lys Asn Lys Pro Arg Cys Val Cys Ala
            180                 185                 190

Pro Asp Cys Ser Asn Ile Thr Trp Lys Gly Pro Val Cys Gly Leu Asp
        195                 200                 205

Gly Lys Thr Tyr Arg Asn Glu Cys Ala Leu Leu Lys Ala Arg Cys Lys
    210                 215                 220

Glu Gln Pro Glu Leu Glu Val Gln Tyr Gln Gly Arg Cys Lys Lys Thr
225                 230                 235                 240

Cys Glu Asp Ile Glu Phe Cys Gln Lys Ser Cys Ala Gln Val Val Cys
                245                 250                 255

Pro Arg Pro Gln Ser Cys Leu Val Asp Gln Thr Gly Ser Ala His Cys
            260                 265                 270

Val Val Cys Arg Ala Ala Pro Cys Pro Val Pro Ser Asn Pro Gly Gln
        275                 280                 285

Glu Leu Cys Gly Asn Asn Asn Val Thr Tyr Ile Ser Ser Cys His Leu
    290                 295                 300

Arg Gln Ala Thr Cys Phe Leu Gly Arg Ser Ile Gly Val Arg His Pro
305                 310                 315                 320

Gly Ile Cys Thr Gly Gly Pro Lys Val Pro Ala Glu Glu Glu Glu Asn
                325                 330                 335

Phe Val
```

<210> SEQ ID NO 25
<211> LENGTH: 309
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

```
Gly Asn Cys Trp Leu Arg Gln Ala Lys Asn Gly Arg Cys Gln Val Leu
  1               5                  10                  15
Tyr Lys Thr Glu Leu Ser Lys Glu Glu Cys Cys Ser Thr Gly Arg Leu
             20                  25                  30
Ser Thr Ser Trp Thr Glu Glu Asp Val Asn Asp Asn Thr Leu Phe Lys
         35                  40                  45
Trp Met Ile Phe Asn Gly Gly Ala Pro Asn Cys Ile Pro Cys Lys Glu
     50                  55                  60
Thr Cys Glu Asn Val Asp Cys Gly Pro Gly Lys Lys Cys Arg Met Asn
 65                  70                  75                  80
Lys Lys Asn Lys Pro Arg Cys Val Cys Ala Pro Asp Cys Ser Asn Ile
                 85                  90                  95
Thr Trp Lys Gly Pro Val Cys Gly Leu Asp Gly Lys Thr Tyr Arg Asn
            100                 105                 110
Glu Cys Ala Leu Leu Lys Ala Arg Cys Lys Gln Pro Glu Leu Glu
        115                 120                 125
Val Gln Tyr Gln Gly Arg Cys Lys Lys Leu Cys Glu Asn Val Asp Cys
    130                 135                 140
Gly Pro Gly Lys Lys Cys Arg Met Asn Lys Lys Asn Lys Pro Arg Cys
145                 150                 155                 160
Val Cys Ala Pro Asp Cys Ser Asn Ile Thr Trp Lys Gly Pro Val Cys
                165                 170                 175
Gly Leu Asp Gly Lys Thr Tyr Arg Asn Glu Cys Ala Leu Leu Lys Ala
            180                 185                 190
Arg Cys Lys Glu Gln Pro Glu Leu Glu Val Gln Tyr Gln Gly Arg Cys
        195                 200                 205
Lys Lys Thr Cys Glu Asp Ile Glu Phe Cys Gln Lys Ser Cys Ala Gln
    210                 215                 220
Val Val Cys Pro Arg Pro Gln Ser Cys Leu Val Asp Gln Thr Gly Ser
225                 230                 235                 240
Ala His Cys Val Val Cys Arg Ala Ala Pro Cys Pro Val Pro Ser Asn
                245                 250                 255
Pro Gly Gln Glu Leu Cys Gly Asn Asn Asn Val Thr Tyr Ile Ser Ser
            260                 265                 270
Cys His Leu Arg Gln Ala Thr Cys Phe Leu Gly Arg Ser Ile Gly Val
        275                 280                 285
Arg His Pro Gly Ile Cys Thr Gly Gly Pro Lys Val Pro Ala Glu Glu
    290                 295                 300
Glu Glu Asn Phe Val
305
```

<210> SEQ ID NO 26
<211> LENGTH: 12
<212> TYPE: PRT
<213> ORGANISM: Homo sapiens

<400> SEQUENCE: 26

```
Glu Gln Pro Glu Leu Glu Val Gln Tyr Gln Gly Arg
  1               5                  10
```

<210> SEQ ID NO 27
<211> LENGTH: 30
<212> TYPE: DNA
<213> ORGANISM: Artificial Sequence
<220> FEATURE:

<223> OTHER INFORMATION: Description of Artificial Sequence: Synthetic
       primer

<400> SEQUENCE: 27
aagggtacca tggtccgcgc gaggcaccag                                          30

<210> SEQ ID NO 28
<211> LENGTH: 26
<212> TYPE: DNA
<213> ORGANISM: Artificial Sequence
<220> FEATURE:
<223> OTHER INFORMATION: Description of Artificial Sequence: Synthetic
       primer

<400> SEQUENCE: 28
tcgggatcca cgcagcgggg tttgtt                                              26

<210> SEQ ID NO 29
<211> LENGTH: 73
<212> TYPE: PRT
<213> ORGANISM: Mus musculus

<400> SEQUENCE: 29

Cys Ala Gln Val Val Cys Pro Arg Pro Gln Ser Cys Leu Val Asp Gln
 1               5                  10                  15

Thr Gly Ser Ala His Cys Val Val Cys Arg Ala Ala Pro Cys Pro Val
            20                  25                  30

Pro Ser Asn Pro Gly Gln Glu Leu Cys Gly Asn Asn Asn Val Thr Tyr
        35                  40                  45

Ile Ser Ser Cys His Leu Arg Gln Ala Thr Cys Phe Leu Gly Arg Ser
    50                  55                  60

Ile Gly Val Arg His Pro Gly Ile Cys
 65                  70

<210> SEQ ID NO 30
<211> LENGTH: 91
<212> TYPE: PRT
<213> ORGANISM: Artificial Sequence
<220> FEATURE:
<223> OTHER INFORMATION: Description of Artificial Sequence: Synthetic
       polypeptide
<220> FEATURE:
<221> NAME/KEY: MOD_RES
<222> LOCATION: (2)..(7)
<223> OTHER INFORMATION: region may encompass between 2 and 6 variable
       amino acids other than Cys
<220> FEATURE:
<221> NAME/KEY: MOD_RES
<222> LOCATION: (9)..(15)
<223> OTHER INFORMATION: region may encompass between 3 and 7 variable
       amino acids other than Cys
<220> FEATURE:
<221> NAME/KEY: MOD_RES
<222> LOCATION: (17)..(27)
<223> OTHER INFORMATION: region may encompass between 7 and 11 variable
       amino acids other than Cys
<220> FEATURE:
<221> NAME/KEY: MOD_RES
<222> LOCATION: (29)..(32)
<223> OTHER INFORMATION: region may encompass between 0 and 4 variable
       amino acids other than Cys
<220> FEATURE:
<221> NAME/KEY: MOD_RES
<222> LOCATION: (34)..(39)
<223> OTHER INFORMATION: region may encompass between 1 and 6 variable
       amino acids other than Cys
<220> FEATURE:
<221> NAME/KEY: MOD_RES
<222> LOCATION: (41)..(52)

```
<223> OTHER INFORMATION: region may encompass between 8 and 12 variable
      amino acids other than Cys
<220> FEATURE:
<221> NAME/KEY: MOD_RES
<222> LOCATION: (54)..(65)
<223> OTHER INFORMATION: region may encompass between 8 and 12 variable
      amino acids other than Cys
<220> FEATURE:
<221> NAME/KEY: MOD_RES
<222> LOCATION: (67)..(74)
<223> OTHER INFORMATION: region may encompass between 4 and 8 variable
      amino acids other than Cys
<220> FEATURE:
<221> NAME/KEY: MOD_RES
<222> LOCATION: (76)..(90)
<223> OTHER INFORMATION: region may encompass between 11 and 15 variable
      amino acids other than Cys

<400> SEQUENCE: 30

Cys Xaa Xaa Xaa Xaa Xaa Xaa Cys Xaa Xaa Xaa Xaa Xaa Xaa Xaa Cys
  1               5                  10                  15

Xaa Xaa Xaa Xaa Xaa Xaa Xaa Xaa Xaa Xaa Cys Xaa Xaa Xaa Xaa
             20                  25                  30

Cys Xaa Xaa Xaa Xaa Xaa Xaa Cys Xaa Xaa Xaa Xaa Xaa Xaa Xaa
         35                  40                  45

Xaa Xaa Xaa Xaa Cys Xaa Xaa Xaa Xaa Xaa Xaa Xaa Xaa Xaa Xaa
     50                  55                  60

Xaa Cys Xaa Xaa Xaa Xaa Xaa Xaa Xaa Xaa Cys Xaa Xaa Xaa Xaa Xaa
 65                  70                  75                  80

Xaa Xaa Xaa Xaa Xaa Xaa Xaa Xaa Xaa Xaa Cys
             85                  90

<210> SEQ ID NO 31
<211> LENGTH: 73
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(5)
<223> OTHER INFORMATION: variable amino acid other than Cys
<220> FEATURE:
<221> NAME/KEY: MOD_RES
<222> LOCATION: (7)..(11)
<223> OTHER INFORMATION: variable amino acid other than Cys
<220> FEATURE:
<221> NAME/KEY: MOD_RES
<222> LOCATION: (13)..(22)
<223> OTHER INFORMATION: region may encompass between 9 and 10 variable
      amino acids other than Cys
<220> FEATURE:
<221> NAME/KEY: MOD_RES
<222> LOCATION: (24)..(25)
<223> OTHER INFORMATION: region may encompass between 1 and 2 variable
      amino acids other than Cys
<220> FEATURE:
<221> NAME/KEY: MOD_RES
<222> LOCATION: (27)..(29)
<223> OTHER INFORMATION: variable amino acid other than Cys
<220> FEATURE:
<221> NAME/KEY: MOD_RES
<222> LOCATION: (31)..(40)
<223> OTHER INFORMATION: region may encompass between 9 and 10 variable
      amino acids other than Cys
<220> FEATURE:
<221> NAME/KEY: MOD_RES
<222> LOCATION: (42)..(51)
<223> OTHER INFORMATION: variable amino acid other than Cys
<220> FEATURE:
<221> NAME/KEY: MOD_RES
```

```
<222> LOCATION: (53)..(58)
<223> OTHER INFORMATION: variable amino acid other than Cys
<220> FEATURE:
<221> NAME/KEY: MOD_RES
<222> LOCATION: (60)..(72)
<223> OTHER INFORMATION: variable amino acid other than Cys

<400> SEQUENCE: 31

Cys Xaa Xaa Xaa Cys Xaa Xaa Xaa Xaa Cys Xaa Xaa Xaa Xaa
 1               5                  10                  15

Xaa Xaa Xaa Xaa Xaa Xaa Cys Xaa Xaa Cys Xaa Xaa Xaa Cys Xaa Xaa
            20                  25                  30

Xaa Xaa Xaa Xaa Xaa Xaa Xaa Cys Xaa Xaa Xaa Xaa Xaa Xaa
        35                  40                  45

Xaa Xaa Xaa Cys Xaa Xaa Xaa Xaa Xaa Cys Xaa Xaa Xaa Xaa
    50                  55                  60

Xaa Xaa Xaa Xaa Xaa Xaa Xaa Xaa Cys
 65                  70

<210> SEQ ID NO 32
<211> LENGTH: 315
<212> TYPE: PRT
<213> ORGANISM: Homo sapiens

<400> SEQUENCE: 32

Gly Asn Cys Trp Leu Arg Gln Ala Lys Asn Gly Arg Cys Gln Val Leu
 1               5                  10                  15

Tyr Lys Thr Glu Leu Ser Lys Glu Glu Cys Cys Ser Thr Gly Arg Leu
            20                  25                  30

Ser Thr Ser Trp Thr Glu Glu Asp Val Asn Asp Asn Thr Leu Phe Lys
        35                  40                  45

Trp Met Ile Phe Asn Gly Gly Ala Pro Asn Cys Ile Pro Cys Lys Glu
    50                  55                  60

Thr Cys Glu Asn Val Asp Cys Gly Pro Gly Lys Lys Cys Arg Met Asn
 65                  70                  75                  80

Lys Lys Asn Lys Pro Arg Cys Val Cys Ala Pro Asp Cys Ser Asn Ile
                85                  90                  95

Thr Trp Lys Gly Pro Val Cys Gly Leu Asp Gly Lys Thr Tyr Arg Asn
            100                 105                 110

Glu Cys Ala Leu Leu Lys Ala Arg Cys Lys Glu Gln Pro Glu Leu Glu
        115                 120                 125

Val Gln Tyr Gln Gly Arg Cys Lys Lys Thr Cys Arg Asp Val Phe Cys
    130                 135                 140

Pro Gly Ser Ser Thr Cys Val Val Asp Gln Thr Asn Asn Ala Tyr Cys
145                 150                 155                 160

Val Thr Cys Asn Arg Ile Cys Pro Glu Pro Ala Ser Ser Glu Gln Tyr
                165                 170                 175

Leu Cys Gly Asn Asp Gly Val Thr Tyr Ser Ser Ala Cys His Leu Arg
            180                 185                 190

Lys Ala Thr Cys Leu Leu Gly Arg Ser Ile Gly Leu Ala Tyr Glu Gly
        195                 200                 205

Lys Cys Ile Lys Ala Lys Ser Cys Glu Asp Ile Gln Cys Thr Gly Gly
    210                 215                 220

Lys Lys Cys Leu Trp Asp Phe Lys Val Gly Arg Gly Arg Cys Ser Leu
225                 230                 235                 240

Cys Asp Glu Leu Cys Pro Asp Ser Lys Ser Asp Glu Pro Val Cys Ala
                245                 250                 255
```

Ser Asp Asn Ala Thr Tyr Ala Ser Glu Cys Ala Met Lys Glu Ala Ala
            260                 265                 270

Cys Ser Ser Gly Val Leu Leu Glu Val Lys His Ser Gly Ser Cys Asn
        275                 280                 285

Ser Ile Ser Glu Asp Thr Glu Glu Glu Glu Asp Glu Asp Gln Asp
        290                 295                 300

Tyr Ser Phe Pro Ile Ser Ser Ile Leu Glu Trp
305                 310                 315

<210> SEQ ID NO 33
<211> LENGTH: 314
<212> TYPE: PRT
<213> ORGANISM: Mus musculus

<400> SEQUENCE: 33

Gly Asn Cys Trp Leu Arg Gln Ala Lys Asn Gly Arg Cys Gln Val Leu
1               5                   10                  15

Tyr Lys Thr Glu Leu Ser Lys Glu Glu Cys Cys Ser Thr Gly Arg Leu
            20                  25                  30

Ser Thr Ser Trp Thr Glu Glu Asp Val Asn Asp Asn Thr Leu Phe Lys
        35                  40                  45

Trp Met Ile Phe Asn Gly Gly Ala Pro Asn Cys Ile Pro Cys Lys Glu
    50                  55                  60

Thr Cys Glu Asn Val Asp Cys Gly Pro Gly Lys Lys Cys Arg Met Asn
65                  70                  75                  80

Lys Lys Asn Lys Pro Arg Cys Val Cys Ala Pro Asp Cys Ser Asn Ile
                85                  90                  95

Thr Trp Lys Gly Pro Val Cys Gly Leu Asp Gly Lys Thr Tyr Arg Asn
            100                 105                 110

Glu Cys Ala Leu Leu Lys Ala Arg Cys Lys Glu Gln Pro Glu Leu Glu
        115                 120                 125

Val Gln Tyr Gln Gly Lys Cys Lys Lys Thr Cys Arg Asp Val Phe Cys
    130                 135                 140

Pro Gly Ser Ser Thr Cys Val Val Asp Gln Thr Asn Asn Ala Tyr Cys
145                 150                 155                 160

Val Thr Cys Asn Arg Ile Cys Pro Glu Pro Ser Ser Ser Glu Gln Tyr
                165                 170                 175

Leu Cys Gly Asn Asp Gly Val Thr Tyr Ser Ser Ala Cys His Leu Arg
            180                 185                 190

Lys Ala Thr Cys Leu Leu Gly Arg Ser Ile Gly Leu Ala Tyr Glu Gly
        195                 200                 205

Lys Cys Ile Thr Lys Ser Cys Glu Asp Ile Gln Cys Gly Gly Gly Lys
    210                 215                 220

Lys Cys Leu Trp Asp Ser Lys Val Gly Arg Gly Arg Cys Ser Leu Cys
225                 230                 235                 240

Asp Glu Leu Cys Pro Asp Ser Lys Ser Asp Glu Pro Val Cys Ala Ser
                245                 250                 255

Asp Asn Ala Thr Tyr Ala Ser Glu Cys Ala Met Lys Glu Ala Ala Cys
            260                 265                 270

Ser Ser Gly Val Leu Leu Glu Val Lys His Ser Gly Ser Cys Asn Ser
        275                 280                 285

Ile Ser Glu Glu Thr Glu Glu Glu Glu Glu Asp Gln Asp Tyr
    290                 295                 300

Ser Phe Pro Ile Ser Ser Ile Leu Glu Trp

-continued

```
305                 310
```

<210> SEQ ID NO 34
<211> LENGTH: 315
<212> TYPE: PRT
<213> ORGANISM: Rattus sp.

<400> SEQUENCE: 34

```
Gly Asn Cys Trp Leu Arg Gln Ala Lys Asn Gly Arg Cys Gln Val Leu
1               5                   10                  15

Tyr Lys Thr Glu Leu Ser Lys Glu Glu Cys Cys Ser Thr Gly Arg Leu
            20                  25                  30

Ser Thr Ser Trp Thr Glu Glu Asp Val Asn Asp Asn Thr Leu Phe Lys
        35                  40                  45

Trp Met Ile Phe Asn Gly Gly Ala Pro Asn Cys Ile Pro Cys Lys Glu
    50                  55                  60

Thr Cys Glu Asn Val Asp Cys Gly Pro Gly Lys Lys Cys Arg Met Asn
65                  70                  75                  80

Lys Lys Asn Lys Pro Arg Cys Val Cys Ala Pro Asp Cys Ser Asn Ile
                85                  90                  95

Thr Trp Lys Gly Pro Val Cys Gly Leu Asp Gly Lys Thr Tyr Arg Asn
            100                 105                 110

Glu Cys Ala Leu Leu Lys Ala Arg Cys Lys Glu Gln Pro Glu Leu Glu
        115                 120                 125

Val Gln Tyr Gln Gly Lys Cys Lys Lys Thr Cys Arg Asp Val Phe Cys
    130                 135                 140

Pro Gly Ser Ser Thr Cys Val Val Asp Gln Thr Asn Asn Ala Tyr Cys
145                 150                 155                 160

Val Thr Cys Asn Arg Ile Cys Pro Glu Pro Ser Ser Glu Gln Ser
                165                 170                 175

Leu Cys Gly Asn Asp Gly Val Thr Tyr Ser Ser Ala Cys His Leu Arg
            180                 185                 190

Lys Ala Thr Cys Leu Leu Gly Arg Ser Ile Gly Leu Ala Tyr Glu Gly
        195                 200                 205

Lys Cys Ile Lys Ala Lys Ser Cys Glu Asp Ile Gln Cys Gly Gly Gly
    210                 215                 220

Lys Lys Cys Leu Trp Asp Phe Lys Val Gly Arg Gly Arg Cys Ser Leu
225                 230                 235                 240

Cys Asp Glu Leu Cys Pro Asp Ser Lys Ser Asp Glu Pro Val Cys Ala
                245                 250                 255

Ser Asp Asn Ala Thr Tyr Ala Ser Glu Cys Ala Met Lys Glu Ala Ala
            260                 265                 270

Cys Ser Ser Gly Val Leu Leu Glu Val Lys His Ser Gly Ser Cys Asn
        275                 280                 285

Ser Ile Ser Glu Glu Thr Glu Glu Glu Glu Glu Asp Gln Asp
    290                 295                 300

Tyr Ser Phe Pro Ile Ser Ser Thr Leu Glu Trp
305                 310                 315
```

<210> SEQ ID NO 35
<211> LENGTH: 315
<212> TYPE: PRT
<213> ORGANISM: Bos sp.

<400> SEQUENCE: 35

```
Gly Asn Cys Trp Leu Arg Gln Ala Lys Asn Gly Arg Cys Gln Val Leu
```

```
            1               5              10              15
Tyr Lys Thr Glu Leu Ser Lys Glu Glu Cys Cys Ser Thr Gly Arg Leu
                    20                  25                  30

Ser Thr Ser Trp Thr Glu Glu Asp Val Asn Asp Asn Thr Leu Phe Lys
            35                  40                  45

Trp Met Ile Phe Asn Gly Gly Ala Pro Asn Cys Ile Pro Cys Lys Glu
        50                  55                  60

Thr Cys Glu Asn Val Asp Cys Gly Pro Gly Lys Lys Cys Arg Met Asn
65                  70                  75                  80

Lys Lys Asn Lys Pro Arg Cys Val Cys Ala Pro Asp Cys Ser Asn Ile
                85                  90                  95

Thr Trp Lys Gly Pro Val Cys Gly Leu Asp Gly Lys Thr Tyr Arg Asn
            100                 105                 110

Glu Cys Ala Leu Leu Lys Ala Arg Cys Lys Glu Gln Pro Glu Leu Glu
        115                 120                 125

Val Gln Tyr Gln Gly Lys Cys Lys Lys Thr Cys Arg Asp Val Phe Cys
        130                 135                 140

Pro Gly Ser Ser Thr Cys Val Val Asp Gln Thr Asn Asn Ala Tyr Cys
145                 150                 155                 160

Val Thr Cys Asn Arg Ile Cys Pro Glu Pro Thr Ser Ser Glu Gln Tyr
                165                 170                 175

Leu Cys Gly Asn Asp Gly Val Thr Tyr Pro Ser Ala Cys His Leu Arg
            180                 185                 190

Lys Ala Thr Cys Leu Leu Gly Arg Ser Ile Gly Leu Ala Tyr Glu Gly
        195                 200                 205

Lys Cys Ile Lys Ala Lys Ser Cys Asp Asp Ile Gln Cys Thr Gly Gly
        210                 215                 220

Lys Lys Cys Leu Trp Asp Phe Lys Val Gly Arg Gly Arg Cys Ser Leu
225                 230                 235                 240

Cys Gly Glu Leu Cys Pro Glu Ser Lys Ser Glu Glu Pro Val Cys Ala
                245                 250                 255

Ser Asp Asn Ala Thr Tyr Ala Ser Glu Cys Ala Met Lys Glu Ala Ala
            260                 265                 270

Cys Ser Ser Gly Val Leu Leu Glu Val Lys His Ser Gly Ser Cys Asn
        275                 280                 285

Ser Ile Ser Glu Asp Thr Glu Asp Glu Glu Asp Glu Asp Gln Asp
        290                 295                 300

Tyr Ser Phe Pro Ile Ser Ser Ile Leu Glu Trp
305                 310                 315

<210> SEQ ID NO 36
<211> LENGTH: 315
<212> TYPE: PRT
<213> ORGANISM: Sus scrofa

<400> SEQUENCE: 36

Gly Asn Cys Trp Leu Arg Gln Ala Lys Asn Gly Arg Cys Gln Val Leu
1               5                  10                  15

Tyr Lys Thr Glu Leu Ser Lys Glu Glu Cys Cys Ser Thr Gly Arg Leu
                    20                  25                  30

Ser Thr Ser Trp Thr Glu Glu Asp Val Asn Asp Asn Thr Leu Phe Lys
            35                  40                  45

Trp Met Ile Phe Asn Gly Gly Ala Pro Asn Cys Ile Pro Cys Lys Glu
        50                  55                  60
```

```
Thr Cys Glu Asn Val Asp Cys Gly Pro Gly Lys Lys Cys Arg Met Asn
 65                  70                  75                  80

Lys Lys Asn Lys Pro Arg Cys Val Cys Ala Pro Asp Cys Ser Asn Ile
                 85                  90                  95

Thr Trp Lys Gly Pro Val Cys Gly Leu Asp Gly Lys Thr Tyr Arg Asn
            100                 105                 110

Glu Cys Ala Leu Leu Lys Ala Arg Cys Lys Glu Gln Pro Glu Leu Glu
            115                 120                 125

Val Gln Tyr Gln Gly Lys Cys Lys Lys Thr Cys Arg Asp Val Phe Cys
        130                 135                 140

Pro Gly Ser Ser Thr Cys Val Val Asp Gln Thr Asn Asn Ala Tyr Cys
145                 150                 155                 160

Val Thr Cys Asn Arg Ile Cys Pro Glu Pro Thr Ser Ser Glu Gln Tyr
                165                 170                 175

Leu Cys Gly Asn Asp Gly Val Thr Tyr Ser Ser Ala Cys His Leu Arg
            180                 185                 190

Lys Ala Thr Cys Leu Leu Gly Arg Ser Ile Gly Leu Ala Tyr Glu Gly
        195                 200                 205

Lys Cys Ile Lys Ala Lys Ser Cys Glu Asp Ile Gln Cys Thr Gly Gly
210                 215                 220

Lys Lys Cys Leu Trp Asp Phe Lys Val Gly Arg Gly Arg Cys Ser Leu
225                 230                 235                 240

Cys Asp Glu Leu Cys Pro Glu Ser Lys Ser Glu Pro Val Cys Ala
                245                 250                 255

Ser Asp Asn Ala Thr Tyr Ala Ser Glu Cys Ala Met Lys Glu Ala Ala
            260                 265                 270

Cys Ser Ser Gly Val Leu Leu Glu Val Lys His Ser Gly Ser Cys Asn
        275                 280                 285

Ser Ile Ser Glu Asp Thr Glu Glu Glu Glu Asp Glu Asp Gln Asp
        290                 295                 300

Tyr Ser Phe Pro Ile Ser Ser Ile Leu Glu Trp
305                 310                 315

<210> SEQ ID NO 37
<211> LENGTH: 315
<212> TYPE: PRT
<213> ORGANISM: Ovis sp.

<400> SEQUENCE: 37

Gly Asn Cys Trp Leu Arg Gln Ala Lys Asn Gly Arg Cys Gln Val Leu
  1               5                  10                  15

Tyr Lys Thr Glu Leu Ser Lys Glu Glu Cys Cys Ser Thr Gly Arg Leu
             20                  25                  30

Ser Thr Ser Trp Thr Glu Glu Asp Val Asn Asp Asn Thr Leu Phe Lys
         35                  40                  45

Trp Met Ile Phe Asn Gly Gly Ala Pro Asn Cys Ile Pro Cys Lys Glu
     50                  55                  60

Thr Cys Glu Asn Val Asp Cys Gly Pro Gly Lys Lys Cys Arg Met Asn
 65                  70                  75                  80

Lys Lys Asn Lys Pro Arg Cys Val Cys Ala Pro Asp Cys Ser Asn Ile
                 85                  90                  95

Thr Trp Lys Gly Pro Val Cys Gly Leu Asp Gly Lys Thr Tyr Arg Asn
            100                 105                 110

Glu Cys Ala Leu Leu Lys Ala Arg Cys Lys Glu Gln Pro Glu Leu Glu
            115                 120                 125
```

```
Val Gln Tyr Gln Gly Lys Cys Lys Lys Thr Cys Arg Asp Val Phe Cys
    130                 135                 140
Pro Gly Ser Ser Thr Cys Val Asp Gln Thr Asn Ala Tyr Cys
145                 150                 155                 160
Val Thr Cys Asn Arg Ile Cys Pro Glu Pro Thr Ser Ser Glu Gln Tyr
                165                 170                 175
Leu Cys Gly Asn Asp Gly Val Thr Tyr Pro Ser Ala Cys His Leu Arg
            180                 185                 190
Lys Ala Thr Cys Leu Leu Gly Arg Ser Ile Gly Leu Ala Tyr Glu Gly
        195                 200                 205
Lys Cys Ile Lys Ala Lys Ser Cys Glu Asp Ile Gln Cys Thr Gly Gly
    210                 215                 220
Lys Lys Cys Leu Trp Asp Phe Lys Val Gly Gly Arg Cys Ser Leu
225                 230                 235                 240
Cys Gly Glu Leu Cys Pro Glu Ser Lys Ser Glu Glu Pro Val Cys Ala
                245                 250                 255
Ser Asp Asn Ala Thr Tyr Ala Ser Glu Cys Ala Met Lys Glu Ala Ala
            260                 265                 270
Cys Ser Ser Gly Val Leu Leu Glu Val Lys His Ser Gly Ser Cys Asn
        275                 280                 285
Ser Ile Ser Glu Asp Thr Glu Asp Glu Glu Asp Glu Asp Gln Asp
    290                 295                 300
Tyr Ser Phe Pro Ile Ser Ser Ile Leu Glu Trp
305                 310                 315

<210> SEQ ID NO 38
<211> LENGTH: 315
<212> TYPE: PRT
<213> ORGANISM: Equus sp.

<400> SEQUENCE: 38

Gly Asn Cys Trp Leu Arg Gln Ala Lys Asn Gly Arg Cys Gln Val Leu
  1               5                  10                  15
Tyr Lys Thr Glu Leu Ser Lys Glu Glu Cys Cys Ser Thr Gly Arg Leu
                20                  25                  30
Ser Thr Ser Trp Thr Glu Glu Asp Val Asn Asp Asn Thr Leu Phe Lys
            35                  40                  45
Trp Met Ile Phe Asn Gly Gly Ala Pro Asn Cys Ile Pro Cys Lys Glu
        50                  55                  60
Thr Cys Asp Asn Val Asp Cys Gly Pro Gly Lys Lys Cys Arg Met Asn
65                  70                  75                  80
Lys Lys Asn Lys Pro Arg Cys Val Cys Ala Pro Asp Cys Ser Asn Ile
                85                  90                  95
Thr Trp Lys Gly Pro Val Cys Gly Leu Asp Gly Lys Thr Tyr Arg Asn
                100                 105                 110
Glu Cys Ala Leu Leu Lys Ala Arg Cys Lys Glu Gln Pro Glu Leu Glu
            115                 120                 125
Val Gln Tyr Gln Gly Lys Cys Lys Lys Thr Cys Arg Asp Val Asn Cys
    130                 135                 140
Pro Gly Ser Ser Thr Cys Val Val Asp Gln Thr Asn Asn Ala Tyr Cys
145                 150                 155                 160
Val Thr Cys Asn Arg Ile Cys Pro Glu Pro Thr Ser Ser Glu Gln Tyr
                165                 170                 175
Leu Cys Gly Asn Asp Gly Val Thr Tyr Ser Ser Ala Cys His Leu Arg
```

-continued

```
                180                 185                 190
Lys Ala Thr Cys Leu Leu Gly Arg Ser Ile Gly Leu Ala Tyr Glu Gly
            195                 200                 205

Lys Cys Ile Lys Ala Lys Ser Cys Glu Asp Ile Gln Cys Thr Gly Gly
        210                 215                 220

Lys Lys Cys Leu Trp Asp Phe Lys Val Gly Arg Gly Arg Cys Ser Leu
225                 230                 235                 240

Cys Asp Glu Leu Cys Pro Asp Ser Lys Ser Glu Pro Val Cys Ala
                245                 250                 255

Ser Asp Asn Ala Thr Tyr Ala Ser Glu Cys Ala Met Lys Glu Ala Ala
                260                 265                 270

Cys Ser Ser Gly Val Leu Leu Glu Val Lys His Ser Gly Ser Cys Asn
            275                 280                 285

Ser Ile Ser Glu Asp Thr Glu Glu Glu Glu Asp Glu Asp Gln Asp
        290                 295                 300

Tyr Ser Phe Pro Ile Ser Ser Ile Leu Glu Trp
305                 310                 315

<210> SEQ ID NO 39
<211> LENGTH: 315
<212> TYPE: PRT
<213> ORGANISM: Gallus gallus

<400> SEQUENCE: 39

Gly Asn Cys Trp Leu Arg Gln Ala Arg Asn Gly Arg Cys Gln Val Leu
1               5                   10                  15

Tyr Lys Thr Asp Leu Ser Lys Glu Glu Cys Cys Lys Ser Gly Arg Leu
            20                  25                  30

Thr Thr Ser Trp Thr Glu Glu Asp Val Asn Asp Asn Thr Leu Phe Lys
        35                  40                  45

Trp Met Ile Phe Asn Gly Gly Ala Pro Asn Cys Ile Pro Cys Lys Glu
    50                  55                  60

Thr Cys Glu Asn Val Asp Cys Gly Pro Gly Lys Lys Cys Lys Met Asn
65                  70                  75                  80

Lys Lys Asn Lys Pro Arg Cys Val Cys Ala Pro Asp Cys Ser Asn Ile
                85                  90                  95

Thr Trp Lys Gly Pro Val Cys Gly Leu Asp Gly Lys Thr Tyr Arg Asn
            100                 105                 110

Glu Cys Ala Leu Leu Lys Ala Arg Cys Lys Glu Gln Pro Glu Leu Glu
        115                 120                 125

Val Gln Tyr Gln Gly Lys Cys Lys Lys Thr Cys Arg Asp Val Leu Cys
    130                 135                 140

Pro Gly Ser Ser Thr Cys Val Val Asp Gln Thr Asn Asn Ala Tyr Cys
145                 150                 155                 160

Val Thr Cys Asn Arg Ile Cys Pro Glu Pro Thr Ser Pro Glu Gln Tyr
                165                 170                 175

Leu Cys Gly Asn Asp Gly Ile Thr Tyr Ala Ser Ala Cys His Leu Arg
            180                 185                 190

Lys Ala Thr Cys Leu Leu Gly Arg Ser Ile Gly Leu Ala Tyr Glu Gly
        195                 200                 205

Lys Cys Ile Lys Ala Lys Ser Cys Glu Asp Ile Gln Cys Ser Ala Gly
    210                 215                 220

Lys Lys Cys Leu Trp Asp Phe Lys Val Gly Arg Gly Arg Cys Ala Leu
225                 230                 235                 240
```

```
Cys Asp Glu Leu Cys Pro Glu Ser Lys Ser Asp Glu Ala Val Cys Ala
                245                 250                 255

Ser Asp Asn Thr Thr Tyr Pro Ser Glu Cys Ala Met Lys Glu Ala Ala
                260                 265                 270

Cys Ser Met Gly Val Leu Leu Glu Val Lys His Ser Gly Ser Cys Asn
            275                 280                 285

Ser Ile Asn Glu Asp Pro Glu Glu Glu Glu Asp Glu Asp Gln Asp
        290                 295                 300

Tyr Ser Phe Pro Ile Ser Ser Ile Leu Glu Trp
305                 310                 315

<210> SEQ ID NO 40
<211> LENGTH: 72
<212> TYPE: PRT
<213> ORGANISM: Mus musculus

<400> SEQUENCE: 40

Cys Arg Asp Val Phe Cys Pro Gly Ser Ser Thr Cys Val Val Asp Gln
  1               5                  10                  15

Thr Asn Asn Ala Tyr Cys Val Thr Cys Asn Arg Ile Cys Pro Glu Pro
             20                  25                  30

Ser Ser Ser Glu Gln Tyr Leu Cys Gly Asn Asp Gly Val Thr Tyr Ser
         35                  40                  45

Ser Ala Cys His Leu Arg Lys Ala Thr Cys Leu Leu Gly Arg Ser Ile
     50                  55                  60

Gly Leu Ala Tyr Glu Gly Lys Cys
 65                  70
```